United States Patent
Prud'homme et al.

(10) Patent No.: US 11,731,099 B2
(45) Date of Patent: Aug. 22, 2023

(54) METHOD FOR CONTROLLING ENCAPSULATION EFFICIENCY AND BURST RELEASE OF WATER SOLUBLE MOLECULES FROM NANOPARTICLES AND MICROPARTICLES PRODUCED BY INVERSE FLASH NANOPRECIPITATION

(71) Applicant: The Trustees of Princeton University, Princeton, NJ (US)

(72) Inventors: Robert K. Prud'homme, Princeton, NJ (US); Robert F. Pagels, Princeton, NJ (US); Chester E. Markwalter, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 16/517,510

(22) Filed: Jul. 19, 2019

(65) Prior Publication Data

US 2020/0023332 A1 Jan. 23, 2020

Related U.S. Application Data

(60) Provisional application No. 62/700,934, filed on Jul. 20, 2018.

(51) Int. Cl.
| | |
|---|---|
| *B01J 13/02* | (2006.01) |
| *C08J 3/21* | (2006.01) |
| *B01J 13/22* | (2006.01) |
| *C08J 3/215* | (2006.01) |
| *C08J 3/22* | (2006.01) |
| *C08G 81/02* | (2006.01) |
| *B01J 13/14* | (2006.01) |
| *B82Y 40/00* | (2011.01) |
| *B82Y 30/00* | (2011.01) |
| *B82Y 35/00* | (2011.01) |

(52) U.S. Cl.
CPC ............ *B01J 13/025* (2013.01); *B01J 13/14* (2013.01); *B01J 13/22* (2013.01); *C08G 81/025* (2013.01); *C08G 81/027* (2013.01); *C08J 3/212* (2013.01); *C08J 3/215* (2013.01); *C08J 3/226* (2013.01); *B82Y 30/00* (2013.01); *B82Y 35/00* (2013.01); *B82Y 40/00* (2013.01)

(58) Field of Classification Search
CPC . B01J 13/025; B01J 13/22; B01J 13/14; B01J 13/206; B01J 13/18; C08J 3/212; C08J 3/215; C08J 3/226; C08J 3/126; C08G 81/025; C08G 81/027; B82Y 40/00; B82Y 30/00; B82Y 35/00; A61K 9/5036
See application file for complete search history.

(56) References Cited

U.S. PATENT DOCUMENTS

| | | | |
|---|---|---|---|
| 4,342,653 | A | 8/1982 | Halverson |
| 4,382,982 | A | 5/1983 | Whillans |
| 4,888,238 | A | 12/1989 | Katz et al. |
| 4,999,417 | A | 3/1991 | Domb |
| 5,366,734 | A | 11/1994 | Hutchinson |
| 5,578,325 | A | 11/1996 | Domb et al. |
| 6,291,013 | B1 | 9/2001 | Gibson et al. |
| 6,383,500 | B1 | 5/2002 | Wooley et al. |
| 6,730,322 | B1 | 5/2004 | Bernstein et al. |
| 7,977,024 | B2 | 7/2011 | Zhou et al. |
| 8,137,699 | B2 | 3/2012 | Johnson et al. |
| 8,288,001 | B1 | 10/2012 | Fan et al. |
| 9,782,358 | B2 | 10/2017 | Kataoka et al. |
| 10,231,937 | B2 | 3/2019 | Pagels et al. |
| 11,103,461 | B2 | 8/2021 | Prud'Homme et al. |
| 2004/0091546 | A1 | 5/2004 | Johnson et al. |
| 2004/0236050 | A1 | 11/2004 | Lundquist et al. |
| 2005/0158390 | A1 | 7/2005 | Rana et al. |
| 2005/0228074 | A1 | 10/2005 | Warren et al. |
| 2006/0040831 | A1 | 2/2006 | Cassidy et al. |
| 2006/0057215 | A1 | 3/2006 | Raiche et al. |
| 2006/0078624 | A1 | 4/2006 | Zalipsky et al. |

(Continued)

FOREIGN PATENT DOCUMENTS

| | | |
|---|---|---|
| CN | 102334609 A | 2/2012 |
| CN | 104042567 A | 9/2014 |

(Continued)

OTHER PUBLICATIONS

Polymeric nanoparticles and microparticles for the delivery of peptides, biologies, and soluble therapeutics by Robert F. Pagels, et al., J. Control Release, , 2015, 519-535.*
Mai et al., "Controlled Incorporation of Particles into the Central Portion of Vesicle Walls", J. Am. Chem. Soc., vol. 132, pp. 10078-10084 (2010).
Kumar et al., "Amphiphilic Janus particles at fluid interfaces", Soft Matter, vol. 9, pp. 6604-6617 (2013).
Sahoo et al., "Characterization of Porous PLGA/PLA Microparticles as a Scaffold for Three Dimensional Growth of Breast Cancer Cells", Biomacromolecules, vol. 6, pp. 1132-1139 (2005).

(Continued)

*Primary Examiner* — Irina S Zemel
(74) *Attorney, Agent, or Firm* — Nixon & Vanderhye, P.C.; Lars H. Genieser

(57) ABSTRACT

A method for controlling the encapsulation efficiency and burst release of water soluble molecules from nanoparticle and microparticle formulations produced by the inverted Flash NanoPrecipitation (iFNP) process and subsequent processing steps is presented. The processing steps and materials used can be adjusted to tune the encapsulation efficiency and burst release of the encapsulated water-soluble material. The encapsulation efficiency of the soluble agent in the particles and the burst release of the soluble agent from the particles can be controlled by: (1) the copolymers used in the assembly or coating process, (2) the degree of crosslinking of the nanoparticle core, (3) the incorporation of small molecule or polymeric additives, and/or (4) the processing and release conditions employed.

19 Claims, 16 Drawing Sheets

(56) References Cited

U.S. PATENT DOCUMENTS

| | | |
|---|---|---|
| 2006/0159921 A1 | 7/2006 | Murthy et al. |
| 2006/0224095 A1 | 10/2006 | Claverie et al. |
| 2006/0247383 A1 | 11/2006 | Hedrick et al. |
| 2007/0042498 A1 | 2/2007 | Ebner |
| 2007/0231355 A1 | 10/2007 | Quadir et al. |
| 2008/0145432 A1 | 6/2008 | Kakizawa et al. |
| 2008/0160305 A1 | 7/2008 | Warren et al. |
| 2009/0061009 A1 | 3/2009 | Schwarz et al. |
| 2009/0155326 A1 | 6/2009 | Mack et al. |
| 2009/0325292 A1 | 12/2009 | Baker et al. |
| 2010/0150994 A1 | 6/2010 | Kotyla |
| 2010/0203149 A1 | 8/2010 | Radosz et al. |
| 2010/0233251 A1 | 9/2010 | Von Andrian et al. |
| 2010/0305219 A1 | 12/2010 | Granick et al. |
| 2010/0310649 A1 | 12/2010 | Richard et al. |
| 2010/0330368 A1 | 12/2010 | Prud'homme et al. |
| 2011/0012057 A1 | 1/2011 | Lindner et al. |
| 2011/0022129 A1 | 1/2011 | Prud'homme et al. |
| 2011/0064821 A1 | 3/2011 | Catchpole et al. |
| 2011/0200828 A1 | 8/2011 | Li et al. |
| 2011/0236686 A1 | 9/2011 | Kitano et al. |
| 2011/0293701 A1 | 12/2011 | Bratzler et al. |
| 2012/0009267 A1 | 1/2012 | Cho et al. |
| 2012/0041150 A1 | 2/2012 | Yabu et al. |
| 2012/0121510 A1 | 5/2012 | Brem et al. |
| 2012/0171254 A1 | 7/2012 | Johnson et al. |
| 2012/0230913 A1 | 9/2012 | Johnston et al. |
| 2012/0308640 A1 | 12/2012 | Percec et al. |
| 2013/0101516 A1 | 4/2013 | Zhao |
| 2013/0122058 A1 | 5/2013 | Chow et al. |
| 2013/0171208 A1 | 7/2013 | Smith et al. |
| 2013/0337078 A1 | 12/2013 | Mayer et al. |
| 2014/0037573 A1 | 2/2014 | Eliasof et al. |
| 2014/0099379 A1 | 4/2014 | Beck-Broichsitter et al. |
| 2014/0249235 A1 | 9/2014 | Brugel et al. |
| 2014/0356443 A1 | 12/2014 | Brisander et al. |
| 2015/0086618 A1 | 3/2015 | Onyuksel et al. |
| 2015/0218198 A1 | 8/2015 | Petermann et al. |
| 2015/0283218 A1 | 10/2015 | Shea et al. |
| 2015/0299369 A1 | 10/2015 | Ausserre et al. |
| 2016/0317459 A1 | 11/2016 | Ensign et al. |
| 2016/0346266 A1 | 12/2016 | Tolleth et al. |
| 2017/0042823 A1 | 2/2017 | Prud'Homme et al. |
| 2017/0151339 A1 | 6/2017 | White et al. |
| 2019/0008788 A1 | 1/2019 | Prud'Homme et al. |
| 2019/0151252 A1 | 5/2019 | Pagels et al. |
| 2020/0206136 A1 | 7/2020 | Prud'Homme et al. |

FOREIGN PATENT DOCUMENTS

| | | | |
|---|---|---|---|
| EP | 2962752 A1 | 1/2016 | |
| JP | 2003513019 A | 4/2003 | |
| JP | 2008297288 A | 12/2008 | |
| JP | 2014514275 A | 6/2014 | |
| JP | 2015129128 A | 7/2015 | |
| JP | 2015529683 A | 10/2015 | |
| JP | 2017505800 A | 2/2017 | |
| JP | 2018535228 A | 11/2018 | |
| WO | 1994008599 A1 | 4/1994 | |
| WO | 1997049736 A2 | 12/1997 | |
| WO | 2001022937 A1 | 4/2001 | |
| WO | 2002076441 A1 | 10/2002 | |
| WO | 2002078674 A1 | 10/2002 | |
| WO | 2009080164 A1 | 7/2009 | |
| WO | 2012122544 A2 | 9/2012 | |
| WO | 2013023003 A1 | 2/2013 | |
| WO | 2013160773 A2 | 10/2013 | |
| WO | 2014043625 A1 | 3/2014 | |
| WO | 2014133172 A1 | 9/2014 | |
| WO | 2014165679 A1 | 10/2014 | |
| WO | 2015123562 A1 | 8/2015 | |
| WO | 2015130835 A1 | 9/2015 | |
| WO | 2015200054 A2 | 12/2015 | |
| WO | 2015200054 A9 | 12/2015 | |
| WO | 2016193810 A1 | 12/2016 | |
| WO | 2017089942 A1 | 6/2017 | |
| WO | WO-2017112828 A1 * | 6/2017 | ........... A61K 9/5026 |
| WO | 2019055539 A1 | 3/2019 | |
| WO | 2019090030 A1 | 5/2019 | |
| WO | 2020018890 A1 | 1/2020 | |

OTHER PUBLICATIONS

Sosa et al., "Soft Multifaced and Patchy Colloids by Constrained Volume Self-Assembly", Macromolecules, vol. 49, pp. 3580-3585 (2016).

Int'l Search Report and Written Opinion dated Jan. 26, 2018 in Int'l Application No. PCT/US2017/054779.

International Search Report and Written Opinion dated Jan. 26, 2018 in International Application No. PCT/US2017/054779.

Liu et al., "Janus Colloids Formed by Biphasic Grafting at a Pickering Emulsion Interface", Angew. Chem., vol. 120, pp. 4037-4039 (2008).

Saad et al., "Principles of nanoparticle formation by Flash Nanoprecipitation", Nano Today, vol. 11, No. 2, pp. 212-227 (2016), http://dx.doi.org/10.1016/j.nantod.2016.04.006.

International Search Report and Written Opinion dated Jan. 15, 2019 in International Application No. PCT/US2018/049580.

Guo et al., "Binding of dihydromyricetin and its metal ion complexes with bovine serum albumin", Biotechnology & Biotechnological Equipment, vol. 28, No. 2, pp. 333-341 (2014).

Guo et al., "Synthesis of dihydromyricetin-manganese (II) complex and interaction with DNA", J. Molecular Structure, vol. 1027, pp. 64-69 (2012).

Xu et al., "Scalable method to produce biodegradable nanoparticles that rapidly penetrate human mucus", Journal of Controlled Release, vol. 170, pp. 279-286 (2013).

International Search Report and Written Opinion dated Dec. 6, 2018 in International Application No. PCT/US2018/050714.

Solaro et al., "Targeted Delivery of Protein Drugs by Nanocarriers", Materials, vol. 3, No. 3, pp. 1928-1980 (2010).

Steichen et al., "A review of current nanoparticle and targeting moieties for the delivery of cancer therapeutics", European J. Pharmaceutical Sciences, vol. 48, pp. 416-427 (2013).

Kang et al., "Pore Closing and Opening in Biodegradable Polymers and Their Effect on the Controlled Release of Proteins", Mol. Pharmaceutics, vol. 4, No. 1, pp. 104-118 (2007).

Wang et al., "Characterization of the initial burst release of a model peptide from poly(D,L-lactide-co-glycolide) microspheres", J. Controlled Release, vol. 82, pp. 289-307 (2002).

Kim et al., "Critical effect of freezing/freeze-drying on sustained release of FITC-dextran encapsulated within PLGA microspheres", Int'l J. Pharmaceutics, vol. 271, pp. 207-214 (2004).

Groeschel et al., "Guided hierarchical co-assembly of soft patchy nanoparticles", Nature, vol. 503, pp. 247-251 (5 pages & 11 pages Methods, Extended Data Figures 1-9, & Extended Data Table 1) (Nov. 14, 2013).

Jang et al., "Synthesis of thermally stable Au-core/Pt-shell nanoparticles and their segregation behavior in diblock copolymer mixtures", Soft Matter, vol. 7, pp. 6255-6263 (2011), doi: 10.1039/c1sm05223c.

Jeon et al., "Cooperative Assembly of Block Copolymers with Deformable Interfaces: Toward Nanostructured Particles", Advanced Materials, vol. 20, pp. 4103-4108 (2008), doi: 10.1002/adma.200801377.

Riess et al., "Emulsifying Properties of Block Copolymers. Oil-Water Emulsions and Microemulsions", Polym. Eng. Sci., vol. 17, No. 8, pp. 634-638 (1977).

International Search Report and Written Opinion dated Feb. 22, 2019 in International Application No. PCT/US2018/058869.

International Search Report and Written Opinion dated Nov. 22, 2019 in International Application No. PCT/US2019/042574.

Jang et al., "Bicontinuous Block Copolymer Morphologies Produced by Interfacially Active, Thermally Stable Nanoparticles", Macromols., vol. 44, pp. 9366-9373 (2011).

Deng et al., "Janus Nanoparticles of Block Copolymers by Emulsion Solvent Evaporation Induced Assembly," Macromolecules, vol. 49, pp. 1362-1368 (2016).

(56) References Cited

OTHER PUBLICATIONS

Talelli et al., "Core-crosslinked polymeric micelles: Principles, preparation, biomedical applications and clinical translation," Nano Today, vol. 10, pp. 93-117 (2015).
U.S. Patent & Trademark Office (USPTO) Office Action dated May 12, 2021 for U.S. Appl. No. 16/810,710.
U.S. Patent & Trademark Office (USPTO) Communication dated Mar. 9, 2021 for U.S. Appl. No. 16/253,850.
Anton et al., "Aqueous-Core Lipid Nanocapsules for Encapsulating Fragile Hydrophilic and/or Lipophilic Molecules," Langmuir, vol. 25, No. 19, pp. 11413-11419 (2009).
IQQueryQuickExport search results—202004301659 (IP.com NPL search results)—downloaded Apr. 30, 2020, 5 pages.
IQQueryQuickExport search results—202004301700 (IP.com NPL search results)—downloaded Apr. 30, 2020, 2 pages.
IQQueryQuickExport search results—202004301605 (IP.com NPL search results)—downloaded Apr. 30, 2020, 5 pages.
IQQueryQuickExport search results—202004301516 (IP.com NPL search results)—downloaded Apr. 30, 2020, 4 pages.
IQQueryQuickExport search results—202004301643 (IP.com NPL search results)—downloaded Apr. 30, 2020, 5 pages.
IQQueryQuickExport search results—202004301547 (IP.com NPL search results)—downloaded Apr. 30, 2020, 2 pages.
Google Scholar NPL search string—downloaded Apr. 29, 2020, 1 page.
U.S. Appl. No. 16/064,935 Notice of Allowance dated Oct. 21, 2020.
U.S. Appl. No. 16/064,935 Notice of Allowance dated Apr. 28, 2021.
U.S. Appl. No. 16/064,935 Notice of Allowance dated Jun. 21, 2021.
U.S. Appl. No. 16/064,935 Notice of Allowance dated Aug. 2, 2021.
Pustulka, K.M. et al., Flash Nanoprecipitation: Particle Structure and Stability, Mol. Pharmaceutics, 10, 4367-4377 (2013).
International Preliminary Report on Patentability dated Mar. 26, 2020 in International Application No. PCT/US2018/050714.
Schwendeman et al., "Injectable controlled release depots for large molecules", Journal of Controlled Release, vol. 190, 28, pp. 240-253, Sep. 2014.
Shah et al., Poly (Glycolic acid-co-DL-lactic acid): diffusion or degradation controlled drug delivery?, Journal of Controlled Release, vol. 18, Issue 3, pp. 261-270, 1992.
Reinhold et al., "Self-Healing Microencapsulation of Biomacromolecules without Organic Solvents", Angewandte Chemie, vol. 124, Issue 43, pp. 10958-10961, Oct. 2012.
Ilton et al., "Direct Measurement of the Critical Pore Size in a Model Membrane", Physical Review Letters, 117, Issue 25, Dec. 2016.
Pagels et al., "Inverse Flash NanoPrecipitation for Biologies Encapsulation: Nanoparticle Formation and Ionic Stabilization in Organic Solvents", ACS Symp. Ser., vol. 1271 , pp. 249-274, 2017.
U.S. Patent & Trademark Office (USPTO) Office Action dated Sep. 23, 2021 for U.S. Appl. No. 16/253,850.
U.S. Appl. No. 16/253,850, filed Aug. 11, 2021 dated Summary of Interview dated Aug. 9, 2021.
U.S. Appl. No. 16/816,241 Restriction Requirement dated Sep. 30, 2021.
Pagels et al., "Polymeric nanoparticles and microparticles for the delivery of peptides, biologies, and soluble therapeutics", J. Controlled Release, vol. 219, pp. 519-535 (2015).
Reinhold et al., "Self-healing Microencapsulation of Biomacromolecules without Organic Solvents", Angew. Chem. Int. Ed. Engl., vol. 51, No. 43, pp. 10800-10803 (2012).
Int'l Search Report and Written Opinion dated Sep. 18, 2015 in Int'l Application PCT/US2015/036060.
Bronich et al., "Polymer Micelle with Cross-Linked Ionic Core", J. Am. Chem Soc., vol. 127, pp. 8236-8237 (2005).
Arshady, "Preparation of biodegradable microspheres and microcapsules: 2. Polyactides and related polyesters", Journal of Controlled Release, vol. 17, pp. 1-22, (1991).

Holland et al., "Polymers for Biodegradable Medical Devices, 1. The Potential of Polyesters As Controlled by Macromolecular Release Systems", Journal of Controlled Release, vol. 4, pp. 155-180 (1986).
Lavasanifar et al., "Poly(ethylene oxide)-block-poly(L-amino acid) micelles for drug delivery", Advanced Drug Delivery Reviews, vol. 54, pp. 169-190 (2002).
Liu et al., "CFD Predictions for Chemical Processing in a Confined Impinging-Jets Reactor", AIChE Journal, vol. 52, No. 2, pp. 731-744 (Feb. 2006).
Pitt, "The controlled parenteral delivery of polypeptides and proteins", International Journal of Pharmaceutics, vol. 59, pp. 173-196 (1990).
Bontha et al., "Polymer micelles with cross-linked ionic cores for delivery of anticancer drugs", Journal of Controlled Release, vol. 114, pp. 163-174 (2006).
Zhang et al., "Amphiphilic cylindrical brushes with poly(acrylic acid) core and poly(n-butyl acrylate) shell and narrow length distribution", Polymer, vol. 44, pp. 1449-1458 (2003).
Sato et al., "Therapeutic peptides: technological advances driving peptides into development", Current Opinion in Biotechnology, vol. 17, pp. 638-642 (2006).
Peters et al., "Biotech Products in Big Pharma Clinical Pipelines Have Grown Dramatically According to the Tufts Center for the Study of Drug Development", Nov. 14, 2013, https://www.biospace.com/...a-clinical-pipelines-have-grown-dramatically-according-to-the-tufts-center-for-the-study-of-drug-development-/, accessed Aug. 29, 2018 (5 pages).
Liu et al., "Mixing in a multi-inlet vortex mixer (MIVM) for flash nano-precipitation", Chemical Engineering Science, vol. 63, pp. 2829-2842 (2008).
Mitragotri et al. "Overcoming the challenges in administering biopharmaceuticals: formulation and delivery strategies", Nat. Rev. Drug Discov., vol. 13, No. 9, pp. 655-672 (Sep. 2014).
Patil et al., "Retention of trypsin activity in spermine alginate microcapsules", Journal of Microencapsulation, vol. 14, No. 4, pp. 469-474 (1997).
Bronich et al., "Soluble Complexes from Poly(ethylene oxide)-block-polymethacrylate Anions and N-Alkylpyridinium Cations", Macromolecules, vol. 30, pp. 3519-3525 (1997).
Bilati et al., "Nanoprecipitation Versus Emulsion-based Techniques for the Encapsulation of Proteins Into Biodegradable Nanoparticles and Process-related Stability Issues", AAPS PharmSciTech, vol. 6, No. 4, Article 74, pp. E594-E604 (2005).
Extended European Search Report (EESR) dated Jan. 8, 2018 in European Application No. 15811879.4.
Prud'Homme et al., "Process for Encapsulating Soluble Biologies Therapeutics, and Imaging Agents", U.S. Appl. No. 16/064,935, filed Jun. 21, 2018.
Kakizawa et al., "Controlled release of protein drugs from newly developed amphiphilic polymer-based microparticles composed of nanoparticles", Journal of Controlled Release, vol. 142, pp. 8-13 (2010).
D'Addio et al., "Controlling drug nanoparticle formation by rapid precipitation", Advanced Drug Delivery Reviews, vol. 63, pp. 417-426 (2011).
Okuyama et al., "Preparation of functional nanostructured particles by spray drying", Advanced Powder Technol., vol. 17, No. 6, pp. 587-611 (2006).
D'Reilly et al., "Cross-linked block copolymer micelles: functional nanostructures of great potential and versatility", Chemical Society Reviews, vol. 35, pp. 1068-1083 (2006).
Johnson et al., "Characterization and Suitability of Therapeutic Antibody Dense Phases for Subcutaneous Delivery", Molecular Pharmaceutics, vol. 10, pp. 3582-3591 (2013).
Johnston et al., "Concentrated Dispersions of Equilibrium Protein Nanoclusters That Reversibly Dissociate into Active Monomers", ACS Nano, vol. 6, No. 2, pp. 1357-1369 (2012).
Johnson et al., "Chemical Processing and Micromixing in Confined Impinging Jets", AIChE Journal, vol. 49, No. 9, pp. 2264-2282 (2003).
Int'l Search Report and Written Opinion dated Jul. 16, 2015 in Int'l Application No. PCT/US2015/017590.

(56) References Cited

OTHER PUBLICATIONS

Bilati et al., "Development of a nanoprecipitation method intended for the entrapment of hydrophilic drugs into nanoparticles", European J. Pharmaceutical Sciences, vol. 24, pp. 67-75 (2005).
Gao et al., "Core Cross-Linked Reverse Micelles from Star-Shaped Polymers," Chemistry of Materials, vol. 20, pp. 3063-3067 (2008).
Int'l Search Report and Written Opinion dated Mar. 23, 2017 in Int'l Application No. PCT/US2016/068145.
Liang et al., "Preparation of nanoparticles composed of poly(gamma-glutamic acid)-poly(lactide) block copolymers and evaluation of their uptake by HepG2 cells," J. Controlled Release, vol. 105, pp. 213-225 (2005).
Pustulka et al., "Flash Nanoprecipitation: Particle Structure and Stability," Molecular Pharmaceutics, vol. 10, pp. 4367-4377 (2013).
Zandonella, "Bob Prud'homme—Flash NanoPrecipitation" http://research.princeton.edu/news/features/a/index.xml?id=6234, accessed Mar. 9, 2018, originally published Dec. 9, 2011, 2 printed pages.
Zhu et al., "Preparation and characterization of hCG-loaded polylactide or poly(lactide-co-glycolide) microspheres using a modified water-in-oil-in-water (w/o/w) emulsion solvent evaporation technique," J. Microencapsulation, vol. 18, No. 2, pp. 247-260 (2001).
U.S. Appl. No. 15/321,588 Notice of Allowance dated Oct. 24, 2018.
U.S. Appl. No. 15/321,588 Summary of Examiner Interview dated Oct. 9, 2018.
U.S. Appl. No. 15/321,588 Office Action dated Apr. 10, 2018.
U.S. Appl. No. 15/321,588 Restriction Requirement dated Dec. 1, 2017.
U.S. Appl. No. 16/253,850 Restriction Requirement dated Apr. 7, 2020.
U.S. Appl. No. 16/064,935 Requirement for Restriction/Election dated Jan. 13, 2020.
U.S. Appl. No. 16/064,935 Notice of Allowance dated May 6, 2020.
Colombani et al., "Synthesis of Poly(n-butyl acrylate)-block-poly(acrylic acid) Diblock Copolymers by ATRP and Their Micellization in Water," Macromolecules, vol. 40, pp. 4338-4350 (2007).
Colombani et al., "Structure of Micelles of Poly(n-butyl acrylate)-block-poly(acrylic acid) Diblock Copolymers in Aqueous Solution," Macromolecules, vol. 40, pp. 4351-4362 (2007).
Eghbali et al., "Rheology and Phase Behavior of Poly(n-butyl acrylate)-block-poly(acrylic acid) in Aqueous Solution," Langmuir, vol. 22, pp. 4766-4776 (2006).
Kohen, N., "Characterization of Polystyrene-block-poly(acrylic acid) Micelles In Solution and Assembled on Solid Substrates," Massachusetts Institute of Technology, Thesis, Jun. 2005, pp. 1-38 (2005).
Kim et al., "Multicomponent Nanoparticles via Self-Assembly with Cross-Linked Block Copolymer Surfactants," Langmuir, vol. 23, pp. 2198-2202 (2007).
Qi et al., "Determination of the Bioavailability of Biotin Conjugated onto Shell Cross-Linked (SCK) Nanoparticles," Journal of the American Chemical Society, vol. 126, pp. 6599-6607 (2004).
Erre et al., "Chromium(III) Acetate, Chromium(III) Acetate Hydroxide, or m3-Oxo-esakis-(m2-acetato-O,O')-triaqua-trichromium(III) Acetate?" Journal of Chemical Education, vol. 74, No. 4, pp. 432-435 (1997).
U.S. Appl. No. 16/253,850 Office Action dated Sep. 8, 2020.
Foerster et al., "Amphiphilic Block Copolymers in Structure-Controlled Nanomaterial Hybrids", Advanced Materials, vol. 10, No. 3, pp. 195-217 (1998).
Johnson et al., "Nanoprecipitation of organic actives using mixing and block copolymer stabilization", Abstracts of Papers of the American Chemical Society, No. 186 (Abstract) (Sep. 2003).
Aggarwal et al., "What's fueling the biotech engine—2012 to 2013", Nat. Biotechnol., vol. 32, No. 1, pp. 32-39, Jan. 2014.
Ansell et al., "Modulating the Therapeutic Activity of Nanoparticle Delivered Paclitaxel by Manipulating the Hydrophobicity of Prodrug Conjugates," Journal of Medicinal Chemistry, vol. 51, No. 11, pp. 3288-3296 (2008).
Antonietti et al., "Polyelectrolyte-Surfactant Complexes: A New Type of Solid, Mesomorphous Material," Macromolecules, vol. 27, No. 21, pp. 6007-6011 (1994).
Antonov et al., "Entering and exiting the protein?polyelectrolyte coacervate phase via nonmonotonic salt dependence of critical conditions," Biomacromolecules, vol. 11, No. 1, pp. 51-59 (2009).
Bruno et al., Basics and recent advances in peptide and protein drug delivery, Therapeutic Delivery, vol. 4, No. 11, pp. 1443-1467 (2013).
Crater et al., "Barrier Properties of Gastrointestinal Mucus to Nanoparticle Transport," Macromolecular Bioscience, vol. 10, No. 12, pp. 1473-1483 (2010).
Cu et al., "Drug delivery: Stealth particles give mucus the slip," Nature Materials, vol. 8, No. 1, pp. 11-13 (2009).
Davies et al., "Recent advances in the management of cystic fibrosis," Archives of Disease in Childhood, vol. 99, No. 11, pp. 1033-1036 (2014).
Ensign et al., "Oral drug delivery with polymeric nanoparticles: The gastrointestinal mucus barriers," Advanced Drug Delivery Reviews, vol. 64, No. 6, pp. 557-570 (2012).
Galindo-Rodriguez et al., "Polymeric nanoparticles for oral delivery of drugs and vaccines: a critical evaluation of in vivo studies," Critical Reviews in Therapeutic Drug Carrier Systems, vol. 22, No. 5, pp. 419-464 (2005).
Gaudana et al., "Design and evaluation of a novel nanoparticulate-based formulation encapsulating a HIP complex of lysozyme," Pharmaceutical Development and Technology, vol. 18, No. 3, pp. 752-759 (2013).
Gindy et al., "Mechanism of macromolecular structure evolution in self-assembled lipid nanoparticles for siRNA delivery," Langmuir, vol. 30, No. 16, pp. 4613-4622 (2014).
Gregory et al., "Adsorption and flocculation by polymers and polymer mixtures", Advances in Colloid and Interface Science, vol. 169, No. 1, pp. 1-12 (2011).
Horigome, et al., "Long-Time Relaxation of Suspensions Flocculated by Associating Polymers", Langmuir, vol. 18, No. ô, pp. 1968-1973 (2002).
Høiby, N., "Recent advances in the treatment of Pseudomonas aeruginosa infections in cystic fibrosis," BMC Medicine, vol. 9, p. 32 (2011).
Immordino et al., "Stealth liposomes: review of the basic science, rationale, and clinical applications, existing and potential," International Journal of Nanomedicine, vol. 1, No. 3, pp. 297-315 (2006).
Jain et al., "Peptide and Protein Delivery Using New Drug Delivery Systems," Crit. Rev. Ther. Drug Carrier Syst., vol. 30, No. 4, pp. 293-329 (2013).
Johnson et al., "Flash NanoPrecipitation of Organic Actives and Block Copolymers using a Confined Impinging Jets Mixer," Australian Journal of Chemistry, vol. 56, No. 10, pp. 1021-1024 (2003).
Khanvilkar et al., "Drug transfer through mucus," Advanced Drug Delivery Reviews, vol. 48, Nos. 2-3, pp. 173-193 (2001).
Kovalainen et al., "Novel Delivery Systems for Improving the Clinical Use of Peptides", Pharmacol. Rev., vol. 67, No. 3, pp. 541-561 (Jul. 2015).
Lai et al., "Mucus-penetrating nanoparticles for drug and gene delivery to mucosal tissues," Advanced Drug Delivery Reviews, vol. 61, No. 2, pp. 158-171 (2009).
Lai et al., "Rapid transport of large polymeric nanoparticles in fresh undiluted human mucus," Proceedings of the National Academy of Sciences, vol. 104, No. 5, pp. 1482-1487 (2007).
Langer, R., "Drug delivery and targeting," Nature, vol. 392, No. 6679, pp. 5-10 (1998).
Li et al., "Pharmacokinetics and Biodistribution of Nanoparticles," Molecular Pharmaceutics, vol. 5, No. 4, pp. 496-504 2008).
Liu et al., "Ostwald ripening of beta-carotene nanoparticles," Phys. Rev. Lett., vol. 98, No. 3, p. 036102 (2007).
Livraghi et al., "Cystic Fibrosis and Other Respiratory Diseases of Impaired Mucus Clearance," Toxicologic Pathology, vol. 35, No. 1, pp. 116-129 (2007).
Lu et al., "Hydrophobic Ion Pairing of Peptide Antibiotics for Processing into Controlled Release Nanocarrier Formulations", Molecular Pharmaceutics, vol. 15, No. 1, pp. 216-225 (2018).

(56) References Cited

OTHER PUBLICATIONS

Luo et al., "Synthetic DNA delivery systems," Nature Biotechnology, vol. 18, No. 1, pp. 33-37 (2000).
Marcus et al., "Ion Pairing," Chemical Reviews, vol. 106, No. 11, pp. 4585-4621 (2006).
Markwalter et al., "Inverse Flash NanoPrecipitation for Biologics Encapsulation: Understanding Process Losses via an Extraction Protocol", Control of Amphiphile Self-Assembling at the Molecular Level: Supra-Molecular Assemblies with Tuned Physicochemical Properties for Delivery Applications, pp. 275-296 (Jan. 1, 2017).
Matschiner et al., "Optimization of topical erythromycin formulations by ion pairing," Skin Pharmacology: The Official Journal of the Skin Pharmacology Society, vol. 8, No. 6, pp. 319-325 (1995).
Meyer et al. "Hydrophobic Ion Pairing: Altering the Solubility Properties of Biomolecules," Pharmaceutical Research, vol. 15, No. 2, pp. 188-193 (1998).
Muehle et al., "Stability of Particle Aggregates in Flocculation with Polymers: Stabilität von Teilchenaggregaten bei der Flockung mit Polymeren", Chemical Engineering and Processing: Process Intensification, vol. 29, No. 1, pp. 1-8 (1991).
Mueller et al., "Solid lipid nanoparticles (SLN) for controlled drug delivery-a review of the state of the art," European Journal of Pharmaceutics and Biopharmaceutics, vol. 50, No. 1, pp. 161-177 (2000).
Muheem et al., "A review on the strategies for oral delivery of proteins and peptides and their clinical perspectives," Saudi Pharmaceutical Journal, vol. 24, No. 4, pp. 413-428 (2016).
Overbeek et al., "Phase separation in polyelectrolyte solutions. Theory of complex coacervation," Journal of Cellular Physiology, vol. 49, No. S1, pp. 7-26 (1957).
Owens et al., "Opsonization, biodistribution, and pharmacokinetics of polymeric nanoparticles," International Journal of Pharmaceutics, vol. 307, No. 1, pp. 93-102 (2006).
Patel et al., "A novel approach for antibody Nanocarriers development through hydrophobic ion-pairing complexation," Journal of Microencapsulation, vol. 31, No. 6, pp. 542-550 (2014).
Pattni et al., "New Developments in Liposomal Drug Delivery," Chemical Reviews, vol. 115, No. 19, p. 10938-10966 (2015).
Pham et al., "Micellar Solutions of Associative Triblock Copolymers: Entropic Attraction and Gas-Liquid Transition", Macromolecules, vol. 32, No. 9, pp. 2996-3005 (1999).
Pinkerton et al., "Formation of stable nanocarriers by in situ ion pairing during block-copolymer directed rapid precipitation," Molecular Pharmaceutics, vol. 10, No. 1, pp. 319-328 (2013).
Radler et al., "Structure of DNA-cationic liposome complexes: DNA intercalation in multilamellar membranes in distinct Interhelical packing regimes," Science, vol. 275, No. 5301, pp. 810-814 (1997).
Salentinig et al., "Self-Assembled Structures and pKa Value of Oleic Acid in Systems of Biological Relevance," Langmuir, vol. 26, No. 14, p. 11670-11679 (2010). DOI: 10.1021/la101012a.
Serajuddin, "Salt formation to improve drug solubility" Advanced Drug Delivery Reviews, vol. 59, No. 7, pp. 603-616 (2007).
Sohn et al., "Polymer prodrug approaches applied to paclitaxel," Polymer Chemistry, vol. 1, No. 6, pp. 778-792 (2010).
Song et al., "A novel in situ hydrophobic ion pairing (HIP) formulation strategy for clinical product selection of a hanoparticle drug delivery system," Journal of Controlled Release, vol. 229, pp. 106-119 (2016).
Tang et al., "An innovative method for preparation of hydrophobic ion-pairing colistin entrapped poly(lactic acid) hanoparticles: Loading and release mechanism study", European J. Pharmaceutical Sciences, vol. 102, pp. 63-70 (2017).
Turro et al., "Spectroscopic probe analysis of protein-surfactant interactions: the BSA/SDS system," Langmuir, vol. 11, No. 7, pp. 2525-2533 (1995).
U.S. Appl. No. 16/253,850 Notice of Allowance dated Sep. 13, 2022.
U.S. Appl. No. 16/761,140 Office Action dated Feb. 8, 2022.
U.S. Appl. No. 16/761,140 Office Action dated Aug. 26, 2022.
U.S. Appl. No. 16/761,140 Restriction Requirement dated Aug. 19, 2021.
U.S. Appl. No. 16/816,241 Office Action dated May 12, 2022.
Vyavahare et al., "Analysis of Structural Rearrangements of Poly(lactic acid) in the Presence of Water", The Journal of Physical Chemistry B, vol. 118, No. 15, pp. 4185-4193 (2014).
Yu et al., "Nanotechnology for Protein Delivery: Overview and Perspectives", J. Control. Release, vol. 240, pp. 24-37 (2016).
Zhang et al., "Development of Nanoparticles for Antimicrobial Drug Delivery" Current Medicinal Chemistry, vol. 17, No. 6, pp. 585-594 (2010).
Notice of Allowance dated Apr. 12, 2022 in U.S. Appl. No. 16/253,850.
Høiby, "Recent advances in the treatment of Pseudomonas aeruginosa infections in cystic fibrosis", BMC Medicine, vol. 9, No. 32, pp. 1-7 (2011).
Liu et al., "Ostwald ripening of beta-carotene nanoparticles", Phys. Rev. Lett., vol. 98, No. 3, pp. 036102-1-036102-4 (2007).
Ilton et al., "Direct Measurement of the Critical Pore Size in a Model Membrane", Physical Review Letters, vol. 117, Issue 25, p. 257801-1 through 257801-5, Dec. 2016.
U.S. Appl. No. 16/253,850 Supplemental Notice of Allowability dated Dec. 19, 2022.
U.S. Appl. No. 16/816,241 Notice of Allowance and Notice of Allowability dated Nov. 16, 2022.

* cited by examiner

METHOD FOR CONTROLLING ENCAPSULATION EFFICIENCY AND BURST RELEASE OF WATER SOLUBLE MOLECULES FROM NANOPARTICLES AND MICROPARTICLES PRODUCED BY INVERSE FLASH NANOPRECIPITATION

This application claims the benefit of U.S. Provisional Application No. 62/700,934, filed Jul. 20, 2018, the specification of which is hereby incorporated by reference in its entirety.

This invention was made with government support under Grant No. DGE-1148900 awarded by the National Science Foundation. The government has certain rights in the invention.

FIELD OF THE INVENTION

The present invention relates to the methods to control encapsulation efficiency and burst release of hydrophilic agents from nanoparticles and microparticles composed of primary nanoparticles which have a hydrophilic core. The present invention encompasses microparticles and nanoparticles composed of primary nanoparticles produced by Flash NanoPrecipitation (FNP) and inverse Flash NanoPrecipitation (iFNP).

BACKGROUND OF THE INVENTION

Encapsulation and delivery of soluble therapeutics and biologics including peptides, proteins, DNA, and RNA can be challenging. Biologics can suffer from poor stability, fast clearance times, immune recognition, and high costs. Biologics are most commonly delivered via injection, thus controlled release may reduce the frequency of drug administration and increase patient compliance.

The delivery of these species from polymeric systems falls into two categories: release from a monolith, or release from micro or nanoparticles. Monoliths include erodible implantable devices. Micro and nanoparticles may be delivered systemically or in a local depot. Microparticles are particles in the range of 1 to 100 microns in diameter. Nanoparticles are particles in the range of 40 to 600 nanometers in diameter. Diameters of nanoparticles can be assessed by dynamic light scattering using an instrument such as the Malvern Inc. Nanosizer, with the deconvolution accomplished using the Malvern software in the Normal Mode analysis. The size is given as the intensity weighted average. The sizes of microparticles can be assessed by SEM imaging and image analysis to determine the number average size.

SUMMARY

Water soluble molecules, also termed water soluble actives, including small molecules, peptides, and biologics can be encapsulated by amphiphilic polymers using a rapid and controlled precipitation process called inverse Flash NanoPrecipitation (iFNP) (see, International Patent Applications PCT/US2015/036060 (published as WO/2015/200054 on Dec. 30, 2015) and PCT/US2016/068145 (published as WO/2017/112828 on Jun. 29, 2017), which are hereby incorporated by reference in their entireties). Nanoparticles produced by iFNP include a hydrophilic core loaded with the water soluble molecules and a hydrophobic corona or shell (FIG. 1). The nanoparticles are dispersed in a nonpolar solvent. The stabilizing polymer may have an anionic region that becomes part of the hydrophilic nanoparticle core. The anionic region of the polymer can be ionically crosslinked with metal cations or amines. The primary nanoparticles can be coated with a second stabilizing block copolymer so that they can be dispersed in water (FIG. 2). This coating process results in particles that are still in the nano-scale size range. Alternatively, the primary particles can be aggregated into microparticles either through an oil-in-water emulsion process or by spray drying (FIG. 3). The resulting microparticles are different from those produced by traditional water-in-oil-in-water (W/O/W) or solid-in-oil-in-water (S/O/W) double emulsions because the inclusions of water soluble molecules are much finer, are better dispersed throughout the microparticle, and are each coated with a block copolymer layer.

The encapsulation efficiency (EE) within the nanoparticle or microparticles is the mass percentage of the water soluble material at the start of the formulation process that ends up in the final particles. Low EE means that most of the soluble material is lost during processing and does not end up in the final particle. Therefore, high EEs are generally preferred. The burst release is the percentage of the soluble encapsulate material that is released early during the use of the particle. The time period over which release is considered burst is related to the particle application. For the purposes of this disclosure, burst release from nanoparticles is considered the amount released in the first hour, and burst release from microparticles is considered the amount released in the first 24 to 48 hours.

Encapsulating water-soluble materials without chemical modification into a hydrophobic scaffold can involve (1) mixing the material directly with a scaffold material (example: PLGA (poly(lactic-co-glycolic acid)) in an organic solvent (solid-in-oil dispersion) or (2) making an aqueous solution of the water-soluble material and emulsifying this in an organic solvent containing the scaffold material (water-in-oil emulsion) [Pagels, R. F.; Prud'homme, R. K. Polymeric nanoparticles and microparticles for the delivery of peptides, biologics, and soluble therapeutics. *J. Controlled Release* 2015, 219, 519-535]. In either case (1) or (2), the solvent can be emulsified in an external aqueous phase (creating a solid-in-oil-in-water (S/O/W) emulsion in case (1) or a water-in-oil-in-water (W/O/W) emulsion in case (2)), and the solvent is then removed to formed hardened nanoparticles or microparticles of the scaffold material with the soluble material dispersed throughout. Alternatively, the particles can be produced by spray drying the dispersion without the need for an additional emulsification step. In these formulations, the long release (over days to weeks or months) is controlled by the properties of the scaffold material, the particle composition, and the particle structure. These particles can be difficult to manufacture reproducibly on a large scale.

For microparticles and nanoparticles produced by S/O/W or W/O/W emulsion methods, encapsulation efficiency and burst release are two major issues. Low encapsulation efficiency can be caused by losses to the external aqueous phase during the final emulsion and drying steps. Burst release early in the release profile is a more complicated phenomenon. A hypothesis is that the burst release is cause by the formation of cracks or pores in the particles during the drying process [Schwendeman, S. P.; Shah, R. B.; Bailey, B. A.; Schwendeman, A. S. Injectable controlled release depots for large molecules. *J. Controlled Release* 2014, 190, 240-253; Kang, J.; Schwendeman, S. P. Pore Closing and Opening in Biodegradable Polymers and Their Effect on the Controlled Release of Proteins. *Mol. Pharmaceutics* 2007, 4, 104-118; Wang, J.; Wang, B. A.; Schwendeman, S. P. Characterization of the initial burst release of a model peptide from poly(D,L-lactide-co-glycolide) microspheres. *J. Controlled Release* 2002, 82, 289-307; Pagels, R. F.; Prud'homme, R. K. Polymeric nanoparticles and microparticles for the delivery of peptides, biologics, and soluble therapeutics. *J. Controlled Release* 2015, 219, 519-535.]. The cracks and pores can allow encapsulated soluble material to be quickly released from within the particle. In "pore healing" the line tension of the pore causes the pore to close, shutting off the burst release (FIG. 4a). This pore healing requires the hydrophobic polymer scaffold to be mobile; increasing polymer mobility may decrease the burst release, for example, by using polymers with lower glass transition temperatures ($T_g$), using polymers with lower molecular weights, and measuring release at higher temperatures [U.S. Pat. No. 5,366,734A; Schwendeman, S. P.; Shah, R. B.; Bailey, B. A.; Schwendeman, A. S. Injectable controlled release depots for large molecules. *J. Controlled Release* 2014, 190, 240-253; Kang, J.; Schwendeman, S. P. Pore Closing and Opening in Biodegradable Polymers and Their Effect on the Controlled Release of Proteins. *Mol. Pharmaceutics* 2007, 4, 104-118; Wang, J.; Wang, B. A.; Schwendeman, S. P. Characterization of the initial burst release of a model peptide from poly(D,L-lactide-co-glycolide) microspheres. *J. Controlled Release* 2002, 82, 289-307; Shah, S.; Cha, Y.; Pitt, C. Poly(glycolic Acid-Co-Dl-Lactic Acid)—Diffusion Or Degradation Controlled Drug Delivery. *J. Controlled Release* 1992, 18, 261-2701 Pores in microparticles may be closed by annealing the particles above the hydrophobic polymer glass transition temperature [Reinhold, S. E.; Desai, K. H.; Zhang, L.; Olsen, K. F.; Schwendeman, S. P. Self-Healing Microencapsulation of Biomacromolecules without Organic Solvents. *Angew. Chem.-Int. Edit.* 2012, 51, 10800-10803.]. Alternatively, pore closing can be accelerated and burst release can be reduced by measuring release rates at temperatures higher than the glass transition temperature of the hydrophobic polymer [Kang, J.; Schwendeman, S. P. Pore Closing and Opening in Biodegradable Polymers and Their Effect on the Controlled Release of Proteins. *Mol. Pharmaceutics* 2007, 4, 104-118.] Burst release may be minimized by changing the method of particle drying. For example, Kim & Park showed that vacuum dried particles had less burst release than freeze dried particles, presumably because fewer pores and cracks were formed during the vacuum drying process [Kim, T.; Park, T. Critical effect of freezing/freeze-drying on sustained release of FITC-dextran encapsulated within PLGA microspheres. *Int. J. Pharm.* 2004, 271, 207-214.].

Inverse Flash NanoPrecipitation (iFNP) is a method to make "inverted" nanoparticles highly loaded with water soluble molecules (International Patent Applications PCT/US2015/036060 and PCT/US2016/068145). In a typical iFNP step, a polar process solvent containing hydrophilic material and an amphiphilic polymer or other stabilizer is rapidly mixed with a miscible non-polar non-process solvent (FIG. 1). Upon mixing, the hydrophilic material as well as the more polar regions of the stabilizer precipitate to form the nanoparticle core (FIG. 1). The less polar regions of the stabilizer form a shell around the nanoparticle core. These primary nanoparticles can be further stabilized through various methods including ionic crosslinking. For aqueous applications, the primary nanoparticles can be coated with a second stabilizer (when a nanoparticle is required for the final application) or aggregated into microparticles either by a nanoparticle-in-oil-in-water (N/O/W) emulsion or through spray drying.

These primary nanoparticles can be processed for use as nanoparticles by adding a second coating, or for use as microparticles by aggregating the primary nanoparticles.

The present invention encompasses methods to control the encapsulation efficiency and short-term burst release (over the period of 1 to 2 hours for nanoparticles and 1 to 2 days for microparticles) of water-soluble materials from nanoparticles and microparticles composed of inverted nanoparticles. Inverted nanoparticles are nanoparticles with a hydrophilic core and hydrophobic corona or shell. These nanoparticles can be produced through inverse Flash NanoPrecipitation (iFNP), as disclosed in PCT/US2015/036060, which is hereby incorporated by reference in its entirety. The inverted nanoparticles can be coated to form nanoparticles stable in aqueous phases or incorporated into microparticles or larger monoliths (see, PCT/US2015/036060 and PCT/US2016/068145). Encapsulation efficiency accounts for the loss of the soluble material to be encapsulated in the iFNP step as well as in subsequent processing steps. Burst release is the amount released early in the overall release profile. For nanoparticle applications, controlled release is typically required over a time period of multiple hours to days. Therefore, burst release from nanoparticles is considered the amount of encapsulated soluble material released on a time scale of minutes to one hour. Controlled release is typically required over a time period of days to weeks to months or even as long as a year from microparticles and larger monoliths. Therefore, for microparticle and monolith applications, burst release is considered the amount of encapsulated soluble material released on a timescale of hours to two days.

Encapsulation efficiency of soluble agents in nanoparticles and microparticles composed of primary nanoparticles produced by iFNP can by increased by (1) limiting the solubility of the encapsulated agent in the processing solvents, (2) crosslinking the primary nanoparticle core, (3) the presence of favorable interactions between the encapsulated material and the stabilizing polymer, (4) increasing the length of the hydrophobic portion of the stabilizer, (5) lowering the processing temperature, (6) increasing the osmotic strength of the final aqueous processing phase, and (7) adding small molecule or polymeric bulking agents that bulk the hydrophobic portion to the final nanoparticle or microparticle.

Burst release of soluble agents in nanoparticles and microparticles composed of primary nanoparticles produced by iFNP can be reduced by (1) decreasing the release temperature, (2) crosslinking the primary nanoparticle core, (3) adding small molecule or polymeric bulking agents that bulk the hydrophobic shell to the final nanoparticle or microparticle, and (4) increasing the glass transition temperature ($T_g$) of the hydrophobic phase of the final nanoparticles or microparticles.

The contents of this disclosure are new and unexpected. The burst release of soluble agents from particles produced by traditional S/O/W or W/O/W emulsions can be reduced by increasing release temperature, decreasing the hydrophobic polymer $T_g$, or changing the particle drying method for particles produced. However, for particles produced by iFNP, low release temperatures and high polymer $T_g$ may be preferred for applications that require low burst release.

Adding bulking agents and ionically crosslinking the primary nanoparticle core can also decrease burst release, though these variables do not have counterparts in the S/O/W or W/O/W emulsion processes. Shown herein is a null result in which the particle drying method has little effect on the burst release. Also shown is a result in which annealing the particles at elevated temperatures makes the burst release higher instead of lower, in contradiction of the behavior observed in particles made through traditional methods. Though these unexpected results are not limited to or by this mechanism, and without being bound be theory, without bulking agents, pore opening may occur above the $T_g$ of the hydrophobic materials (FIG. 4b). In thin films, there is a critical pore diameter below which pore closing occurs and above which pore opening occurs. The critical pore diameter is related to the thickness of the thin film [Ilton, M.; DiMaria, C.; Dalnoki-Veress, K. Direct Measurement of the Critical Pore Size in a Model Membrane. *Phys. Rev. Lett.* 2016, 117, 257801.]. Not limited to this mechanism, and without being bound by theory, the critical pore size in nanoparticles and microparticles produced by iFNP may be very small due to thinness of the polymer layer coating the particles. Therefore, in particles produced by iFNP, above the polymer $T_g$ pore opening occurs resulting in greater levels of burst release. Adding bulking agents increases the polymer layer thickness and decreases the critical pore size, allowing pore closing to occur at temperature above the polymer $T_g$ causing the particles to behave more similarly to those produced by S/O/W or W/O/W emulsions. Without bulking agents, low temperatures or materials with high $T_g$ prevent structural relaxation and decrease the amount of burst release.

In a method according to the invention, a polymer inverse nanoparticle that encapsulates a water soluble active to maximize or optimize encapsulation efficiency and/or to minimize and/or optimize burst fraction is formed by dissolving the water soluble active at a concentration and a block copolymer at a concentration in an amount of a process solvent to form a process solution and continuously mixing the process solution with an amount of a nonprocess solvent at a process temperature to form a first nanoparticle solution comprising polymer inverse nanoparticles having a core and a shell and a first nanoparticle solvent. The block copolymer can include a hydrophilic block and a hydrophobic block having a glass transition temperature (Tg). The hydrophilic block can be soluble in the process solvent and can be insoluble in the nonprocess solvent. The hydrophobic block can be insoluble in the process solvent and can be soluble in the nonprocess solvent. The process solution can be more polar than the nonprocess solvent. The water soluble active and the hydrophilic block can be in the core and the hydrophobic block can be in the shell.

The encapsulation efficiency can be maximized or optimized by one or several of the following: (a) selecting the process solvent, so that the hydrophilic block is close to a solubility limit in the process solution for the concentration of the block copolymer; (b) crosslinking the hydrophilic block in the core; (c) selecting the hydrophilic block to have bonding interactions with the water soluble active in the core; (d) selecting the hydrophobic block to have a molecular weight of at least 10 kDa, 20 kDa, 30 kDa, 40 kDa, 50 kDa, 70 kDa, or 100 kDa; (e) selecting the process temperature and/or the hydrophobic block, so that the process temperature is less than the hydrophobic block glass transition temperature (Tg); (f) selecting the process solvent to have high osmolarity (e.g., by dissolving a salt in the process solvent); and/or (g) adding a supplemental hydrophobic compound to the process solvent and/or to the nonprocess solvent to increase the bulk of hydrophobic material in the shell.

The burst fraction can be minimized or optimized by one or several of the following: (aa) crosslinking the hydrophilic block in the core; (bb) increasing the hydrophobic block glass transition temperature (Tg); and/or (cc) adding a supplemental hydrophobic compound to the process solvent and/or to the nonprocess solvent to increase the bulk of hydrophobic material in the shell.

The encapsulation efficiency can be optimized by crosslinking the hydrophilic block in the core. The burst fraction can be minimized by crosslinking the hydrophilic block in the core. The crosslinking agent can be a metal or calcium. The crosslinking agent can be a chelating agent or tetraethylene pentamine (TEPA).

The encapsulation efficiency can be maximized by adding a supplemental hydrophobic compound to the nonprocess solvent to increase the bulk of hydrophobic material in the shell. The burst fraction can be minimized by adding a supplemental hydrophobic compound to the nonprocess solvent to increase the bulk of hydrophobic material in the shell. The supplemental hydrophobic compound can be a hydrophobic polymer or polylactic acid. The supplemental hydrophobic compound can be vitamin E.

The burst fraction can be minimized by selecting the process temperature and/or the hydrophobic block, so that the process temperature is less than the hydrophobic block glass transition temperature (Tg).

The method can further include annealing the polymer inverse nanoparticle. The annealing can maximize the encapsulation efficiency. The annealing can optimize the encapsulation efficiency.

Lecithin can be added to the nonprocess solvent.

The water soluble active can be ovalbumin, lysozyme, and/or PEP1. The water soluble active can be vancomycin. The water soluble active can be a linear polypeptide or a cyclic polypeptide.

The hydrophilic block can be poly(aspartic acid) and/or poly(glutamic acid). The hydrophobic block can be poly(lactic acid), poly(lactic-co-glycolic acid), and/or poly(caprolactone). The hydrophilic block can have a molecular weight in the range of from 0.2 kDa to 100 kDa, from 0.5 kDa to 50 kDa, from 1 kDa to 20 kDa, from 2 kDa to 10 kDa, or of about 5 kDa. The hydrophobic block can have a molecular weight in the range of from 0.5 kDa to 400 kDa, 1 kDa to 200 kDa, from 2 kDa to 100 kDa, from 5 kDa to 100 kDa, from 10 kDa to 40 kDa, of about 10 kDa, of about 20 kDa, or of about 40 kDa.

The supplemental hydrophobic compound can be poly(lactic acid), poly(lactic-co-glycolic acid), and/or poly(caprolactone).

The process solvent can be miscible with the nonprocess solvent.

The method can further include adding a second block copolymer to the first nanoparticle solution to form a second stage process solution and continuously mixing the second stage process solution with a finishing solvent to form a second nanoparticle solution comprising the polymer inverse nanoparticles coated with the second block copolymer. The second block copolymer can include a second hydrophilic block and a second hydrophobic block. The second hydrophilic block can be poly(ethylene glycol) and/or poly(propylene oxide). The second hydrophobic block can be poly(lactic acid), poly(lactic-co-glycolic acid), and/or poly(caprolactone). The second hydrophilic block can have a molecular weight in the range of from 0.2 kDa to 100 kDa, from 0.5 kDa to 50 kDa, from 1 kDa to 20 kDa, from 2 kDa to 10 kDa, or of about 5 kDa. The second hydrophobic block can have a molecular weight in the range of from 0.2 kDa to 100 kDa, from 0.5 kDa to 50 kDa, from 1 kDa to 20 kDa, from 2 kDa to 10 kDa, or of about 5 kDa. The second stage process solution can be miscible with the finishing solvent.

The method can further include concentrating the polymer inverse nanoparticles to form microparticles. Each microparticle can include a plurality of nanoparticles.

The water soluble active can be anionic and the hydrophilic block can be selected to be cationic, so that water soluble active and the hydrophilic block ionically bond. The water soluble active can be cationic and the hydrophilic block can be selected to be anionic, so that water soluble active and the hydrophilic block ionically bond.

The method can further include adding a tackifier to the process solvent and/or to the nonprocess solvent to increase the hydrophobic block glass transition temperature (Tg).

The process solvent and the finishing solvent can be each independently selected as dimethylsulfoxide (DMSO), propanol, ethanol, methanol, and/or water. The nonprocess solvent can be dichloromethane, chloroform, acetone, tetrahydrofuran (THF), and/or methanol.

The continuous mixing can be through a flash nanoprecipitation process.

In an embodiment according to the invention, a polymer inverse nanoparticle that encapsulates a water soluble active includes a triblock copolymer comprising two hydrophilic end blocks and a hydrophobic center block, a core, and a shell. The hydrophobic center block can be between each of the two hydrophilic end blocks. The water soluble active and the hydrophilic end blocks can be within the core. The hydrophobic center block can be within the shell. The hydrophilic end blocks can be crosslinked within the core with a crosslinking agent.

The hydrophobic end blocks can be formed from the same monomer (i.e., the hydrophobic end blocks can be chemically identical). The water soluble active can be a cyclic polypeptide. The water soluble active can be ovalbumin, lysozyme, and/or PEP1. The water soluble active can be vancomycin. Each hydrophilic end block can be independently selected from poly(aspartic acid) and/or poly(glutamic acid). The hydrophobic center block can be poly(lactic acid), poly(lactic-co-glycolic acid), and/or poly(caprolactone). The triblock copolymer can be poly(aspartic acid)-b-poly(lactic acid)-b-poly(aspartic acid). The triblock copolymer can be poly(glutamic acid)-b-poly(lactic acid)-b-poly(glutamic acid). The triblock copolymer can be poly(aspartic acid)-b-poly(lactic-co-glycolic acid)-b-poly(aspartic acid). The triblock copolymer can be poly(glutamic acid)-b-poly(lactic-co-glycolic acid)-b-poly(glutamic acid).

The polymer inverse nanoparticle can further include a diblock copolymer including a hydrophilic block and a hydrophobic block, and a coating including an interior layer and an exterior layer. The hydrophobic block can be within the interior layer; the hydrophilic block can be within the exterior layer; and the interior layer can be adjacent to the shell. The hydrophilic block can be polyethylene glycol (PEG). The hydrophobic block can be polylactic acid (PLA).

DETAILED DESCRIPTION

Figure 1:
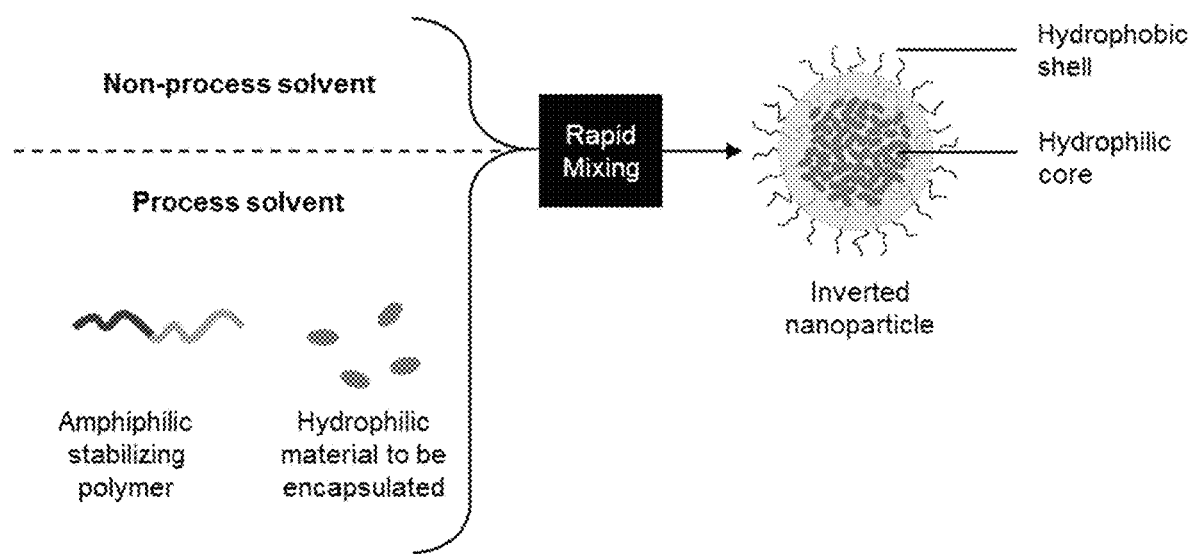
FIG. 1 illustrates the precipitation process used to produce the inverted nanoparticle. The inverted nanoparticle has a hydrophilic core and a hydrophobic shell.
Figure 2:
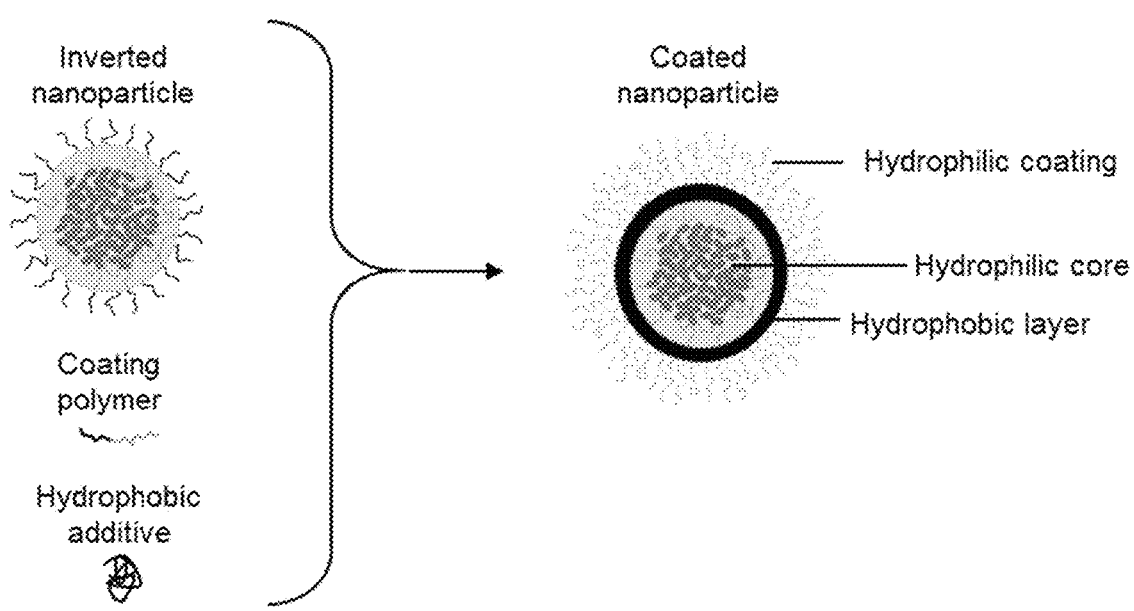
FIG. 2 illustrates the materials used to coat the inverted nanoparticles, and the final structure of the final coated nanoparticle.
Figure 3:
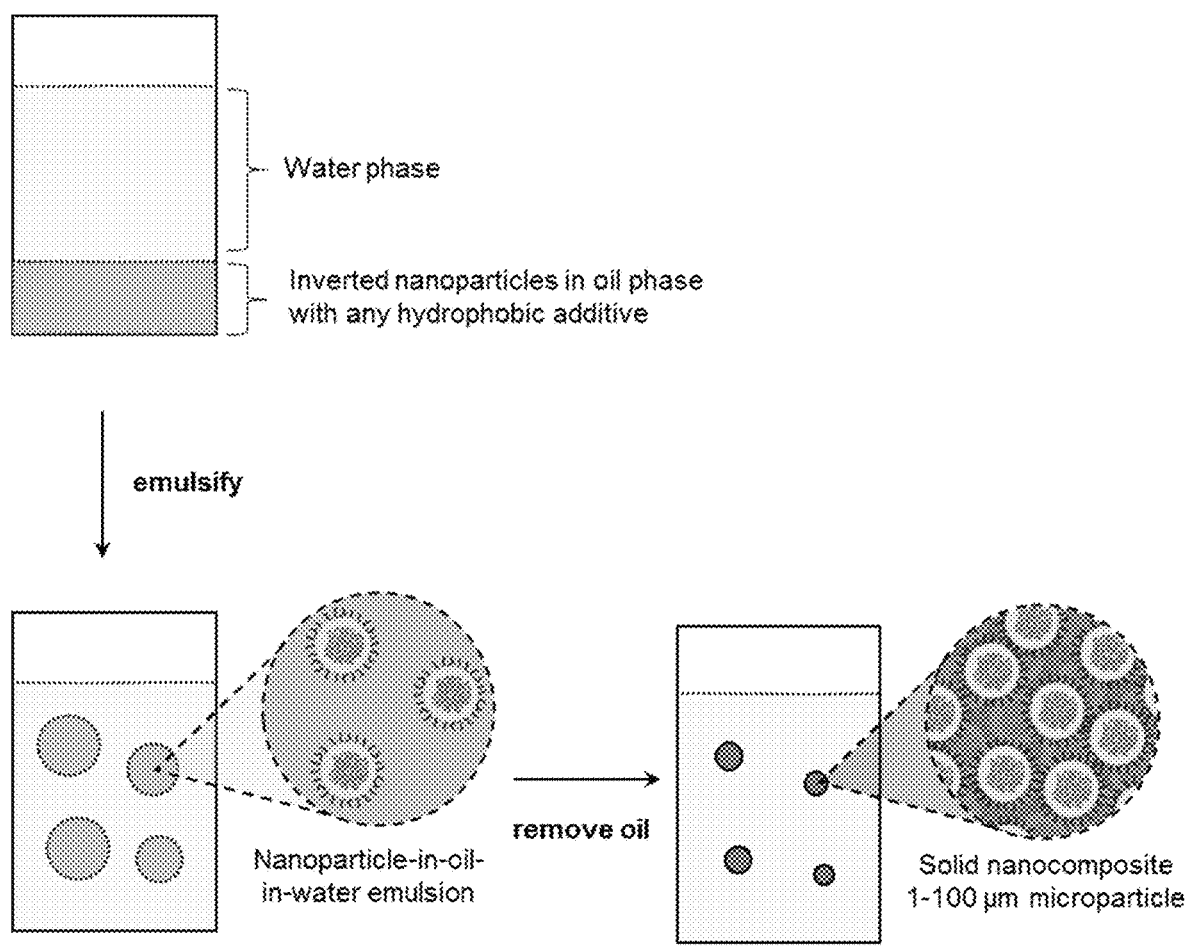
FIG. 3 illustrates one method that may be used to produce microparticles from the inverted nanoparticles. The nanoparticles and any hydrophobic additives in an oil phase are emulsified in water, and the oil is removed to produce hardened microparticles.
Figure 4A:
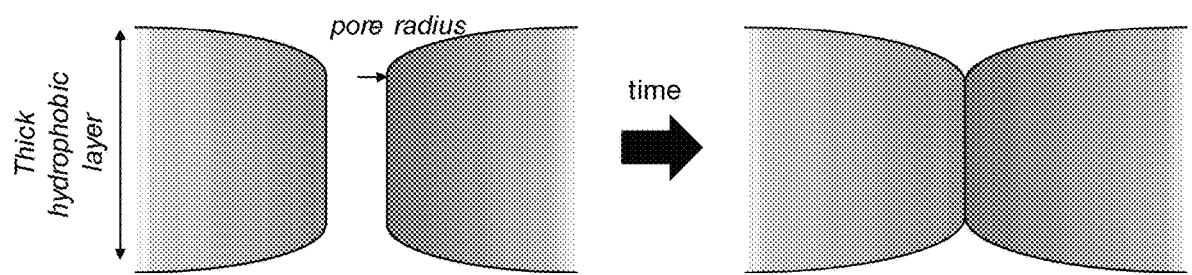
FIG. 4A shows the pore closing process, when the pore radius is less than the critical pore radius (i.e., a thick hydrophobic layer) at temperatures above the gl
Figure 4B:
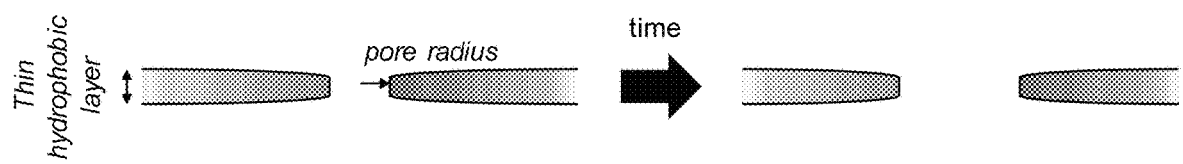

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference in their entirety as if each had been individually incorporated.

Described herein is a method for controlling the encapsulation efficiency and burst release of water soluble molecules from nanoparticle and microparticle formulations produced by the inverted Flash NanoPrecipitation (iFNP) process and subsequent processing steps. The iFNP method and processing steps are described in International Applications PCT/US2015/036060 and PCT/US2016/068145. How the processing steps and materials used can be adjusted to tune the encapsulation efficiency and burst release of the encapsulated water-soluble material is described herein. In the iFNP process, water soluble molecules—including peptides, proteins, DNA, RNA, non-biologic therapeutics, and imaging agents—precipitate into nanoparticles that are protected by a copolymer stabilizing agent. These particles can be covalently or non-covalently stabilized. The particles can be coated with an amphiphilic copolymer, or processed into microparticles or larger monoliths. For example, herein is set forth how the encapsulation efficiency of the soluble agent in the particles as well as the burst release of the soluble agent from the particles can be controlled by: (1) the copolymers used in the assembly or coating process, (2) the degree of crosslinking of the nanoparticle core, (3) the incorporation of small molecule or polymeric additives, and/or (4) the processing and release conditions employed.

Inverse Flash NanoPrecipitation Process

Core-shell nanoparticles are formed by a rapid, single-step, copolymer-directed precipitation process, previously described by Johnson et al. termed "Flash NanoPrecipitation" (FNP) (see, Johnson, B. K., et al., AIChE Journal (2003) 49:2264-2282 and U.S. Pat. No. 8,137,699, which are hereby incorporated by reference in their entirety). This process can be "inverted" (see, PCT/US2015/036060). In the application of this method to create inverted nanoparticles with hydrophilic cores and/or with encapsulated water soluble agents, a copolymer is dissolved in a polar process solvent at a concentration of at least 0.1% by weight, but the concentration of copolymer can be at least 0.2% by weight. Examples of copolymers include but are not limited to block copolymers, graft copolymers, and random copolymers that contain regions with different solvent solubilities within the same copolymer. Examples of process solvents include, but are not limited to, water, alcohols, acetone, acetonitrile, dimethyl sulfoxide (DMSO), dimethylformamide (DMF), and mixtures thereof. The process solvent can be heated or pressurized or both to facilitate dissolution of the copolymer, depending on the dissolution characteristics of the copolymer in the solvent. Upon micromixing the process solvent containing the copolymer with a less polar non-process solvent, the dissimilar solubility characteristics of the copolymer manifest themselves and the more polar portions of the copolymer can no longer exist in the soluble state, and thus precipitate.

In one embodiment of the present invention, additive water soluble target molecules can be added to the copolymer in the process solvent. Upon creation of inverted nanoparticles with the copolymer, the additive target molecule are incorporated in the nanoparticle. Additive target molecules that are poorly soluble in the non-process solvent are coated, encapsulated, or confined as a particulate core and sterically stabilized by the protective colloid of the copolymer. The inverted nanoparticles maintain a small and stable size in the non-process solvent.

In one embodiment of the present invention, the target material and copolymer are dissolved in separate process solvent streams. The process solvent used to dissolve the copolymer and target material may be, but are not required to be, the same. These streams are simultaneously mixed with the non-process solvent. In another embodiment of the present invention, the target material and copolymer are dissolved in a single process solvent stream. This stream is then rapidly mixed with a non-process solvent.

In one embodiment of the invention a stabilizing material, described later, is included in the process solvent. In another embodiment of the invention a stabilizing material is included in the non-process solvent.

The intense micromixing can be effected in any number of geometries. The essential idea is that high velocity inlet streams cause turbulent flow and mixing that occurs in a central cavity. The time for process solvent/non-process solvent mixing is more rapid than the assembly time of the nanoparticles. While not meant to be limiting, two such geometries have been previously described and analyzed: the Confined Impinging Jet mixer (CIJ) [Johnson, B. K.; Prud'homme, R. K. Chemical processing and micromixing in confined impinging jets. *AIChE Journal* 2003, 49, 2264-2282; Liu, Y.; Fox, R. O. CFD predictions for chemical processing in a confined impinging-jets reactor. *AIChE Journal* 2006, 52, 731-744.] or a multi-inlet vortex mixer (MIVM) [Liu, Y.; Cheng, C.; Liu, Y.; Prud'homme, R. K.; Fox, R. O. Mixing in a multi-inlet vortex mixer (MIVM) for flash nano-precipitation. *Chemical Engineering Science* 2008, 63, 2829-2842]. These examples are meant to be illustrative rather than limiting or exhaustive.

The fast mixing and high energy dissipation involved in this process provide mixing timescales that are shorter than the timescale for nucleation and growth of particles, which leads to the formation of nanoparticles with active agent loading contents and size distributions not provided by other technologies. When forming the nanoparticles via inverse Flash NanoPrecipitation, mixing occurs fast enough to allow high supersaturation levels (as high as 10,000) of all components to be reached prior to the onset of aggregation. The timescale of aggregation of the target material and copolymer self-assembly are balanced. Therefore, the target material and polymers precipitate simultaneously, and overcome the limitations of low active agent incorporations and aggregation found with the widely used techniques based on slow solvent exchange (e.g., dialysis). The inverse Flash NanoPrecipitation process is insensitive to the chemical specificity of the components, making it a universal nanoparticle formation technique.

The size of the resulting inverted nanoparticles from this process can be controlled by controlling the mixing velocity used to create them, the total mass concentration of the copolymer and target molecules in the process solvent, the process and non-process solvents, the ratio of the copolymer and target molecule, and the supersaturation of the target molecule and non-soluble portion of the copolymer upon mixing with the non-process solvent. Inverted nanoparticles can be produced from copolymers that are dissolved in a process solvent with no target material added.

Encapsulated Material

Encapsulated material must be sufficiently polar that it rapidly precipitates in the less polar non-process solvent. Molecules that do not meet these criteria may be chemically modified to increase their water solubility and propensity to precipitate in the organic non-process solvent. Examples of biologic material that may be encapsulated include, but are not limited to, peptides, proteins, DNA, RNA, saccharides, and derivatives, conjugates, and/or analogs thereof. Small molecule water soluble therapeutics and imaging agents may also be encapsulated. Soluble stabilizing agents may be encapsulated in particles to provide stability to the particle for its use or for subsequent processing steps. Any of these materials may also be co-precipitated within a single particle. Hydrophilic material may be encapsulated for the sole purpose of adding stability to the particles during post processing.

Material with molecular weights between 100 and 10,000,000 daltons may be encapsulated. Material with molecular weights between 250 and 10,000,000 daltons may be encapsulated. Material with molecular weights between 100 and 1,000,000 daltons may be encapsulated. Material with molecular weights between 250 and 1,000,000 daltons may be encapsulated. Material with molecular weights between 100 and 200,000 daltons may be encapsulated.

For example, the water soluble active can have a molecular weight of from about 100 Da, 200 Da, 500 Da, 1000 Da, 2000 Da, 5000 Da, 10000 Da, 20000 Da, and 40000 Da to about 1000 Da, 2000 Da, 5000 Da, 10000 Da, 20000 Da, 40000 Da, 100 kDa, 200 kDa, 500 kDa, and 1000 kDa.

Solvents

Formation of inverted nanoparticles requires a process solvent and non-process solvent stream. The process and non-process solvents each may be a pure liquid compound or a mixture of two or pure liquid compounds. Other non-liquid compounds that aid in the solvent quality of the streams but do not end up in the final nanoparticle construct may be added and are also considered part of the solvent.

The process solvent containing the copolymer is chosen, so that the copolymer is molecularly dissolved. This requires that the process solvent solubilize all parts of the copolymer.

The process solvent containing the material to be encapsulated, if present, is also chosen such that material is molecularly dissolved. These process solvents may be, but are not required to be, the same. In some cases, both the copolymer and material to be encapsulated may be dissolved in a single solution of the process solvent. In order to dissolve the water soluble material to be encapsulated, the process solvent is more polar than the non-process solvent. Examples of process solvents include, but are not limited to, water, alcohols, dimethyl formamide, dimethyl sulfoxide, acetonitrile, acetone, and mixtures thereof. Acids, bases, and salts are a few examples of additives that may be used to aid in the solubilization of the copolymer and encapsulated material in the process solvent.

The solutions of process solvent containing copolymer and material to be encapsulated is mixed with a non-process solvent. The non-process solvent must be capable of changing the local molecular environment of the copolymer and cause local precipitation of the less polar sections of the polymer. The non-process solvent is chosen such that the more polar sections of the copolymer rapidly precipitate and the more non-polar sections of the copolymer remain solubilized. Thus, the copolymer will self-assemble into micelles or other structures in the non-process solvent. The non-process solvent is chosen such that the target material to be encapsulated rapidly precipitates in the final mixture. The process and non-process solvents may be fully miscible at the final composition. In some cases, no more than 20 volume percent of the process solvent may phase separate in the final composition. This is acceptable if the phase separated solvent goes to the core of the particles and there is no macroscopic separation. Non-process solvents include, but are not limited to, chloroform, dichloromethane, alkanes such as hexane, ethers such as diethyl ether, tetrahydrofuran (THF), toluene, acetone, and mixtures thereof. Acids, bases, and salts are a few examples of additives that may be used to aid in the precipitation of the encapsulated material and sections of the copolymer. Solvent choices are made based on the solubilities of the copolymer and encapsulated materials. Process solvents of one system may work well as the non-process solvent in another system, thus the examples given above for process and non-process solvents should not be considered distinct.

The encapsulation efficiency may depend on the proper choice of non-process solvent. The lower the solubility of the encapsulated material in the non-process solvent, the higher the encapsulation efficiency.

Copolymers

The stabilizing polymer may be a copolymer of a more polar block coupled with a more non-polar block. The copolymer may be amphiphilic (the more non-polar block is not water soluble); however, this is not a requirement and copolymers may be fully water soluble or fully non-water soluble, as long as solubilities of the blocks differ significantly enough in the non-process solvent. The copolymer should self-assemble in the non-process solvent, with the more polar blocks precipitating and the more non-polar blocks remaining soluble. When used in the FNP process to make particles, the more polar blocks go to the core of the particle, and the more non-polar blocks form a sterically protective shell. The sterically protective shell prevents particle aggregation and prevents percolation of encapsulated material during post processing steps.

Nanoparticles formed by the process of this invention can be formed with graft, block or random copolymers. For example, these copolymers can have a molecular weight between 1000 g/mole and 1,000,000 g/mole, between about 3000 g/mole to about 25,000 g/mole, or at least 2000 g/mole.

The copolymers are comprised of repeat units or blocks that have different solubility characteristics. Typically, these repeat units are in groups of at least two comprising a block of a given character. Depending on the method of synthesis, these blocks could be of all the same repeat unit or contain different repeat units dispersed throughout the block, but still yielding blocks of the copolymer with polar and more non-polar portions. These blocks can be arranged into a series of two blocks (diblock) or three block (triblock), or more, forming the backbone of a block copolymer. In addition, the polymer chain can have chemical moieties covalently attached or grafted to the backbone. Such polymers are graft polymers. Block units making up the copolymer can occur in regular intervals or they can occur randomly making a random copolymer. In addition, grafted side chains can occur at regular intervals along the polymer backbone or randomly making a randomly grafted copolymer. In graft polymers, polar blocks may be grafted on a non-polar polymer. Non-polar blocks may be grafted on a more polar polymer chain. In graft copolymers, the length of a grafted moiety can vary. The grafted segments may be equivalent to 2 to 9 ethylene units in length. In addition, the grafting of the polymer backbone may be useful to enhance solvation or nanoparticle stabilization properties.

The copolymer used in this invention may be comprised of blocks of at least two repeat units or with a minimum contour length the equivalent of at least 5 ethylene units. Contour lengths are the linear sum of the polymer backbone, the molecular dimensions of which can be approximated using the Polymer Handbook, 4th Edition, eds. J. Brandrup, E. H. Immergut, and E. A. Grulke, assoc. ed. A. Abe, D. R. Bloch, 1999, New York, John Wiley & Sons, the disclosure of which is hereby incorporated by reference in its entirety.

Examples of suitable non-polar blocks in a copolymer include but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, vinyl phenols and vinyllimidazole; aminoalkyls including aminoalkylacrylates, aminoalkylsmethacrylates, and aminoalkyl(meth)acrylamides; styrenes; cellulose acetate phthalate, cellulose acetate succinate, hydroxypropylmethylcellulose phthalate, poly(D,L lactide), poly (D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., it al., Advanced Drug Delivery Reviews (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anyhydride copolymers of vinyl methylether and other vinyl ethers, polyamides (nylon 6,6), polyurethane, poly(ester urethanes), poly(ether urethanes), poly(ester-urea).

Examples of polymeric blocks include poly(ethylenevinyl acetate), poly (D,L-lactic acid) oligomers and polymers, poly(L-lactic acid) oligomers and polymers, poly(glycolic acid), copolymers of lactic acid and glycolic acid, poly (caprolactone), poly(valerolactone), polyanhydrides, copolymers of poly(caprolactone) or poly(lactic acid) For non-biologically related applications polymeric blocks that can be used include polystyrene, polyacrylates, and polybutadienes.

Natural products with sufficient hydrophobicity to act as the non-polar portion of the polymer include: hydrophobic vitamins (for example vitamin E, vitamin K, and A), carotenoids and retinols (for example beta carotene, astaxanthin, trans and cis retinal, retinoic acid, folic acid, dihydrofolate, retinylacetate, retinyl palmintate), cholecalciferol, calcitriol, hydroxycholecalciferol, ergocalciferol, alpha-tocopherol, alpha-tocopherol acetate, alpha-tocopherol nicotinate, and estradiol. For example, vitamin E can be used, and can be readily obtained as a vitamin E succinate, which facilitates functionalization to amines and hyroxyls on the active species.

Examples of suitable polar blocks in an amphiphilic copolymer include but are not limited to the following: carboxylic acids including acrylic acid, methacrylic acid, itaconic acid, and maleic acid; polyoxyethylenes or poly ethylene oxide; polyacrylamides and copolymers thereof with dimethylaminoethylmethacrylate, diallyldimethylammonium chloride, vinylbenzylthrimethylammonium chloride, acrylic acid, methacrylic acid, 2-crrylamideo-2-methylpropane sulfonic acid and styrene sulfonate, polyvincyl pyrrolidone, starches and starch derivatives, dextran and dextran derivatives; polypeptides, such as polylysines, polyarginines, polyglutamic acids; poly hyaluronic acids, alginic acids, polylactides, polyethyleneimines, polyionenes, polyacrylic acids, and polyiminocarboxylates, gelatin, and unsaturated ethylenic mono or dicarboxylic acids. To prepare anionic copolymers acrylic acid and methacrylic acid and poly aspartic acid polymers can be used. And to produce cationic copolymers DMAEMA (dimethylaminoethylmethacrylate), polyvinyl pyridine (PVP) or dimethylaminoethylacrylamide (DMAMAM). A listing of suitable polar, water soluble, polymers can be found in Handbook of Water-Soluble Gums and Resins, R. Davidson, McGraw-Hill (1980).

The lists above of non-polar and polar polymers should not be considered exclusive of one another. Copolymers of two polymers given in a single list may have sufficient differences in solubilities in a given non-process solvent to be used in this process. In an illustrative example, poly (ethylene oxide) and poly(acrylic acid) are both given in the list of polar polymers. However, poly ethylene oxide is soluble in chloroform and acetone, while poly acrylic acid is not. Therefore, copolymers of poly ethylene oxide and poly acrylic acid may be used in this process with chloroform or acetone as the non-process solvent.

Interactions between the stabilizing polymer and the encapsulated material can affect encapsulation efficiency and burst release. Interactions can be physical or ionic. For example, if the encapsulated material is cationic in nature, a stabilizing polymer with anionic regions will result in higher encapsulation efficiency and less burst release than a fully neutral polymer or polymer with cationic regions. Alternatively, if the encapsulated material is anionic in nature, a stabilizing polymer with cationic regions will result in higher encapsulation efficiency and less burst release than a fully neutral polymer or polymer with anionic regions. Another illustrative example is, if a polymer with anionic regions is used as a stabilizer, higher encapsulation efficiencies and lower burst release will be achieved for cation encapsulated materials than for neutral or anionic encapsulated materials.

Figure 5A:
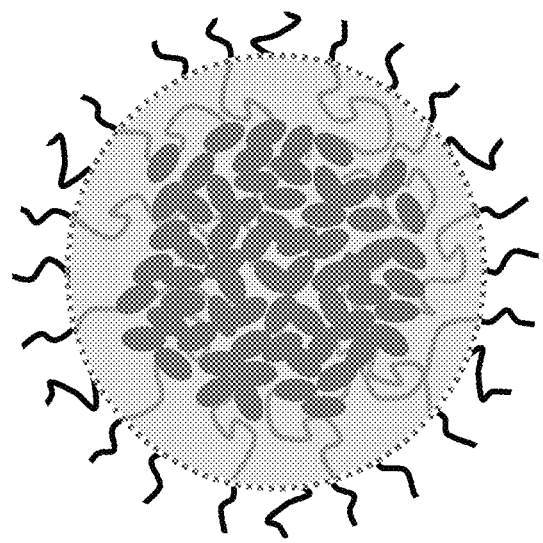
Figure 5B:
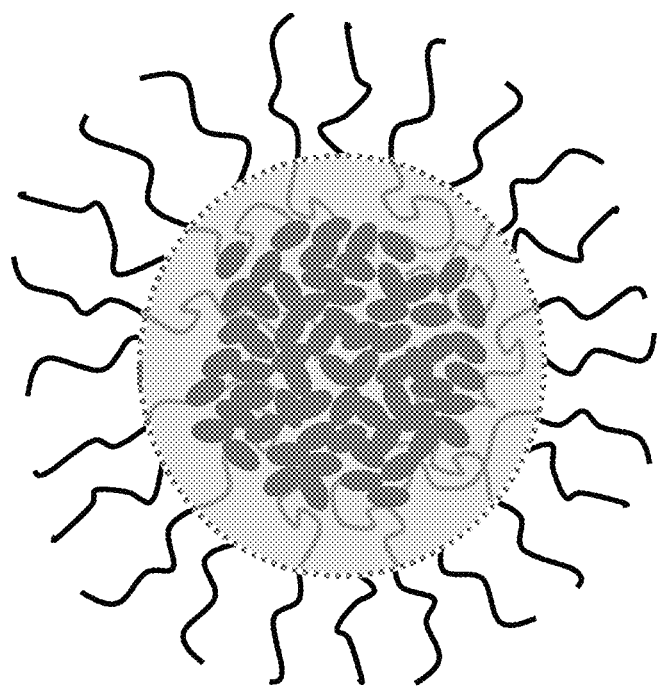

The properties of the hydrophobic blocks of the stabilizing polymer can control the encapsulation efficiency and burst release from the final microparticles or nanoparticles. For most applications, higher molecular weight hydrophobic blocks in the stabilizing polymer will result in higher encapsulation efficiencies and lower burst release. For example, a stabilizing polymer containing a 20 kDa hydrophobic block will result in a higher encapsulation efficiency and lower burst release than a polymer containing a 5 kDa hydrophobic block. In general, there are diminishing returns at higher molecular weights. For example, a 20 kDa hydrophobic block will provide a higher encapsulation efficiency than a 5 kDa hydrophobic block; however, 100 kDa and 400 kDa hydrophobic blocks may result in similar encapsulation efficiencies. Without being bound by theory, a hypothesized mechanism for this result is that larger hydrophobic blocks create a thicker steric barrier around the nanoparticle core which prevents losses of encapsulated materials to external aqueous phases (FIG. 5). Another proposed mechanism described earlier is the pore-opening phenomenon which occurs when the pore diameter is greater than a critical pore diameter. The critical pore diameter is related to the film thickness. Therefore, though not dependent on this mechanism, higher molecular weight hydrophobic blocks result in thicker polymer films, thus increasing the critical pore diameter and limiting the amount of pore opening.

For encapsulation efficiencies of water-soluble materials greater than 50%, the hydrophobic block of the stabilizing polymer should be greater than 5 kDa. For encapsulation efficiencies of water-soluble materials greater than 60%, the hydrophobic stabilizing block of the polymer should be greater than 10 kDa. For encapsulation efficiencies of water-soluble materials greater than 70%, the hydrophobic block of the stabilizing polymer should be greater than 20 kDa. For high encapsulation efficiencies of water-soluble materials, the hydrophobic block of the stabilizing polymer should be between 4.5 and 200 kDa. For high encapsulation efficiencies (>50%, >60%, >70%, >80%, or >90%) of water-soluble materials, the hydrophobic block of the stabilizing polymer should be between 10 and 200 kDa. For high encapsulation efficiencies (>50%, >60%, >70%, >80%, or >90%) of water-soluble materials, the hydrophobic block of the stabilizing polymer should be between 20 and 200 kDa. For high encapsulation efficiencies (>50%, >60%, >70%, >80%, or >90%) of water-soluble materials, the hydrophobic block of the stabilizing polymer should be greater than 10 kDa.

The glass transition temperature of the hydrophobic block can impact the encapsulation efficiency and burst release from the final microparticles or nanoparticles. Hydrophobic polymer blocks with higher glass transition temperatures will result in higher encapsulation efficiencies and lower burst release. The effect of the glass transition temperature is dependent on the processing and release temperature. For example, all else the same, two hydrophobic blocks with different glass transition temperatures, but both with glass transition temperatures below the processing and release temperature will result in similar encapsulation efficiencies and burst release. Similarly, all else the same, two hydrophobic blocks with different glass transition temperatures but both with glass transition temperatures above the processing and release temperature will result in similar encapsulation efficiencies and burst release. Alternatively, all else the same, given two hydrophobic blocks with different glass transition temperatures—one above the processing and release temperature and one below the processing and release temperature—the polymer with the higher glass transition temperature would be expected to have a higher encapsulation efficiency and lower burst release.

Though not dependent on this mechanism, the proposed mechanism is that pore opening occurs for sufficiently thin polymer layers and results in lower encapsulation efficiency and greater burst release; however, this pore-opening process requires that the polymer thin film can relax (i.e., the temperature is above the glass transition temperature). A similar result can be obtained with crystalline polymers, for which the significant temperature is the crystal melting point. Crystalline hydrophobic polymer blocks with crystal melting temperatures greater than the processing and release temperatures can result in higher encapsulation efficiencies and lower burst release provided that the crystallization of the hydrophobic polymer does not negatively impact the particle structure. An example of a crystalline hydrophobic block is poly(ε-caprolactone).

It should be noted that the glass transition temperature of polymers can be modified through the addition of plasticizers (decrease glass transition temperature) and tackifiers (increase glass transition temperature). Residual solvents, including water, can also impact the polymer glass transition temperature. The glass transition temperature of the hydrophobic polymer block should be considered in the context of any additives including plasticizers, as well as any absorbed solvents including water. The glass transition temperature of the hydrophobic block of the stabilizing polymer can be measured by differential scanning calorimetry (DSC). The DSC samples should include any additional hydrophobic molecules or residual solvents contained in the particle formulation, as these may change the glass transition temperature of the hydrophobic polymer.

For applications in which bulking agents are not employed, the glass transition temperature of the hydrophobic block of the stabilizer in the release media should be less than the temperature at which the release is being measured if low burst (<20%) is desired. For applications in which bulking agents are not employed, the glass transition temperature of the hydrophobic block of the stabilizer in the release media should be at least 1° C. less than the temperature at which the release is being measured if low burst (<20%) is desired. For applications in which bulking agents are not employed, the glass transition temperature of the hydrophobic block of the stabilizer in the release media should be at least 5° C. less than the temperature at which the release is being measured if low burst (<20%) is desired. For applications in which bulking agents are not employed, the glass transition temperature of the hydrophobic block of the stabilizer in the release media should be at least 10° C. less than the temperature at which the release is being measured if low burst (<20%) is desired. For applications in which bulking agents are not employed, the glass transition temperature of the hydrophobic block of the stabilizer in the release media should be at least 20° C. less than the temperature at which the release is being measured if low burst (<20%) is desired.

Stabilization of Inverted Nanoparticles

The particles are formed and stable in the organic non-process solvent. In most applications, it is required that final construct is stable in aqueous environments for a set, non-negligible amount of time. In order to process the particles into an aqueous environment, particle stabilization is required. Without stabilization, particle may dissolve, aggregate, and/or release the water soluble target material from the core.

In one embodiment of this invention, sections of the core of the particle may be stabilized. The core refers to the more polar sections of the copolymer and encapsulated material. Material may be incorporated into the core specifically for the purpose of particle stabilization. In one embodiment of this invention, the shell of the particle may be stabilized. The shell refers to the more non-polar sections of the copolymer that are soluble in the non-process solvent.

Stabilization can involve the formation of new covalent bonds. The core of the particle may be cross-linked through the formation of new covalent bonds. The bonds may be formed directly between groups on the copolymer. Covalent bonds may be formed by adding an extra material to the core for the specific purpose of cross-linking the polymer in the core. The crosslinking material may be added to the core of the particle during the FNP process. The crosslinking material may be added to the solution after the particle has formed. If the crosslinking material is added after the particles have been formed, the crosslinking may be diffusion limited and only occur on the outer layers of the core. If the crosslinking material is added to the solution after the particles have been formed, the particle may be cross-linked throughout the core, if the core is swollen with solvent or if the cross-linking material is small enough to diffuse throughout the core. The shell of the particle may be cross-linked through the formation of new covalent bonds. The bonds may be formed directly between groups on the copolymer, or through the addition of an extra crosslinking material.

Examples of covalent chemistries that may be used include, but are not limited to carbodiimide coupling of carboxylic acids to alcohols or carboxylic acids to amines, the coupling of activated esters to alcohols or amines, maleimide-thiol chemistry, Micheal addition, azide-alkyne "click" chemistry, UV or light activated chemistries, and/or disulfide formation.

Stabilization can be obtained through non-covalent interactions. The core of the particle may be cross-linked through non-covalent interactions. The interactions may be directly between groups on the copolymer. Non-covalent interactions may be formed by adding an extra material to the core for the specific purpose of cross-linking the polymer in the core. This crosslinking material may be added to the core of the particle during the FNP process. This crosslinking material may be added to the solution after the particle has formed. If the crosslinking material is added after the particles have been formed, the crosslinking may be diffusion limited and only occur on the outer layers of the core. If the crosslinking material is added to the solution after the particles have been formed, the particle may be crosslinked throughout the core if the core is swollen with solvent or if the crosslinking material is small enough to diffuse throughout the core. The shell of the particle may be cross-linked through non-covalent interactions. The interactions may be formed directly between groups on the copolymer, or through the addition of an extra crosslinking material.

Examples of non-covalent interactions that may be used include, but are not limited to, ionic interactions, acid-base interactions, metal chelation, interactions between polyhistidines and metal such as nickel, and/or strong hydrogen bonding. An illustrative example of non-covalent particle stabilization is the use of Cr(III) to stabilize the poly(acrylic acid) core of a nanoparticle.

Multiple types of stabilization chemistries may be employed within a given particle. Stabilization may occur in the core, in the shell, at the interface, or in multiple locations within a given particle.

For many applications, particle degradation and release of encapsulated material is required. The type of stabilization chemistry used, and the density of the cross-linked network, will affect the degradation kinetics of the particle. The type of stabilization chemistry used, and the density of the cross-linked network, will affect the release kinetics of encapsulated material from the core of the particle.

For some applications, it is required that the encapsulated material is not chemically modified. In these cases, non-covalent interactions should be used to stabilize the particle. In these cases, covalent crosslinking may be used as long as the chemistry is specific to the copolymer.

The stabilization of the nanoparticle core can increase encapsulation efficiency and decrease burst release. For covalent and non-covalent (ionic) crosslinking, increasing the degree of crosslinking results in higher encapsulation efficiencies and lower burst release. The degree of crosslinking is the percentage of crosslinkable groups that have been crosslinked. The degree of crosslinking can be controlled by the amount of crosslinking agent incorporated into the formulation. For example, if ionically crosslinking a poly(aspartic acid) block of a stabilizing polymer, the degree of crosslinking can be modified through the amount of cation, such as $Ca^{2+}$, added to the nanoparticles. In the case of ionic crosslinking, the degree of ionization of the polymer and the crosslinker can also affect the degree of crosslinking. For example, if the ionically crosslinking a poly(aspartic acid) block with a cation such as $Ca^{2+}$, the degree of crosslinking will be higher if the poly(aspartic acid) is ionized.

Figure 6A:
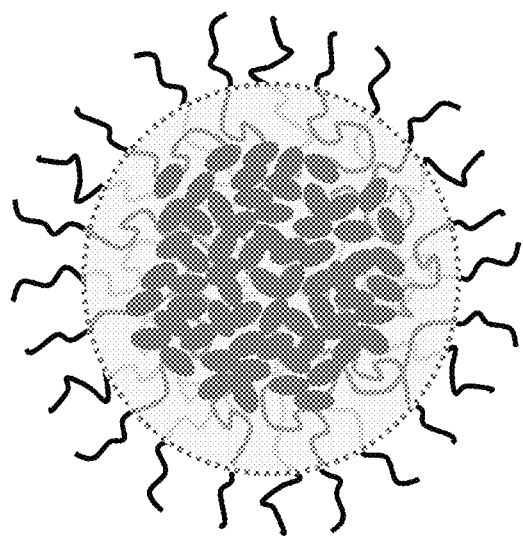
Figure 6B:
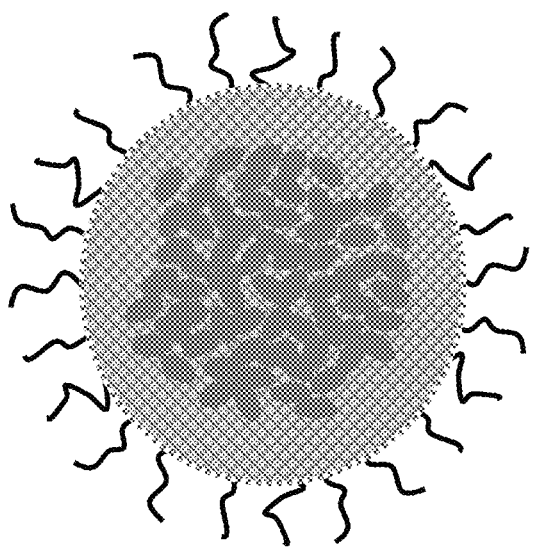

Though not limited to this description, it is possible that crosslinking can increase encapsulation efficiency and decrease burst release in two ways. First, the crosslinked polymer can create a diffusion barrier for the encapsulated material (FIG. 6). Second, the crosslinked polymer can inhibit osmotic swelling of the nanoparticle core. Osmotic swelling of the nanoparticle core can increase the exposure of the encapsulate materials to external phases.

In other cases, the crosslinking agent can increase encapsulation efficiency and reduce burst release by interacting with the encapsulated material. As an illustrative example, if an anionic stabilizing polymer is ionically crosslinked with a cationic crosslinker, the cationic crosslinker will also ionically interact with encapsulated material that is anionic and ionically crosslink the encapsulated material to the stabilizing polymer. This would result in higher encapsulation efficiencies and lower burst release. Alternatively, the polymer stabilizer and encapsulated material could be cationic and an anionic crosslinking agent could be used to produce the same effect. If covalent crosslinking is used, the encapsulated material may be covalently attached to the stabilizing polymer by the crosslinking agent. This would increase encapsulation efficiency and decrease burst release, but it may also prevent release on any reasonable timescale. A useful example is if the particle is covalently stabilized through disulfide bonds and encapsulated material with thiols are also crosslinked to the particle core through disulfide bonds.

Different formulations may have different crosslinking strength requirements. Without being bound by theory or the examples provided herein, there are a number of variables that may influence what this crosslink strength threshold is, such as propensity towards swelling, amphiphilicity of the encapsulated material, specific interactions of the encapsulated material with the core polymer, or hydrophobic block size. Sufficient crosslinking strength in the nanoparticle process is best assessed by screening formulations with and without crosslinking. If the encapsulation efficiency and burst release is similar between the non-crosslinked and crosslinked formulations, the crosslinking is not strong enough. DLS of the particles in a good solvent (a solvent that would dissolve non-crosslinked particles) will indicate the strength of crosslinking. DLS analysis of well-crosslinked particles should show resistance to swelling in the good solvent. This is observed in two ways. First, the automatic attenuator selection indicated very low light scattering (maximum attenuator). Second, the correlation function did not exhibit the expected monotonic decay over a narrow measurement window. A more thorough discussion on how to measure crosslinking of inverted nanoparticles with DLS is provided in Pagels & Prud'homme [Pagels, R. F.; Prud'homme, R. K. Inverse Flash NanoPrecipitation for Biologics Encapsulation: Nanoparticle Formation and Ionic Stabilization in Organic Solvents. *ACS Symp. Ser.* 2017, 1271, 249-274.].

Particle Coating—Layer-by-Layer Flash NanoPrecipitation

After particle stabilization, a second layer of copolymer may be added to the surface of the particle. This may be done to modify the surface properties of the particle to make it stable in an aqueous environment. This may be accomplished if the shell of the particle—that is, the more nonpolar sections of the copolymer—is not water soluble. Particle coating with a stabilizing amphiphilic polymer may be accomplished in a second Flash Nano Precipitation step. Particles must be sufficiently stabilized prior to being coated such that they may withstand the coating process.

Typically, the stabilizing amphiphilic polymer is a copolymer of a hydrophilic block coupled with a hydrophobic block. Nanoparticles coated by the process of this invention can be coated with graft, block or random amphiphilic copolymers. These copolymers can have a molecular weight between about 1000 g/mole and 50,000 g/mole, between about 3000 g/mole and 25,000 g/mole, or at least 2000 g/mole. Examples of suitable hydrophobic blocks in an amphiphilic copolymer include but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, vinyl phenols and vinyllimidazole; aminoalkyls including aminoalkylacrylates, aminoalkylsmethacrylates, and aminoalkyl(meth)acrylamides; styrenes; cellulose acetate phthalate, cellulose acetate succinate, hydroxypropylmethylcellulose phthalate, poly(D,L lactide), poly (D,L-lactide-co-glycolide), poly(glycolide), poly(hydroxybutyrate), poly (alkylcarbonate) and poly(orthoesters), polyesters, poly (hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., it al., Advanced Drug Delivery Reviews (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anyhydride copolymers of vinyl methylether and other vinyl ethers, polyamides (nylon 6,6), polyurethane, poly(ester urethanes), poly(ether urethanes), and poly(ester-urea). Polymeric blocks that can be used include poly(ethylenevinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid). For non-biologically related applications, polymeric blocks that can be used include polystyrene, polyacrylates, and polybutadienes.

Natural products with sufficient hydrophobicity to act as the hydrophobic portion of the amphiphilic polymer include: hydrophobic vitamins (for example vitamin E, vitamin K, and A), carotenoids and retinols (for example beta carotene, astaxanthin, trans and cis retinal, retinoic acid, folic acid, dihydrofolate, retinylacetate, retinyl palmintate), cholecalciferol, calcitriol, hydroxycholecalciferol, ergocalciferol, alpha-tocopherol, alpha-tocopherol acetate, alpha-tocopherol nicotinate, and estradiol. For example, vitamin E can be used, and can be readily obtained as a vitamin E succinate, which facilitates functionalization to amines and hyroxyls on the active species.

Examples of suitable hydrophilic blocks in an amphiphilic copolymer include but are not limited to the following: carboxylic acids including acrylic acid, methacrylic acid, itaconic acid, and maleic acid; polyoxyethylenes, poly (ethylene oxide), or poly(propylene oxide); polyacrylamides and copolymers thereof with dimethylaminoethylmethacrylate, diallyldimethylammonium chloride, vinylbenzylthrimethylammonium chloride, acrylic acid, methacrylic acid, 2-crrylamideo-2-methylpropane sulfonic acid and styrene sulfonate, polyvincyl pyrrolidone, starches and starch derivatives, dextran and dextran derivatives; polypeptides, such as polylysines, polyarginines, polyglutamic acids; poly hyaluronic acids, alginic acids, polylactides, polyethyleneimines, polyionenes, polyacrylic acids, and polyiminocarboxylates, gelatin, and unsaturated ethylenic mono or dicarboxylic acids. For example, suitable hydrophilic blocks are poly(ethylene oxide) and poly poly hydroxyl propyl acrylamide and methacrylamide to prepare neutral blocks, because these materials are in currently approved medical applications. To prepare anionic copolymers acrylic acid and methacrylic acid and poly aspartic acid polymers can be used. And to produce cationic amphiphilic copolymers DMAEMA (dimethylaminoethylmethacrylate), polyvinyl pyridine (PVP) or dimethylaminoethylacrylamide (DMAMAM) can be used.

For example, the blocks can be diblock or triblock repeats. Block copolymers useful for this invention include blocks of polystyrene, polyethylene, polybutyl acrylate, polybutyl methacrylate, polylactic acid (PLA), polyglutamic acid (PGA) and PLGA copolymers, polycaprolactone, polyacrylic acid, polyoxyethylene and polyacrylamide. A listing of suitable hydrophilic polymers can be found in Handbook of Water-Soluble Gums and Resins, R. Davidson, McGraw-Hill (1980).

In graft copolymers, the length of a grafted moiety can vary. The grafted segments can be alkyl chains of 4 to 18 carbons or equivalent to 2 to 9 ethylene units in length. The grafting of the polymer backbone can be useful to enhance solvation or nanoparticle stabilization properties. A grafted butyl group on the hydrophobic backbone of a diblock copolymer of a polyethylene and polyethylene glycol should increases the solubility of the polyethylene block. Suitable chemical moieties grafted to the block unit of the copolymer comprise alkyl chains containing species such as amides, imides, phenyl, carboxy, aldehyde or alcohol groups.

The method of coating the nanoparticles is termed "Flash NanoPrecipitation" (see, Johnson, B. K., et al., AIChE Journal (2003) 49:2264-2282 and U.S. Pat. No. 8,137,699, which are incorporated herein by reference in their entirety) is a rapid, single-step block copolymer-directed precipitation process. The particles and amphiphilic block copolymers are dissolved in a water-miscible organic solvent. Acceptable solvents include, but are not limited to, tetrahydrofuran, dimethylformamide, acetonitrile, acetone, low molecular weight alcohols such as methanol and ethanol, dimethyl sulfoxide, or mixtures thereof. Solvent quality is rapidly reduced by micromixing against water or an aqueous buffer or mixture to produce supersaturations as high as 10,000 to drive rapid precipitation wherein the time of mixing is faster than the aggregation of the nanoparticles and balances with the timescale of block copolymer self-assembly. This process is capable of producing controlled size, polymer-stabilized and protected nanoparticles.

The Flash NanoPrecipitation coating technique is based on amphiphilic diblock copolymer arrested aggregation of the nanoparticles produced by the initial FNP process. Amphiphilic diblock copolymers dissolved in a good solvent can form micelles when the solvent quality for one block is decreased. The intense micromixing can be effected in any number of geometries. The essential idea is that high velocity inlet streams cause turbulent flow and mixing that occurs in a central cavity. The time for solvent/antisolvent mixing is more rapid than the assembly time of the nanoparticles. While not meant to be limiting, two such geometries have been previously described and analyzed: the Confined Impinging Jet mixer (CIJ) or a multi-inlet vortex mixer (MIVM). These examples are meant to be illustrative rather than limiting or exhaustive.

The vortex mixer consists of a confined volume chamber where one jet stream containing the dissolved diblock copolymer and particles suspended in a water-miscible solvent is mixed at high velocity with another jet stream containing water, an anti-solvent for the nanoparticle shell and the hydrophobic block of the copolymer. The fast mixing and high energy dissipation involved in this process provide timescales that are shorter than the timescale for nucleation and growth of particles, which leads to the formation of nanoparticles with active agent loading contents and size distributions not provided by other technologies. When coating the nanoparticles via Flash NanoPrecipitation, mixing occurs fast enough to allow high supersaturation levels of all components to be reached prior to the onset of aggregation. Therefore, the particles and polymers precipitate simultaneously, and overcome the limitations of low active agent incorporations and aggregation found with techniques based on slow solvent exchange (e.g., dialysis). The Flash NanoPrecipitation process is insensitive to the chemical specificity of the components, making it a universal nanoparticle coating technique.

Figure 8:
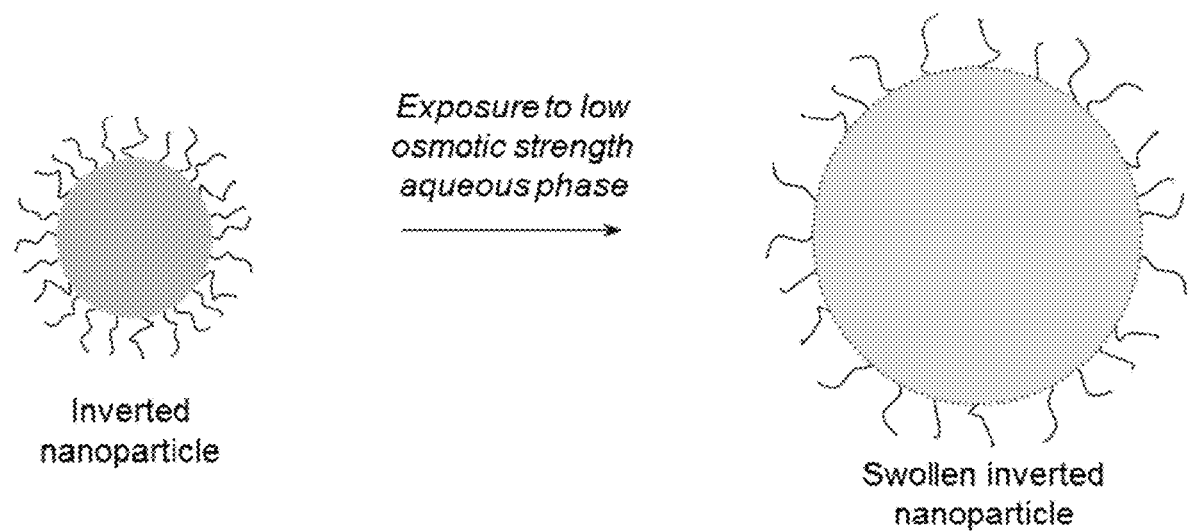

The solvent system used in the nanoparticle coating process can impact the encapsulation efficiency. Solvents in which the nanoparticle core components are insoluble will increase encapsulation efficiency in the overall process. For example, if the hydrophilic (core-forming) block of the stabilizing polymer is poly(aspartic acid), using tetrahydrofuran in the coating process can be better than using dimethylsulfoxide (DMSO), because the poly(aspartic acid) is insoluble in tetrahydrofuran, but soluble in dimethylsulfoxide. In many cases, the final coated nanoparticles are intended to be stable in water, thus the coating process takes place with water present. For example, if Flash NanoPrecipitation is used to coat the nanoparticles, one of the solvent streams may be water. If this is the case, the osmotic strength of the aqueous phase used in the coating process can impact the encapsulation efficiency. Aqueous phases or streams with higher osmotic strengths tend to result in higher encapsulation efficiencies. Not limited by theory, this is because the hydrophilic nanoparticle core will swell less when exposed to high osmotic strength aqueous phases as compared to aqueous phases of lower osmotic strength (FIG. 8). Nanoparticle swelling can increase exposure of the particle contents to external phases, resulting in losses of the encapsulated material. The osmotic strength of any aqueous phase or stream used in the coating process can be modified through the addition of salts, small molecules including, but not limited to sugars, polymers including, but not limited to polysaccharides and poly(ethylene glycol), or combinations of these agents.

In order to have high encapsulation efficiencies (>50%) when coating inverted nanoparticles, any aqueous phases should have high osmolarities. In order to have high encapsulation efficiencies (>50%) when coating inverted nanoparticles, any aqueous phase used during nanoparticle processing should have an osmolarity that is at least 50% of the osmolarity of the final release conditions. When coating inverted nanoparticles, the osmolarity of any aqueous phases should be the osmolarity of the final release buffer or greater in order to maximize encapsulation efficiency.

In order to have low burst release (<20%, <30%, <40%, <50%) from coated inverted nanoparticles, any aqueous phases used in the coating process should have osmolarities equal to or less than the osmolarity of the release buffer. In order to have low burst release (<20%, <30%, <40%, <50%) from coated inverted nanoparticles, any aqueous phases used in the coating process should have osmolarities no more than 2-times the osmolarity of the release buffer.

In order to have both high encapsulation efficiency and low burst release from coated inverted nanoparticles, any aqueous phase used in the coating process should have osmolarities similar to the osmolarity of the release buffer. In order to have both high encapsulation efficiency and low burst release from coated inverted nanoparticles, any aqueous phase used in the coating process should have osmolarities between 25% and 200% of the osmolarity of the release buffer. In order to have both high encapsulation efficiency and low burst release from coated inverted nanoparticles, any aqueous phase used in the coating process should have osmolarities between 75% and 150% of the osmolarity of the release buffer.

The concentrations, copolymers, and solvents used in the coating process may be optimized such that individual particles are coated, or particles aggregate to a desired size prior to being coated.

Coating the particles will modify the surface chemistry of the particles. Coating the particles may change the stability and degradation kinetics of the particles in an aqueous media. Coating the particles may change the release kinetics of encapsulated material.

Figure 7A:
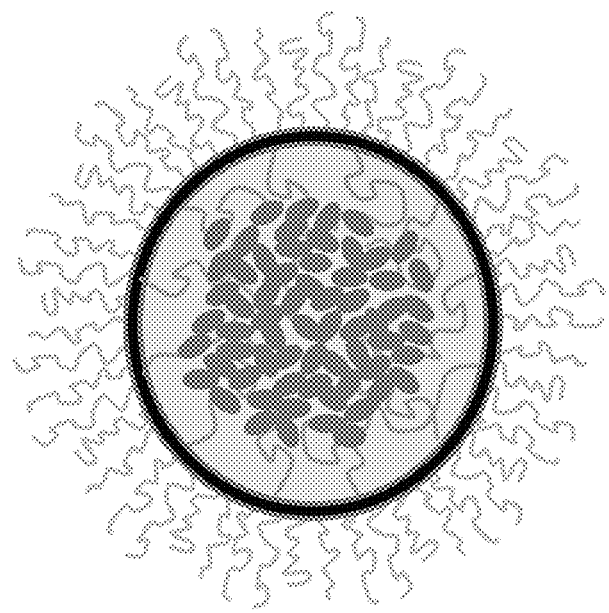
Figure 7B:
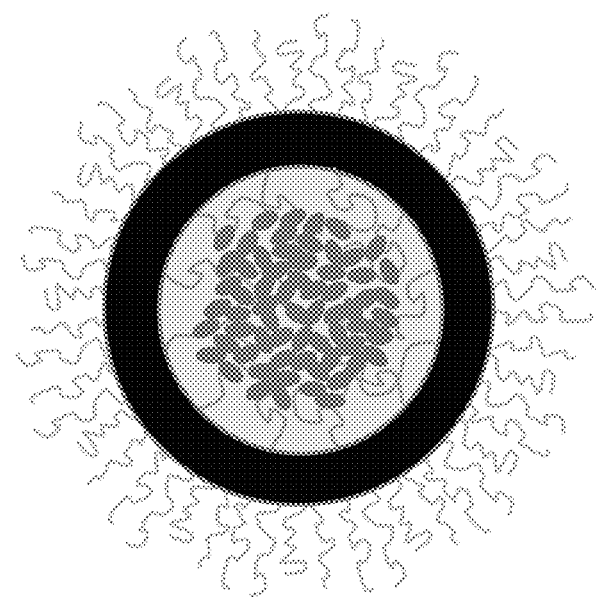

The encapsulation efficiency and burst release from coated nanoparticles can be modified through the physical characteristics of the coating material (FIG. 7). In the final coated nanoparticle, particles with thicker hydrophobic layers will have higher encapsulation efficiencies and lower burst release. This can be achieved in several ways. First, the hydrophobic layer thickness can be increased by using a higher molecular weight hydrophobic block in the stabilizing polymer used in the formation of the inverted nanoparticle. This was described above. Second, the thickness of the hydrophobic layer can be increased by using a high concentrations of coating agents, or by using coating agents with high molecular weight hydrophobic blocks. Finally, the thickness of the hydrophobic layer can be increased by added hydrophobic additives ("bulking agents") during the coating process. The hydrophobic additive bulk up the hydrophobic layer surrounding the nanoparticle core. The hydrophobic additives can be polymers. For example, the hydrophobic additives could be, but are not limited to, poly(lactic acid), poly(lactic-co-glycolic acid), or poly(caprolactone). Hydrophobic polymer additives can be between 500 and 1,000 Daltons. Hydrophobic polymer additives can be between 1,000 and 10,000 Daltons. Hydrophobic polymer additives can be between 10,000 and 100,000 Daltons. Hydrophobic polymer additives can be between 100,000 and 500,000 Daltons. Hydrophobic polymer additives can be greater than 500,000 Daltons in molecular weight. The hydrophobic additives can be small molecules. For example, the hydrophobic additives can be, but are not limited to, vitamin E, cholesterol, fats, and waxes. The hydrophobic additives can have some amphiphilic characteristics. For example, the hydrophobic additives can be lecithin, oleic acid, phospholipids, anionic lipids, cationic lipids, or neutral lipids.

Not limited by theory, the bulking of the hydrophobic layer can prevent pore opening as discussed previously. In addition, hydrophobic additives can seal pores or cracks in the hydrophobic layer surrounding the particle core.

If sufficient bulking of the hydrophobic layer is accomplished, there should be a minimal difference in burst release (<10%) at release temperatures above and below the glass transition temperature of the hydrophobic phase in the release conditions. This can be determined by measuring and comparing the amount of encapsulated material released in 1 hr at least 5° C. above and at least 5° C. below the glass transition temperature of the hydrophobic phase in the release conditions.

Incorporation of Inverted Nanoparticles into Microparticles or Monoliths

Figure 9A:
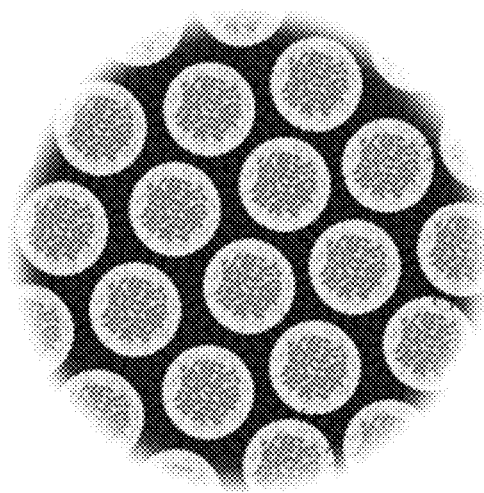
Figure 9B:
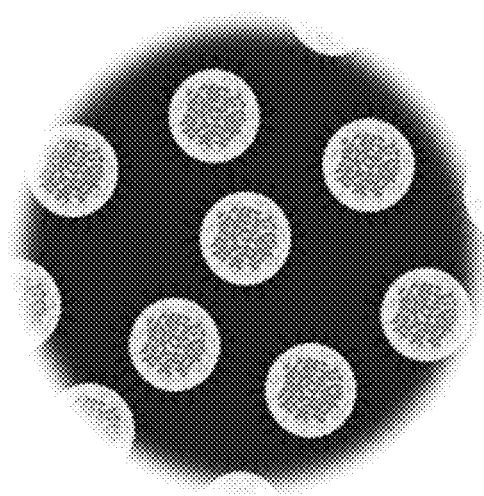

The inverted nanoparticles may be incorporated into microparticles or larger monoliths. The hydrophobic polymer block will prevent percolation and allow for high loading of the encapsulated material. Mixtures of different nanoparticles can be incorporated into microparticles to modify the release characteristics. Inverted nanoparticles made with different crosslinking or with different stabilizing polymers can be combined into a single microparticle to modify the release.

If the particles are being incorporated into a hydrophobic scaffold that is processed in a poor solvent for the particle core, the particle may not need to be stabilized prior to processing. However, particle stabilization (that is, stabilization of the hydrophilic interface) may be required.

The hydrophilic active compound or biologic compound is captured in the interior of the particle formed by the first processing step into the hydrophobic process solvent. Organic polymers soluble in the hydrophobic process solvent may be added to the particle dispersion. Polymers that might be added include biocompatible and or biodegradable polymers. Non-limiting examples of these polymers include: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate and copolymers of these acrylates; acrylonitriles; methacrylonitrile; vinyls including vinyl acetate, vinylversatate, vinylpropionate, vinylformamide, vinylacetamide, vinylpyridines, vinyl phenols and vinyllimidazole; aminoalkyls including aminoalkylacrylates, aminoalkylsmethacrylates, and aminoalkyl(meth)acrylamides; styrenes; cellulose acetate phthalate, cellulose acetate succinate, hydroxypropylmethylcellulose phthalate, poly(D,L-lactide), poly(D,L-lactide-co-glycolide), poly(glycolide), poly(hydroxybutyrate), poly(alkylcarbonate) and poly(orthoesters), polyesters, poly(hydroxyvaleric acid), polydioxanone, poly (ethylene terephthalate), poly(malic acid), poly(tartronic acid), polyanhydrides, polyphosphazenes, poly(amino acids) and their copolymers (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., it al., Advanced Drug Delivery Reviews (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anyhydride copolymers of vinyl methylether and other vinyl ethers, polyamides (nylon 6,6), polyurethane, poly(ester urethanes), poly(ether urethanes), poly(ester-urea). Polymeric blocks that can be used include poly(ethylenevinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) For non-biologically related applications polymeric blocks that can be used include polystyrene, polyacrylates, and polybutadienes.

Hydrophobic small molecules may also be added to the nanoparticle dispersion. For example, the hydrophobic additives may be, but are not limited to, vitamin E, cholesterol, fats, and waxes. The hydrophobic additives can contain some amphiphilic characteristics. For example, the hydrophobic additives can be lecithin, oleic acid, phospholipids, anionic lipids, cationic lipids, or neutral lipids.

After addition of these polymers, hydrophobic small molecules, or mixtures thereof, the resulting dispersed inverted nanoparticles in the polymer containing hydrophobic organic solution phase can be dried to form a solid matrix containing the encapsulated hydrophilic material. In some cases, no polymers or hydrophobic small molecules are added. Microparticles or larger monoliths composed of the inverted nanoparticles and any added polymer or hydrophobic small molecules can be formed by spray drying, by pan drying, by molding processes, or by emulsion-stripping to obtain a solid final matrix containing the encapsulated hydrophilic agent. For example, the inverted nanoparticles in an oil phase with any dissolved hydrophobic polymer can be emulsified in an aqueous phase containing a surfactant. After emulsification, the oil is removed by evaporation, resulting in hardened microparticles composed of the inverted nanoparticles as well as any added hydrophobic materials. Release is then effected by dissolution, erosion, or swelling of the matrix phase. This encapsulation followed by matrix formation enables much higher loadings of the hydrophilic active or biologic than can be achieved by simple double emulsion techniques.

When assembling the inverted nanoparticles into larger microparticles or monoliths, the burst release and encapsulation efficiency can be controlled by the addition of hydrophobic additives including hydrophobic polymers and small molecules, as described above. These additives can increase the thickness of the hydrophobic layer surrounding the hydrophilic core of each nanoparticle, creating a thicker barrier which in turn increases encapsulation efficiency and decreases burst release (FIG. 9). Not limited by theory, the addition of bulking agents can decrease the critical pore diameters as described previously and cause pore closing when the glass transition temperature of the hydrophobic material is less than the temperature at which release is occurring.

When assembling nanoparticles into larger microparticles or monoliths, the glass transition temperature of the hydrophobic regions of the final construct can be modified through the addition of additives. These additives can be small molecules or polymers, as described above. The additives can be plasticizers, which decrease the glass transition temperature. These additives can be tackifiers, which increase the glass transition temperature. For microparticles or larger monoliths in which the hydrophobic layer (composed of the hydrophobic block of the stabilizing polymer as well as any hydrophobic additives) surrounding each nanoparticle core is thin, additives which decrease the glass transition temperature can result in lower encapsulation efficiency and higher burst release. Not limited by theory, thin hydrophobic layers will have smaller critical pore sizes, therefore, when the release temperature is higher than the glass transition temperature of the hydrophobic material, the pores open resulting in higher processing losses and greater burst release. For microparticles or larger monoliths in which the hydrophobic layer (composed of the hydrophobic block of the stabilizing polymer as well as any hydrophobic additives) surrounding each nanoparticle core is thick, additives which decrease the glass transition temperature can result in lower burst release. Not limited by theory, thick hydrophobic layers will have larger critical pore sizes, therefore, when the release temperature is higher than the glass transition temperature of the hydrophobic material, the pores close, resulting in lower burst release.

The hydrophobic additive(s) (bulking agents) must be sufficiently hydrophobic such that >50%, >60%, >70%, >90%, or >95% of the bulking agent remains within the microparticle throughout processing. The bulking agent(s) must be sufficiently hydrophobic such that >50% of the bulking agent remains within the microparticle after 48 hrs.

When the glass transition temperature of the hydrophobic phase in the release conditions is 1° C., 5° C., 10° C., 20° C., or 30° C. greater than the release temperature, bulking agents are not required to obtain low (<20%) burst release from microparticles. However, bulking agents may still be added to further reduce the burst release and increase the encapsulation efficiency.

When the glass transition temperature of the hydrophobic phase in the release conditions is 1° C., 5° C., 10° C., 20° C., or 30° C. lower than the release temperature, bulking agents may be required to obtain low (<20%) burst release from microparticles. To determine if bulking agents are needed, the user should measure and compare the amount of encapsulated material released in 48 hrs at least 5° C. above and at least 5° C. below the glass transition temperature of the hydrophobic phase in the release conditions. If the burst release at the higher temperature is more than 15% greater than the burst release at the lower temperature, bulking agents should be added to reduce the burst release. The bulking agent can be added to form less than 5 wt %, 10 wt %, 20 wt %, 30 wt %, 40 wt %, 50 wt %, 60 wt %, 70 wt %, 80 wt %, or 90 wt % of the final microparticle. A sufficient amount of bulking material will result in burst release <20%.

If sufficient bulking of the hydrophobic layer is accomplished, there should be a minimal difference in burst release (<10%) at release temperatures above and below the glass transition temperature of the hydrophobic phase in the release conditions. This can be determined by measuring and comparing the amount of encapsulated material released in 48 hrs at least 5° C. above and at least 5° C. below the glass transition temperature of the hydrophobic phase in the release conditions.

When assembling the inverted nanoparticles into larger microparticles by an emulsion-stripping method with an oil-in-water emulsion, the osmotic strength of the external aqueous phase can affect the encapsulation efficiency of the hydrophilic encapsulated material. Aqueous phases with higher osmotic strengths tend to result in higher encapsulation efficiencies. Not limited by theory, this is because the hydrophilic nanoparticle core will swell less when exposed to high osmotic strength aqueous phases as compared to aqueous phases of lower osmotic strength (FIG. 8). Nanoparticle swelling can increase exposure of the particle contents to external phases, resulting in losses of the encapsulated material. The osmotic strength of any aqueous phase used during an emulsion stripping process can be modified through the addition of salts, small molecules including but not limited to sugars, polymers including but not limited to polysaccharides and poly(ethylene glycol), or combinations of these agents.

In order to have high encapsulation efficiencies (>70%) when assembling inverted nanoparticles into microparticles, any aqueous phases should have high osmolarities. In order to have high encapsulation efficiencies (>70%) when assembling inverted nanoparticles into microparticles, any aqueous phase should have an osmolarity that is at least 50% of the osmolarity of the final release conditions. When assembling inverted nanoparticles into microparticles, the osmolarity of any aqueous phases should be the osmolarity of the final release buffer or greater in order to maximize encapsulation efficiency. It should be noted that if large amounts of bulking agents have been added or if large hydrophobic stabilizer blocks (>40 kDa) are used, then the osmotic strength of aqueous phases will have less of an effect.

In order to have low burst release (<20%, <30%, <40%, or <50%) from microparticles assembled from inverted nanoparticles, any aqueous phases used in the coating process should have osmolarities equal to or less than the osmolarity of the release buffer. In order to have low burst release (<20%, <30%, <40%, or <50%) from microparticles assembled from inverted nanoparticles, any aqueous phases used in the coating process should have osmolarities no more than 2-times the osmolarity of the release buffer. It should be noted that if large amounts of bulking agents have been added or if large hydrophobic stabilizer blocks (>40 kDa) are used, then the osmotic strength of aqueous phases will have less of an effect.

In order to have both high encapsulation efficiency and low burst release from microparticles assembled from inverted nanoparticles, any aqueous phase used in the coating process should have osmolarities similar to the osmolarity of the release buffer. In order to have both high encapsulation efficiency and low burst release from microparticles assembled from inverted nanoparticles, any aqueous phase used in the coating process should have osmolarities between 25% and 200% of the osmolarity of the release buffer. In order to have both high encapsulation efficiency and low burst release from microparticles assembled from inverted nanoparticles, any aqueous phase used in the coating process should have osmolarities between 75% and 150% of the osmolarity of the release buffer. It should be noted that if large amounts of bulking agents have been added or if large hydrophobic stabilizer blocks (>40 kDa) are used, then the osmotic strength of aqueous phases will have less of an effect.

When assembling inverted nanoparticles into microparticles or larger monoliths, the processing temperature can impact the encapsulation efficiencies. In general, when the hydrophobic layer surrounding each nanoparticle core is thin, lower temperatures will result in higher encapsulation efficiencies. Not limited by theory, when the processing temperature is greater than the glass transition temperature of the hydrophobic materials, pores in the microparticle will open causing greater processing losses (lower encapsulation efficiencies). If large amounts of hydrophobic additives are added to increase the thickness of the hydrophobic layer surrounding each nanoparticle core, then this temperature effect may not be observed. Not limited by theory, this temperature effect may not be observed with thick hydrophobic layers, because the critical pore diameter will be larger, therefore, pore opening will no longer occur at higher temperatures.

When assembling inverted nanoparticles into microparticles, it may be preferred to keep the processing temperature less than the glass transition temperature of the hydrophobic material of the particle within the processing solvents in order to obtain high encapsulation efficiencies. When assembling inverted nanoparticles into microparticles, the processing temperature should be at least 1° C., 5° C., 10° C., or 20° C. less than the glass transition temperature of the hydrophobic material of the particle within the processing solvents in order to obtain high encapsulation efficiencies. When assembling inverted nanoparticles into microparticles, the processing temperature should be no greater than 1° C., 5° C., 10° C., or 20° C. higher than the glass transition temperature of the hydrophobic material of the particle within the processing solvents in order to obtain high encapsulation efficiencies. It should be noted that if large amounts of bulking agents have been added, then the processing temperature may not have a strong effect on the encapsulation efficiency.

Other Processing Effects

After coating inverted nanoparticles or assembling them into microparticles, for some applications other processing steps are required. An example of an additional processing step would be to wash the nanoparticles or microparticles to remove any soluble materials in the external phase. Such a washing step could involve centrifuging the particles out of solution and resuspending the particles in a new aqueous phase. Independent of the exact details or purpose of the processing step, the temperature at which the step is completed can affect the encapsulation efficiency and release of the encapsulated hydrophilic materials. For particles with thin hydrophobic layers surrounding the hydrophilic nanoparticle core, exposure to temperatures greater than the glass transition temperature of the hydrophobic material can result in lower encapsulation efficiencies and higher burst release. Not limited by theory, this may be because pore opening will occur in thin hydrophobic interfaces at temperatures greater than the glass transition temperature. For particles with thick hydrophobic layers surrounding the hydrophilic nanoparticle core, exposure to temperatures greater than the glass transition temperature of the hydrophobic material can result in higher encapsulation efficiencies and lower burst release. Not limited by theory, this is because pore closing will occur in thick hydrophobic interfaces at temperatures greater than the glass transition temperature.

The same temperature guidelines provided above for coating inverted nanoparticles can be used in subsequent processing steps.

The same temperature guidelines provided above for assembling inverted nanoparticles into microparticles can be used in subsequent processing steps.

In processing steps, processing temperatures at least 1° C., 5° C., 10° C., or 20° C. less than the glass transition temperature of the hydrophobic phase in the processing conditions can be used to achieve high encapsulation efficiencies. In processing steps, the processing temperature should be no more than 1° C., 5° C., 10° C., 20° C., or 30° C. higher than the glass transition temperature (Tg) of the hydrophobic phase to achieve high encapsulation efficiencies.

In some cases, the particles may be exposed to aqueous phases during additional processing steps. If this is the case, then the osmotic strength of the aqueous phase used in the processing step can impact the encapsulation efficiency. Aqueous phases with higher osmotic strengths tend to result in higher encapsulation efficiencies. Not limited by theory, this may be because the hydrophilic nanoparticle core will swell less when exposed to high osmotic strength aqueous phases as compared to aqueous phases of lower osmotic strength. Nanoparticle swelling can increase exposure of the particle contents to external phases, resulting in losses of the encapsulated material. The osmotic strength of any aqueous phase can be modified through the addition of salts, small molecules including but not limited to sugars, polymers including but not limited to polysaccharides and poly(ethylene glycol), or combinations of these agents.

The same osmolarity guidelines provided above for coating inverted nanoparticles can also be used in subsequent processing steps.

The same osmolarity guidelines provided above for assembling inverted nanoparticles into microparticles can be used in subsequent processing steps.

If the particles are to be freeze-dried in a pure form (no salts or other additives present), processing steps may require aqueous phases with no salts or other solutes. In these cases, processing temperatures at least 1° C., 5° C., 10° C., or 20° C. less than the glass transition temperature of the hydrophobic phase in the processing conditions may be used to achieve high encapsulation efficiencies.

Release Conditions

For most applications, the final nanoparticles, microparticles, or monoliths are meant to release the encapsulated hydrophilic agents into an aqueous phase. The temperature of this aqueous phase can impact the amount of burst release. For particles with thin hydrophobic layers surrounding the hydrophilic nanoparticle core, release temperatures greater than the glass transition temperature of the hydrophobic material can result in higher burst release. Not limited by theory, this may be because pore opening will occur in thin hydrophobic interfaces at temperatures greater than the glass transition temperature. For particles with thick hydrophobic layers surrounding the hydrophilic nanoparticle core, release temperatures greater than the glass transition temperature of the hydrophobic material can result in higher encapsulation efficiencies and lower burst release. Not limited by theory, this may be because pore closing will occur in thick hydrophobic interfaces at temperatures greater than the glass transition temperature.

The osmotic strength of the aqueous phase in which the release occurs can affect the amount of burst release. Aqueous phases with higher osmotic strengths tend to result in lower burst release. Not limited by theory, this may be because the hydrophilic nanoparticle core will swell less when exposed to high osmotic strength aqueous phases as compared to aqueous phases of lower osmotic strength. Nanoparticle swelling can increase exposure of the particle contents to external phases, resulting in losses of the encapsulated material.

EXAMPLES

Example 1: Baseline Microparticle Formulation of PEP1

Figure 10:
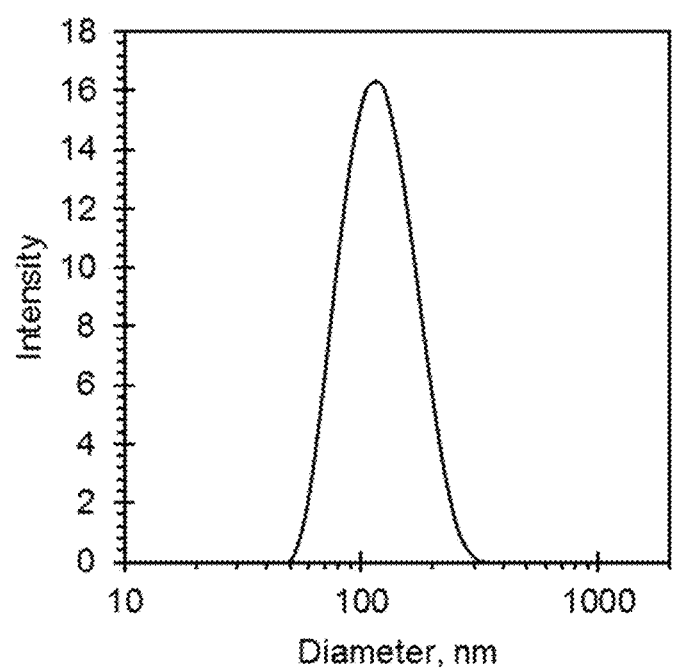

Inverted nanoparticles loaded with PEP1, a ~30 amino acid long peptide, were produced by inverse Flash Nano-Precipitation (iFNP). The process solvent stream was 500 µL of dimethyl sulfoxide (DMSO) with 5 v % water. The process solvent stream contained 5 mg/mL PEP1 and 12.5 mg/mL poly(aspartic acid) (5 kDa)-b-poly(lactic acid) (40 kDa)-b-poly(aspartic acid) (5 kDa) (PAsp(5 kDa)-b-PLA(40 kDa)-b-PAsp(5 k Da)). The PEP1 was tagged (~1% tagged) with Alexa Fluor 488. The non-process solvent was 600 µL of dichloromethane (DCM) with 50 µL of methanol (MeOH) containing $CaCl_2$). The calcium cations crosslink the PAsp block of the stabilizing polymer. The process solvent and non-process solvent streams were rapidly mixed in a confined impingement jets (CIJ) mixer, and the effluent was collected in 4 mL of DCM. The calcium to aspartic acid charge ratio was 1.2 to 1 in the final solution. After nanoparticle assembly, 100 µL of an ammonium hydroxide in MeOH solution was slowly added to the inverted nanoparticles to strengthen the crosslinking. The resulting inverted nanoparticles were ~100 nm in diameter in DCM. An example size distribution in DCM is given in FIG. 10.

After the inverted nanoparticles had been crosslinked for 30 min, the DMSO was extracted with 1.67 mL of 150 mM NaCl in water (1:3 water:organic by volume) by inverting 5 times and then gently shaking for 30 min. The high density DCM phase containing the inverted nanoparticles was removed, and the brine phase was saved to measure the amount of extracted PEP1. The inverted nanoparticles were concentrated to ~10 mg/mL by rotary evaporating.

The concentrated inverted nanoparticle solution was added to the bottom of 6 mL of phosphate buffered saline (PBS, 150 mM) with 1 wt % polyvinyl alcohol (PVA, 80% hydrolyzed) in a glass scintillation vial. A nanoparticle-in-oil-in-water (N/O/W) emulsion was formed by gently swirling the vial ten times in a circular motion. After emulsification, the DCM was removed by rotary evaporation at 20° C. and 200 torr for 10 min, followed by 100 torr for 20 min, producing hardened microparticles.

After solvent removal, the microparticle dispersion was moved to a glass test tube with a PTFE-lined cap and kept cold on ice until washed (no longer than an hour). Prior to washing, the particles were centrifuged at 200 rcf for 10 min, and the supernatant was removed and analyzed for unencapsulated PEP1 by fluorescence. The particles were resuspended in 4 mL of ice-cold water and then centrifuged a second time. The supernatant was removed and the washing step was repeated twice more. The three washes for each formulation were combined and analyzed for unencapsulated PEP1 by fluorescence. The microparticles were frozen on dry ice in ~1 mL of water and lyophilized overnight. The encapsulation efficiency (EE) was calculated accounting for losses during all processing steps using the following equation:

$$EE(\%) = 100\% - \frac{(PEP1 \text{ loss to brine}) + (PEP1 \text{ loss to emulsion}) + (PEP1 \text{ loss to washes})}{(PEP1 \text{ at start of formulation})} * 100\%$$

Burst release was measured from the freeze dried microparticles by adding 5 mL of PBS with 0.02 wt % Tween 20 and 0.02 wt % $NaN_3$. The release sample was protected from light using aluminum foil and placed in a forced air incubator with set to 37° C. with a shaking speed of 125 rpm. To measure the amount of release PEP1, the microparticles were centrifuged from solution at 200 rcf for 10 min, and 1 mL of the aqueous phase was removed. If the sample was not immediately analyzed, it was frozen at −20° C. until the time of analysis. The amount of PEP1 released was determined by fluorescence. The burst release was measured as the amount released after 48 hrs. The percent release was calculated as the percent released with respect to the amount encapsulated.

Results:
The resulting microparticles had 70% EE and 69% burst release.

Example 2: Adding Vitamin E to Microparticles

The same process was used as given in Example 1, with the addition of vitamin E to the DCM oil phase used in the N/O/W emulsion. Upon emulsification and DCM removal the vitamin E stays in the microparticles and made up 10 or 20 wt % of the microparticles, depending on the amount added.

Result:
The microparticles with 10 wt % vitamin E had an encapsulation efficiency of 82% and a burst release of 64%. The microparticles with 20 wt % vitamin E had an encapsulation efficiency of 84% and a burst release of 22%. The addition of vitamin E increased encapsulation efficiency and decreases burst release.

Example 3: Adding Lecithin to Microparticles

The same process was used as given in Example 1, with the addition of lecithin to the DCM oil phase used in the N/O/W emulsion. Upon emulsification and DCM removal the lecithin stays in the microparticles and made up 20 wt % of the microparticles. Lecithin is water-insoluble, but is also amphiphilic in nature.

Result:
The microparticles with 20 wt % lecithin had an encapsulation efficiency of 88% and a burst release of 67%. The addition of lecithin increased the encapsulation efficiency.

Example 4: Using Stabilizers with Lower Molecular Weight PLA Block Plus Vitamin E The same process was used as given in Example 2, with different block copolymer stabilizers. For one formulation (50 mol % 40 kDa PLA block), the process solvent stream in the iFNP process contained 6.25 mg/mL of PAsp(5 kDa)-b-PLA(40 kDa)-b-PAsp(5 kDa) and 2.5 mg/mL PAsp(5 kDa)-b-PLA(10 kDa)-b-PAsp(5 kDa). For the second formulation (25 mol % 40 kDa PLA block), the process solvent stream in the iFNP process contained 3.125 mg/mL of PAsp(5 kDa)-b-PLA(40 kDa)-b-PAsp(5 kDa) and 3.75 mg/mL PAsp(5 kDa)-b-PLA(10 kDa)-b-PAsp(5 kDa). All else was kept the same.

Vitamin E was added to the oil phase of the N/O/W emulsion such that the final microparticles were 20 wt % vitamin E. All else in the microparticle processing and analysis was kept the same.

Results:

The particles made with 50 mol % of the 40 kDa PLA-containing block copolymer had an encapsulation efficiency of 71% and a burst release of 63%. The particles made with 25 mol % of the 40 kDa PLA-containing block copolymer had an encapsulation efficiency of 25% and a burst release of 29%. The encapsulation efficiency greatly decreased as the percent of the high molecular PLA stabilizer decreases (see Example 2 for comparison to particles with vitamin E and 100 mol % of the 40 kDa PLA-containing block copolymer). The burst release was highest for the 50 mol % 40 kDa PLA formulation. The burst release was lower for the 25 mol % 40 kDa PLA formulation, likely because most of the PEP1 was already lost during processing and the remaining PEP1 was well encapsulated.

Example 5: Using Stabilizers with Lower Molecular Weight PLA Blocks Plus Lecithin The same nanoparticle formation process given in Example 1 was used, with different stabilizing polymers. In the first formulation the solvent stream of the iFNP step contained 5 mg/mL of PAsp(5 kDa)-b-PLA(10 kDa)-b-PAsp(5 kDa); herein, this formulation will be referred to by the molecular weight of the PLA block (10 kDa PLA block). All else was the same. In the second formulation the solvent stream of the iFNP step contained 7.5 mg/mL of PAsp(5 kDa)-b-PLA(20 kDa)-b-PAsp(5 kDa); herein, this formulation will be referred to by the molecular weight of the PLA block (20 kDa PLA block). All else was the same.

The inverted nanoparticles were processed and assembled into microparticles using the method given in Example 1, with the addition of lecithin to the emulsion oil phase such that the final particles were 20 wt % lecithin, as given in Example 3. All else was the same.

Results:

The particles made with the 20 kDa PLA block had an encapsulation efficiency of 30% and a burst release of 12%. This is much lower encapsulation efficiency than the particles made with the 40 kDa PLA block and lecithin (Example 4). The burst is also lower, however, this is likely because most of the PEP1 was already lost during processing and the remaining PEP1 was well encapsulated.

The inverted nanoparticles made with the 10 kDa PLA block were not successfully formulated into microparticles. The microparticles fell apart because the 10 kDa PLA block was not sufficient to stick the inverted nanoparticles together.

Example 6: Adding Oleic Acid to Microparticles

The same process was used as given in Example 1, with the addition of oleic acid to the DCM oil phase used in the N/O/W emulsion, targeting 20 wt % oleic acid in the final microparticles.

Result:

The microparticles with 20 wt % oleic acid had an encapsulation efficiency of 58% and a burst release of 53%. The addition of lecithin decreased the encapsulation efficiency compared to Example 1. This is likely because oleic acid has a relatively high solubility in PBS, which was used as the release buffer. Therefore, the oleic acid was not hydrophobic enough to be an effective bulking agent.

Example 7: Changing the Drying Method

The same process was used as given in Example 1, with different methods for drying the final microparticles. The first sample (Freeze/Thaw) was not dried, and was instead frozen on dry ice and kept frozen for 24 hrs and then thawed before measuring release. The second sample (Vac-Dry) was washed with ice-cold ethanol two times after the water washes, using the same method that was used for the water washes as given in Example 1. The particles were then dried under high vacuum overnight. The final sample (No Dry) was immediately place in the release conditions after washing without a drying step. The No Dry formulation was also washed with ice-cold PBS instead of with ice-cold water, as was done for the previous samples.

Results:

The Freeze/Thaw formulation had an encapsulation efficiency of 83% and a burst release of 62%. The Vac-Dry formulation had an encapsulation efficiency of 88% and a burst release of 57%. The No Dry formulation had an encapsulation efficiency of 89% and a burst release of 58%. All three formulations had higher encapsulation efficiencies than that of Example 1 because greater care was taken to ensure that the washing steps were done cold (everything pre-chilled, including the centrifuge, to be between 0 to 5° C.). This shows that processing temperature is important for high encapsulation efficiencies. The No Dry formulation had the highest encapsulation efficiency because PBS was used in the washing step instead of water. This shows the importance of using aqueous processing streams with similar osmotic pressures to the release buffer.

The burst release of all three formulations are not significantly different. This is very different from the results given by Kim & Park for microparticles produced using traditional methods [Kim, T.; Park, T. Critical effect of freezing/freeze-drying on sustained release of FITC-dextran encapsulated within PLGA microspheres. *Int. J. Pharm.* 2004, 271, 207-214.].

Example 8: Effect of Annealing Microparticles at Elevated Temperatures

Microparticles were made as given in Example 1 with a few minor changes. First, ice-cold PBS was used to wash the particles instead of ice-cold water. Second, after freeze drying the dry microparticles were annealed at 60° C. for 1 hr, followed by slow cooling back to room temperature over another hour. The burst release from the annealed particles was measured as given in Example 1.

Results:

The annealed particles had an encapsulation efficiency of 89% and a burst release of 83%. As described for Example 7, the encapsulation efficiency is greater than that of Example 1 because greater care was taken to ensure that all washing steps were conducted cold, and because PBS was used to wash the particles instead of water. The burst release was even greater after annealing than the formulation in Example 1 or any of the formulations given in Example 7. This is counterintuitive because others have used annealing to close pores within the particle which suggests that annealing should decrease burst in particles made through traditional methods [Reinhold, S. E.; Desai, K. H.; Zhang, L.; Olsen, K. F.; Schwendeman, S. P. Self-Healing Microencapsulation of Biomacromolecules without Organic Solvents. *Angew. Chem.-Int. Edit.* 2012, 51, 10800-10803.].

Example 9: Effect of Annealing on Particles Containing a Plasticizer

Microparticles were produced as given in Example 1, with the addition of tributyl acetylcitrate (TBAC) to the DCM phase of the N/O/W emulsion such that the final microparticles were 16.7 wt % TBAC (20 wt % of hydrophobic material in the formulation is TBAC, 80 wt % is PLA). The No Annealing microparticles were washed and freeze dried as given in Example 1. The Annealed microparticles were washed with ice-cold PBS instead of water, freeze dried, and annealed as given in Example 8.

Results:

The No Annealing microparticles had an encapsulation efficiency of 74% and a burst release of 38%. The Annealed microparticles had an encapsulation efficiency of 90% and a burst release of 73%. Once again, the higher encapsulation efficiency of the Annealed microparticles is due to the use of PBS in the washes instead of water. Similar to Example 8, annealing resulted in more burst release.

Example 10: Effect of Release Temperature

Microparticles were made as given in Example 1, with the exception that the washes were conducted with ice-cold PBS instead of ice-cold water. The particles were not dried in any way and instead release was conducted immediately after washing, as done for the No Dry sample in Example 7. The release was carried out at room temperature (RT release), ~23° C. as opposed to 37° C. which was used for all previous examples.

Results:

The microparticles had an encapsulation efficiency of 85% and a burst release of 12%. This is much lower than the burst release of the No Dry particles in Example 7 (58%), which were produced exactly the same way but were kept at 37° C. to measure release. This shows that burst is higher at higher temperatures. This is the opposite of the observation of Kang and Schwendeman [Kang, J.; Schwendeman, S. P. Pore Closing and Opening in Biodegradable Polymers and Their Effect on the Controlled Release of Proteins. *Mol. Pharmaceutics* 2007, 4, 104-118.]. The hydrated glass transition temperature of PLA is less than 37° C. [Shah, S.; Cha, Y.; Pitt, C. Poly(glycolic Acid-Co-Dl-Lactic Acid)—Diffusion Or Degradation Controlled Drug Delivery. *J. Controlled Release* 1992, 18, 261-270.]. Therefore, in this example, at 37° C. rearrangements of the PLA within the microparticles are causing higher levels of burst release.

Example 11: Effect of Release Temperature on Highly Loaded Microparticles

The first set of highly loaded microparticles were made as given in Example 1, with the exception that 15 mg/mL of PEP1 was included in the iFNP process solvent stream instead of 5 mg/mL. Everything else was the same, including the release conditions at 37° C.

A second set of highly loaded microparticles were produced with some minor process changes. The microparticles were washed with ice-cold PBS instead of ice-cold water, and the release was started immediately after washing without any drying step. In addition, the release was conducted at room temperature (~23° C.) instead of 37° C.

Results:

The first set of highly loaded microparticles had an encapsulation efficiency of 93% and a burst release of 67%. The second set of highly loaded microparticles had an encapsulation efficiency of 94% and a burst release of 3%. This is similar to the result described in Example 10. The hydrated glass transition temperature of PLA is less than 37° C. [Shah, S.; Cha, Y.; Pitt, C. Poly(glycolic Acid-Co-Dl-Lactic Acid)—Diffusion Or Degradation Controlled Drug Delivery. *J. Controlled Release* 1992, 18, 261-270.]. Therefore, at 37° C. rearrangements of the PLA within the microparticles are causing higher levels of burst release.

Example 12: Effect of PLA Homopolymer Bulking Agent on Microparticles with No Drying Crosslinked nanoparticles were produced by iFNP as given in Example 1, with the exception that 15 mg/mL of PEP1 was included in the iFNP process solvent stream instead of 5 mg/mL. The nanoparticles were processed as given in Example 1. The nanoparticles were assembled into microparticles as given in Example 1, however the DCM phase contained 9 mg/mL of nanoparticles and 8.2 mg/mL of PLA homopolymer. The PLA glue (or bulking agent) was either 5 kDa or 40 kDa. The microparticles were made and processed as given in Example 1, with the exception that the particles were washed with ice-cold PBS instead of water, and that release was measured at 37° C. immediately after washing without a drying step.

Results:

The particles made with 5 kDa PLA glue had an encapsulation efficiency of 98% and a burst release of 0.7%. The particles made with 40 kDa PLA glue had an encapsulation efficiency of 98% and a burst release of 1.6%. The addition of a large amount of bulking agent caused the microparticles to have a very high encapsulation efficiency and a very low burst release. The low burst release was measured even though release was carried out at 37° C., above the hydrated glass transition temperature of the PLA.

Example 13: Effect of Bulking Agent on Microparticles with Freeze Drying

The first set of microparticles (47.6 wt % PLA homopolymer) were produced using the method given in Example 12 with a 5 kDa PLA bulking agent with a few minor changes. The microparticles were washed with ice-cold water instead of ice cold PBS, and the microparticles were freeze dried before measuring burst release at 37° C. A second set of microparticles were made with half the amount of bulking agent (4.1 mg/mL in the DCM phase of the N/O/W emulsion, 31.1 wt % PLA homopolymer in the final microparticle). All else was the same as the first set of microparticles.

Results:

The particles made with 47.6 wt % glue had an encapsulation efficiency of 96% and a burst release of 3%. The particles made with 31.1 wt % glue had an encapsulation efficiency of 96% and a burst release of 12%. The burst release decreased with increasing amounts of PLA homopolymer bulking agent or glue.

Example 14: Effect of the Crosslinking Strength and the Osmolarity of the Water Phase in the N/O/W Emulsion Process on Microparticle Encapsulation Efficiency and Burst Release Inverted nanoparticles loaded with PEP1, a ~30 amino acid long peptide, were produced by inverse Flash Nano- Precipitation (iFNP). The process solvent stream was 500 μL of dimethyl sulfoxide (DMSO) with 5 v % water. The process solvent stream contained 5 mg/mL PEP1 and 5 mg/mL poly(aspartic acid) (5 kDa)-b-poly(lactic acid) (10 kDa)-b-poly(aspartic acid) (5 kDa) (PAsp(5 kDa)-b-PLA(10 kDa)-b-PAsp(5 k Da)). The PEP1 was tagged (~1% tagged) with Alexa Fluor 488. The non-process solvent was 600 μL of dichloromethane (DCM) with 50 μL of methanol (MeOH) containing $CaCl_2$). The calcium cations crosslink the PAsp block of the stabilizing polymer. The process solvent and non-process solvent streams were rapidly mixed in a confined impingement jets (CIJ) mixer, and the effluent was collected in 4 mL of DCM. The calcium to aspartic acid charge ratio was 1.2 to 1 in the final solution. After nanoparticle assembly, 100 μL of an ammonium hydroxide in MeOH solution was slowly added to the inverted nanoparticles to strengthen the crosslinking. Some formulations were made without any added ammonia hydroxide ("Weak Crosslinking"). The resulting inverted nanoparticles were ~100 nm in diameter in DCM.

After the inverted nanoparticles had been crosslinked for 30 min, the DMSO was extracted with 1.67 mL of 10 wt % NaCl in water (1:3 water:organic by volume) by inverting 5 times and then gently shaking for 30 min. The high density DCM phase containing the inverted nanoparticles was removed, and the brine phase was saved to measure the amount of extracted PEP1. The inverted nanoparticles were concentrated to 10 mg/mL by rotary evaporating. A separate solution of 11 kDa PLA was produced in DCM at a mass concentration of 10 mg/mL.

The inverted nanoparticle dispersion and PLA homopolymer solution were mixed at different ratios to produce mixtures that contained 10 mg/mL of total solids, with 25, 50, or 75 wt % of those solids being nanoparticles.

The inverted nanoparticle/PLA solution (50 μL) was added to the bottom of 6 mL of 1, 2.5, 5, or 10 wt % NaCl with 1 wt % polyvinyl alcohol (PVA, 98% hydrolyzed) in a glass scintillation vial. A nanoparticle-in-oil-in-water (N/O/W) emulsion was formed by gently swirling the vial ten times in a circular motion. After emulsification, the DCM was removed by rotary evaporation at 20° C. and 200 torr for 10 min, followed by 100 torr for 20 min, producing hardened microparticles.

After solvent removal, the microparticle dispersion was moved to a glass test tube with a PTFE-lined cap and kept cold on ice until washed (no longer than an hour). Prior to washing, the particles were centrifuged at 200 rcf for 10 min, and the supernatant was removed and analyzed for unencapsulated PEP1 by fluorescence. The particles were resuspended in 3 mL of water and then centrifuged a second time. The supernatant was removed and the washing step was repeated twice more. The three washes for each formulation were combined and analyzed for unencapsulated PEP1 by fluorescence. The microparticles were frozen on dry ice in ~1 mL of water and lyophilized overnight. The microparticle formulations made are given in Table 1, below.

TABLE 1

Small scale microparticle formulations. Nanoparticle loading is the wt % of nanoparticle in the final microparticle. The remaining mass is PLA homopolymer. The PEP1 target loading is the wt % of PEP1 in the particle if 100% encapsulation efficiency was achieved.

| Nanoparticle Loading | Target PEP1 Loading | N/O/W Water Phase NaCl Content | Crosslinking |
|---|---|---|---|
| 25% | 12.5% | 1 wt % | Strong |
| 25% | 12.5% | 5 wt % | Strong |
| 50% | 25% | 1 wt % | Strong |
| 50% | 25% | 2.5 wt % | Strong |
| 50% | 25% | 5 wt % | Strong |
| 50% | 25% | 10 wt % | Strong |
| 75% | 37.5% | 1 wt % | Strong |
| 75% | 37.5% | 5 wt % | Strong |
| 50% | 25% | 1 wt % | Weak |
| 50% | 25% | 5 wt % | Weak |

The losses were quantified from three separate steps: the brine extraction, emulsification and washing. The brine extraction losses were always low (<3%) and will not be discussed. The majority of PEP1 losses occurred in the emulsification and washing steps. All washing steps were done with pure water, independent of the water phase used in the N/O/W emulsion. All losses were calculated as the percent of PEP1 lost with respect to the starting amount of PEP1.

Burst release was measured from the freeze dried microparticles by adding 5 mL of PBS with 0.02 wt % Tween 20 and 0.02 wt % $NaN_3$. The release sample was protected from light using aluminum foil and placed in a forced air incubator with set to 37° C. with a shaking speed of 125 rpm. To measure the amount of release PEP1, the microparticles were centrifuged from solution at 200 rcf for 10 min, and 1 mL of the aqueous phase was removed. If the sample was not immediately analyzed, it was frozen at −20° C. until the time of analysis. The amount of PEP1 released was determined by fluorescence. The burst release was measured as the amount released after 48 hrs. The percent release was calculated as the percent released with respect to the amount encapsulated.

Figure 11:
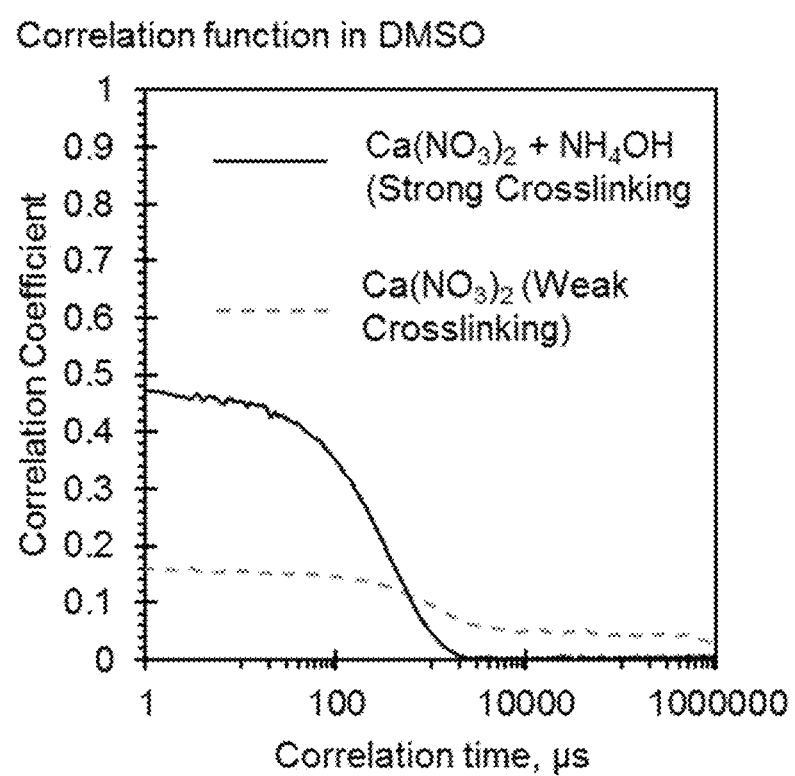

Results:

The inverted nanoparticles crosslinked without ammonia present were clearly more weakly crosslinked than the inverted nanoparticles crosslinked with ammonia present (FIG. 11). In FIG. 11 this is observed as a weaker correlation function in DMSO, a solvent that would dissolve the nanoparticles if no crosslinking had occurred.

Figure 12A:
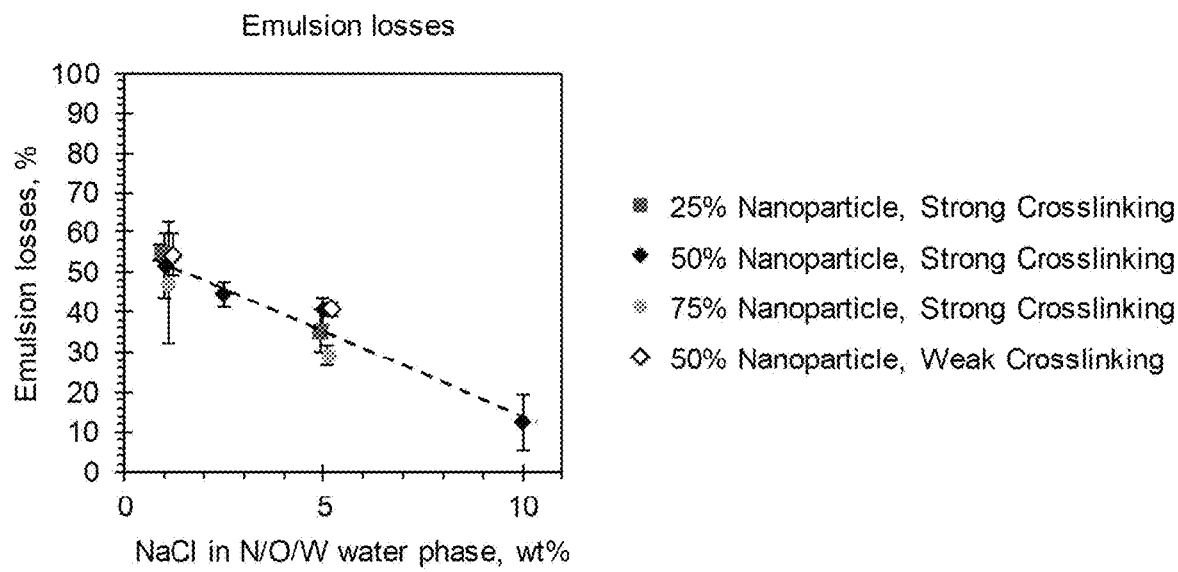
FIG. 12C shows the total losses of an encapsulated peptide (during emulsification and during microparticle washing). Details of the formulations are provided in Example 14.

The emulsification losses decreased as the brine content of the water phase increased (FIG. 12A). The losses were ~50% for 1 wt % brine and ~10% for 1 wt % brine. Higher brine contents means higher osmolarity and less swelling of the inverted nanoparticle core. The amount of glue (higher % nanoparticle means lower % PLA homopolymer glue) did not seem to have a major effect on the emulsion losses. This may be because the hydrophobic PLA block of the stabilizing polymer was very small (10 kDa) and the majority of the losses were due to the use of a short hydrophobic block. Higher emulsification losses were observed in the Weak Crosslinking formulations.

Figure 12B:
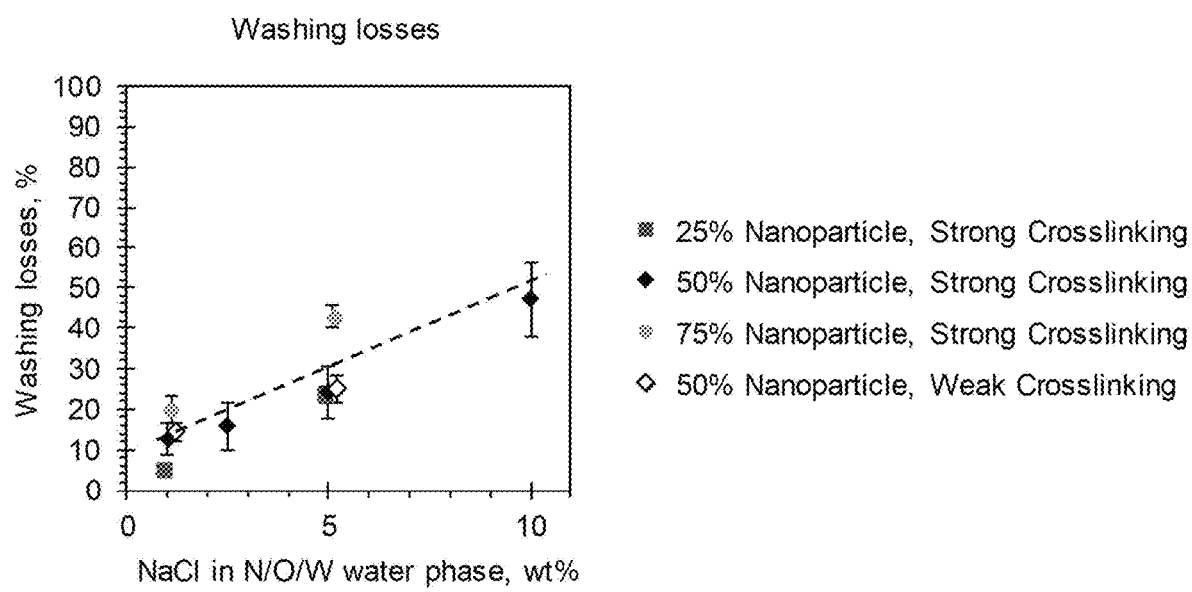

Microparticles produced with higher brine contents in the N/O/W emulsion process had higher losses during washing (FIG. 12B). The washing with pure water caused particles that had previously been exposed to high brine contents to swell, resulting in greater washing losses. Particles that were made with lower brine contents were more osmotically equilibrated to the water washes, resulting in lower washing losses.

Figure 12C:
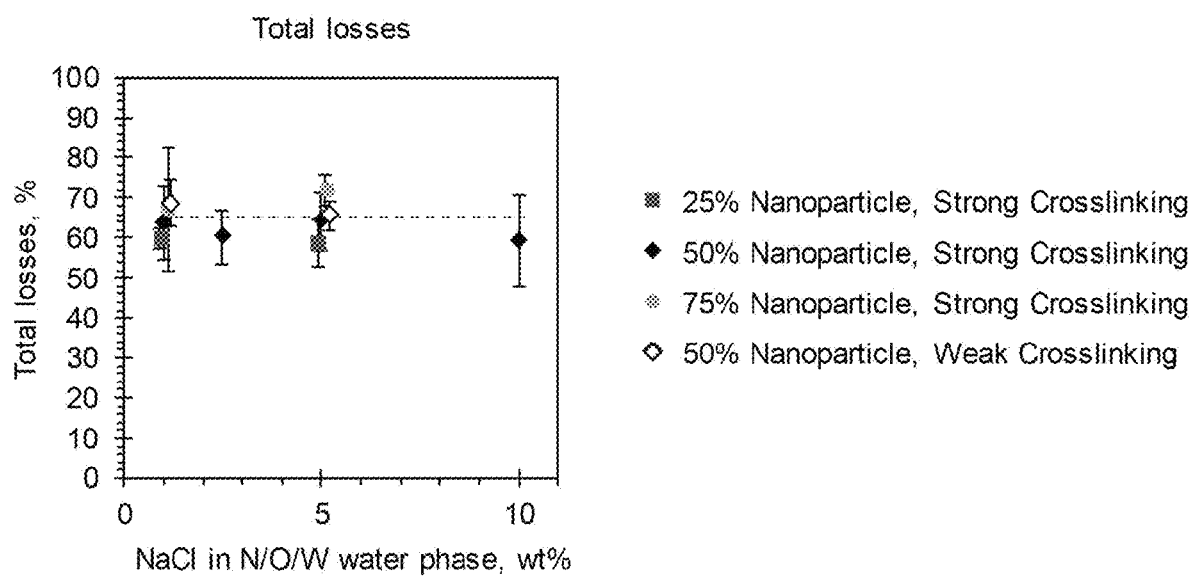

In general, the total losses were consistent around 65% (FIG. 12C), corresponding to an encapsulation efficiency of ~35%. This is much lower than the previous example because of the low molecular weight of the hydrophobic PLA block of the stabilizing polymer.

The burst release from each formulation is given in Table 2. For the strongly crosslinked particles, the burst release was lowest for particles made using water phases with a similar osmolarity to the PBS release buffer (the 1 wt % brine). This supports that for low burst, particles should be processed in aqueous phases with similar osmolarities to the final release media.

TABLE 2

The burst release from small scale microparticle formulations. Nanoparticle loading is the wt % of nanoparticle in the final microparticle. The remaining mass is PLA homopolymer. The PEP1 target loading is the wt % of PEP1 in the particle if 100% encapsulation efficiency was achieved. The percent released is the percent of the encapsulated PEP1 (accounting for all losses).

| Nanoparticle Loading | N/O/W Water Phase NaCl Content | Crosslinking | Burst Release |
|---|---|---|---|
| 25% | 1 wt % | Strong | 12% |
| 25% | 5 wt % | Strong | 37% |
| 50% | 1 wt % | Strong | 36% |
| 50% | 2.5 wt % | Strong | 39% |
| 50% | 5 wt % | Strong | 42% |
| 50% | 10 wt % | Strong | 55% |
| 75% | 1 wt % | Strong | 29% |
| 75% | 5 wt % | Strong | 43% |
| 50% | 1 wt % | Weak | 83% |
| 50% | 5 wt % | Weak | 77% |

The burst release was lowest with the highest amount of PLA homopolymer bulking agent or glue (lowest nanoparticle loading). The burst release was the highest for the weakly crosslinked particles. Strong crosslinking enables low burst release by creating an added diffusion barrier to slow release and by holding the soluble portions of the final microparticle together in aqueous conditions.

Example 15: Nanoparticle Assembly in Layer-by-Layer Process

Hydrophilic therapeutic (vancomycin, lysozyme, etc.) with around 5 mol % labeling by AlexaFluor-488 was dissolved in dimethyl sulfoxide (DMSO) at 12.5 mg/ml. A block copolymer of $PAsp_{5k}$-$PLA_x$-$PAsp_{5k}$ was dissolved at 12.5-20 mg/ml in DMSO where x was 10 kDa, 20 kDa, or 40 kDa as noted. A DMSO solution containing 5 vol % water was prepared such that it contained the desired ratio of biologic to polymer (typically 30-50 wt % biologic) with the mass of the polymer and the biologic totaling 10 mg/ml. An equal volume of an antisolvent stream of chloroform for lysozyme or dichloromethane for vancomycin was prepared. These streams were mixed in an FNP process using a CIJ mixer and collected in a vial containing additional chloroform (dichloromethane for vancomycin) such that the final DMSO content was 10 vol %. This forms a core-shell nanoparticle structure where the biologic comprises the core of the particle with the PAspA and is stabilized by a PLA corona.

If metal crosslinking was employed, this was included as a solution in methanol that was added to the antisolvent stream. The methanol concentration was such that a 50 μL volume added to the antisolvent afforded a 1:1 charge ratio of the positive charge from the cation to the negative charge from the PAspA residue sidechains. If crosslinking strength was modulated by pH modification, this was done by preparing a solution of ammonia in methanol such that a 50 μL volume afforded 0.6 equivalents with respect to the PAspA sidechain groups. This solution was added to the nanoparticle solution after the inverse nanoparticles were produced by dropwise addition to a rapidly stirred vial. The solution was then aged for 30 minutes to permit crosslinking of the PAspA core.

If crosslinking with an organic polycation was employed, a solution of tetraethylene pentamine (TEPA) in chloroform at 5 mg/ml was added dropwise to the nanoparticle solution under rapid stirring. The volume added was defined such that 0.7 eq of TEPA was delivered per acid residue on the PAspA input. The solution was then aged for 30 minutes. At each process step, particle size was measured by dynamic light scattering using a Zetasizer Nano ZS (Malvern, Worcestershire, UK) at 25° C. by diluting each sample ten-fold with the corresponding solvent.

To remove the DMSO, a 150 mM solution of NaCl in water or a phosphate buffered saline (PBS) at pH 7.3 was gently added to the nanoparticle solution such that the aqueous volume was half the chloroform volume. This extraction was carried out on a shaker table for 30 minutes at room temperature. The aqueous layer was separated from the nanoparticle solution. In all cases reported below, the losses to this extraction were less than 4%.

A diblock copolymer $PLA_{5kDa}$-b-$PEG_{5kDa}$ was added at a defined ratio with respect to the mass of inverse nanoparticle (typically 0.5 to 2). An equal volume of acetone or THF was added to the chloroform or DCM. The nanoparticle solution was then solvent swapped into acetone or THF. Typically, this involved a put-and-take distillation by rotovap with 7-8 ml added four times before evaporation to a total mass concentration of 5-7.5 mg/ml each time. The solution of nanoparticles in acetone was then mixed in a second FNP step using a CIJ against an equal volume of deionized water. The mixed stream was collected in a vial containing additional deionized water such that the final solution contained 10 vol % acetone (or THF).

Residual acetone and unencapsulated biologic were removed by rinsing on a 100 kDa Amicon ultrafilter that had been pre-blocked to prevent non-specific adsorption. The nanoparticle solution was concentrated to around 15-20 mg/ml and rinsed with deionized water twice using a volume that was about 3-4 times the concentrated volume. The flow-through streams were analyzed by fluorescence to determine encapsulation efficiency. The nanoparticles were resuspended in the indicated release buffer and placed on a shaker table at 37° C. for release. Aliquots were taken as indicated and the released fraction was determined by fluorescence measurement on soluble biologic that had been separated from the nanoparticle using a pre-treated 100 kDa ultrafilter. Particle size was characterized by Dynamic Light Scattering (DLS) using a Zetasizer Nano ZS.

Example 16: Osmotic Pressure in Extraction & Coating Effects for Vancomycin Nanoparticles The osmotic pressure throughout the processing steps must be carefully maintained to control the encapsulation efficiency (EE) in the final coating step. This is demonstrated by the following examples.

Vancomycin was encapsulated in nanoparticles with the layer-by-layer process at 50% loading as described in Example 15 to produce samples V1-4 in Table 3. The particles were crosslinked with calcium. The extraction was either PBS (V4) or a solution of NaCl in water ("brine") at 13 wt % (V1-3). The solvent swap was carried out in THF and the coating ratio was varied as noted in Table 3.

The particles produced at a 1.5:1 ratio were 120 nm (brine) or 150 nm (PBS) with polydispersity index (PDI) values of around 0.2. The use of the 13 wt % brine resulted in an encapsulation efficiency (EE) of less than 6% whereas the use of PBS in the extraction produced an EE of 29%. Without being bound by theory, the equilibration of the particles with a high osmotic pressure during the extraction may result in disruption of the particle shell when coated in an aqueous environment of lower osmotic pressure. The larger size after coating of the particles from the PBS extraction reflects differences in the particle size input to the coating step rather than swelling during coating. Further, the low EE values from the brine extraction were not mitigated by varying the polymer coating ratio. The results were essentially identical whether no PLA-PEG was added or a 1.5:1 ratio was used (samples V1-3).

Example 17: Crosslinking Strength Modification with Metal Crosslinkers for Vancomycin Crosslinking of the particle core is important for stability and processability in later steps, as illustrated in this example.

Figure 13:
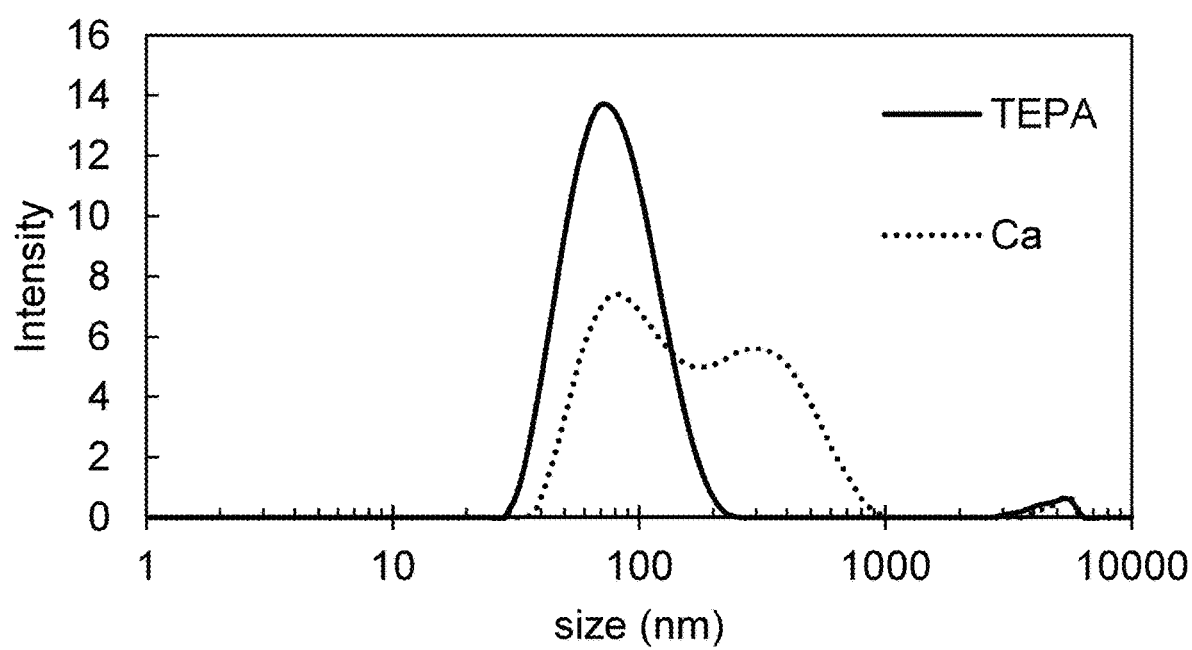
FIG. 13 is a dynamic light scattering (DLS) analysis of vancomycin particles after a solvent swap into acetone. A clear aggregation population is visible for calcium-cross-linked particles (Ca) while the TEPA-crosslinked particles remained relatively monodisperse.
Figure 14:
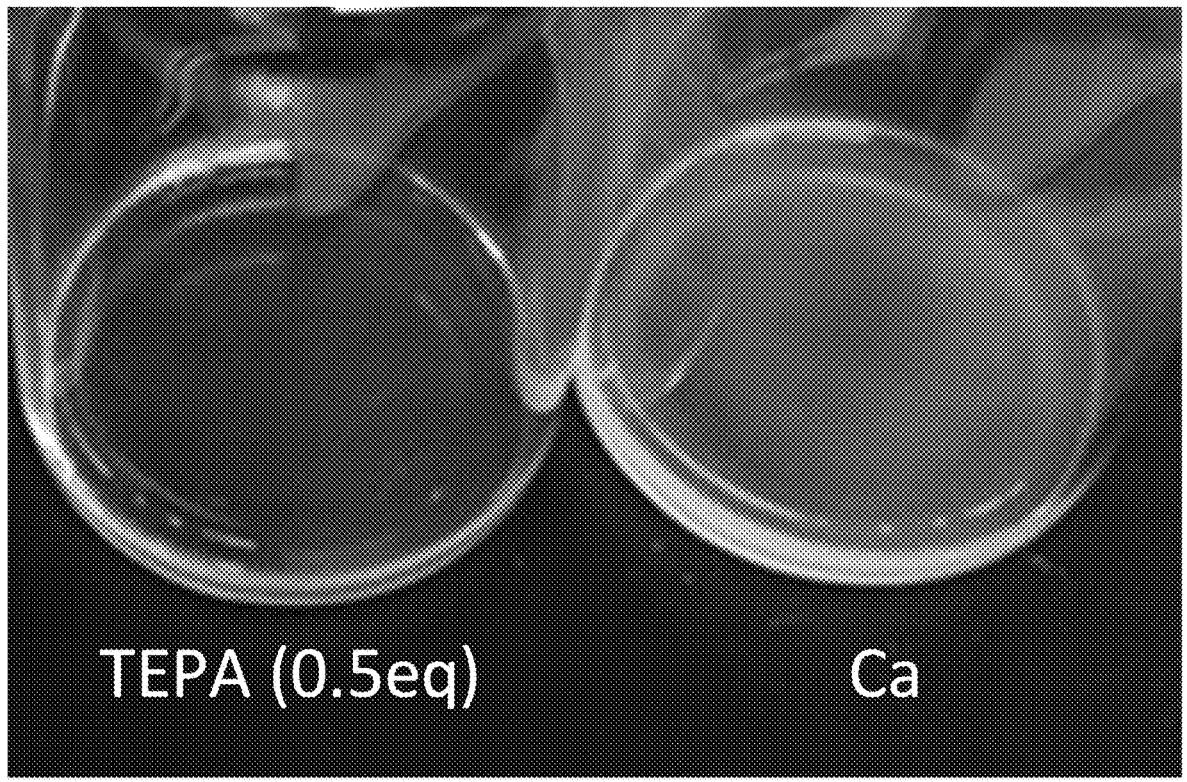
FIG. 14 is a photograph of nanoparticle solutions following completion of the solvent swap. Nanoparticles cross-linked with TEPA remained dispersed as nanoparticles in a clear solution (left) while calcium crosslinking led to visible aggregation that formed a cloudy solution (right).

Vancomycin particles were prepared at 50% loading according to Example 15 with a poly(styrene)$_5$-b-poly(acrylic acid)$_{4.8}$ copolymer stabilizer. The particles were either crosslinked with calcium and ammonia or with TEPA. Following the solvent exchange into THF, the particle size distribution was assessed by DLS as shown in FIG. 13. The data support the visual observation of extensive aggregation across a range of length scales. To confirm the observations with a degradable polymer, particles were prepared according to Example 15 using a copolymer with a PLA block size of 10 kDa and a loading of 50%. The particles were crosslinked with either TEPA (0.5 equivalents) (sample V5) and compared with calcium-crosslinked particles described above (V4). The physical behavior in the solvent exchange was identical, with visible aggregation for the calcium-crosslinked sample resulting in a cloudy solution. The TEPA-crosslinked nanoparticles remained as a clear solution with dispersed nanoparticles as illustrated by FIG. 14. DLS analysis in DMSO, which should dissolve uncrosslinked particles, showed that the TEPA-crosslinked particles were resistant to swelling in the solvent while the calcium particles were confirmed to be weakly crosslinked in two ways. First, the automatic attenuator selection indicated very low light scattering (maximum attenuator). Second, the correlation function did not exhibit the expected monotonic decay over a narrow measurement window.

The generalizability of this observation is bolstered by the following results: reducing the TEPA equivalents to produce fewer crosslinks in the particle core led to extensive aggregation in the solvent swap. DLS analysis of samples with and without ammonia showed greater aggregation after the solvent swap without ammonia. Metal-crosslinked particles without ammonia have weaker crosslinking due to fewer physical crosslinks. The DLS PDI values were similar, but a clear shift towards higher particle populations was visible in the distribution data. Finally, the same trend was observed with lysozyme nanoparticles, where DLS analysis showing weak crosslinking (maximum attenuator and non-monotonic correlation function) correlated with instability during the solvent swap.

These results indicate that crosslinking strength can be an important variable for successful nanoparticle processing. Aggregation during the solvent swap may or may not be reversible during the final step to coat the nanoparticles with PEG. The aggregation process may be unpredictable and highly susceptible to variations in process conditions. Thus, reproducible formulations require robust crosslinking such that particle size is not variable during the process steps. Different formulations may have different crosslinking strengths that provide sufficient robustness. Without being bound by theory or the examples provided herein, there are a number of variables that may influence what this crosslink strength threshold is, such as propensity towards swelling, amphiphilicity of the encapsulated material, specific interactions of the encapsulated material with the core polymer, or hydrophobic block size. Sufficient crosslinking strength in the nanoparticle process is best assessed by screening crosslinkers with and without ammonia to increase crosslink extent. DLS of the particles in a good solvent will indicate the strength of crosslinking and DLS analysis after the solvent swap will indicate size stability.

It should also be noted that improved crosslinking with TEPA led to reduced EE for vancomycin formulations (18% versus 29% with calcium crosslinking). Without being bound by theory, we hypothesize that this reflects greater exposed nanoparticle surface area in the unaggregated samples that promotes loss of the biologic during coating. Given the propensity for poor crosslinking to lead to aggregation in nanoparticle processing, it is difficult to further assess its effect on EE or burst release.

Example 18: HRP Nanoparticle Formulations

Horseradish peroxidase (HRP) was encapsulated in a layer-by-layer process. HRP was dissolved in dimethyl sulfoxide (DMSO) at 12.5 mg/ml. A block copolymer of PAsp$_{5k}$-PLA$_{10k}$-PAsp$_{5k}$ was dissolved at 12.5 mg/ml in DMSO. A solution of DMSO containing 10 vol % water was prepared such that HRP and the copolymer were present at 10 mg/ml total mass concentration in a 1:1 mass ratio (50% loading). The stream was mixed against an equal volume of a solution of DCM containing 10% methanol and calcium chloride at a 1:1 charge ratio with the acid monomers in the PAsp block. The nanoparticle solution was collected in a bath of additional DCM such that the final solution contained 10% DMSO by volume.

To strengthen the PAsp crosslinking, a 50 µL volume of a solution of ammonia in methanol was added with a concentration such that it afforded 0.6 equivalents with respect to the PAspA sidechain groups. This solution was added to the nanoparticle solution after the inverse nanoparticles were produced by dropwise addition to a rapidly stirred vial. The solution was then aged for 30 minutes to permit crosslinking of the PAsp core.

To remove the DMSO, 3 ml of a 150 mM solution of NaCl in water was gently added to the nanoparticle solution. This extraction was carried out on a shaker table for 30 minutes at room temperature. The aqueous layer was separated from the nanoparticle solution. A diblock copolymer PLA$_{5kDa}$-b-PEG$_{5kDa}$ was added at a 0.5:1 ratio with respect to the mass of inverse nanoparticle. An equal volume of acetone was added to the DCM. The nanoparticle solution was then solvent swapped into acetone by put-and-take distillation by rotovap with 7-8 ml added three times before evaporation to a total mass concentration of 5 mg/ml each time. The solution of nanoparticles in acetone was then mixed in a second FNP step using a CIJ against an equal volume of deionized water. The mixed stream was collected in a vial containing additional deionized water such that the final solution contained 11 vol % acetone.

Residual acetone and unencapsulated biologic were removed by rinsing on a 100 kDa Amicon ultrafilter. The flowthrough was assayed by the bicinchoninic acid (BCA) assay and corrected for known filter losses to afford the EE. The results are summarized as sample H1 in Table 3.

Example 19: OVA Nanoparticle Formulations for EE with Incorporation of a Small Molecule Hydrophobic Compound in the Coating Step Processing solvents and additives can influence the EE in the final process step as illustrated by these examples using chicken ovalbumin (OVA).

OVA was dissolved in deionized water at 50 mg/ml. It was diluted to 5 mg/ml with DMSO. A solution of $PAsp_{5k}$-$PLA_{10k}$-$PAsp_{5k}$ was prepared at 8 mg/ml in DMSO. The OVA solution was mixed with the polymer solution, THF, and chloroform at volume ratios of 1:1:1:2.5 respectively in a MIVM. The solution was diluted further with chloroform at 1.3 times the processed volume. A solution of calcium chloride in methanol was added such that there was a 2:1 charge ratio of the cation to the acid groups in PAsp. A solution of ammonia in methanol was added such there were 0.6 equivalents with respect to the acid groups on PAsp. The solution was aged for 30 minutes to permit crosslinking. Nanoparticle size distributions were measured as needed using a Malvern Zetasizer ZS.

A volume of 150 mM NaCl in water solution equal to half the nanoparticle solution volume was added gently. The biphasic extraction was carried out with gentle agitation for 30 minutes. A solvent swap into acetone (samples E1-E3) or THF (sample E4) was carried out as described above with a final concentration of 5 mg/ml nanoparticles.

The nanoparticle solution post-swap was processed as follows. $PLA_{5k}$-b-$PEG_{5k}$ was added at a 1:1 mass ratio with the nanoparticle (biologic+polymer). Sample E1 was mixed rapidly in a CIJ against phosphate buffered saline (PBS) at equal volume and diluted with PBS such that the final concentration of acetone was 10 vol %. Samples E2 and E4 were mixed rapidly in a CIJ against deionized water and diluted with water to a final acetone concentration of 10 vol %. To sample E3, α-tocopherol (vitamin E) was added at an equal mass to the PLA-PEG. This solution was rapidly mixed in a CIJ against deionized water and diluted further to 10 vol % acetone. The samples were rinsed on a 10 k ultrafilter to remove residual acetone. The unencapsulated OVA was then separated from the nanoparticles using a 300 kDa ultrafilter.

Figure 15:
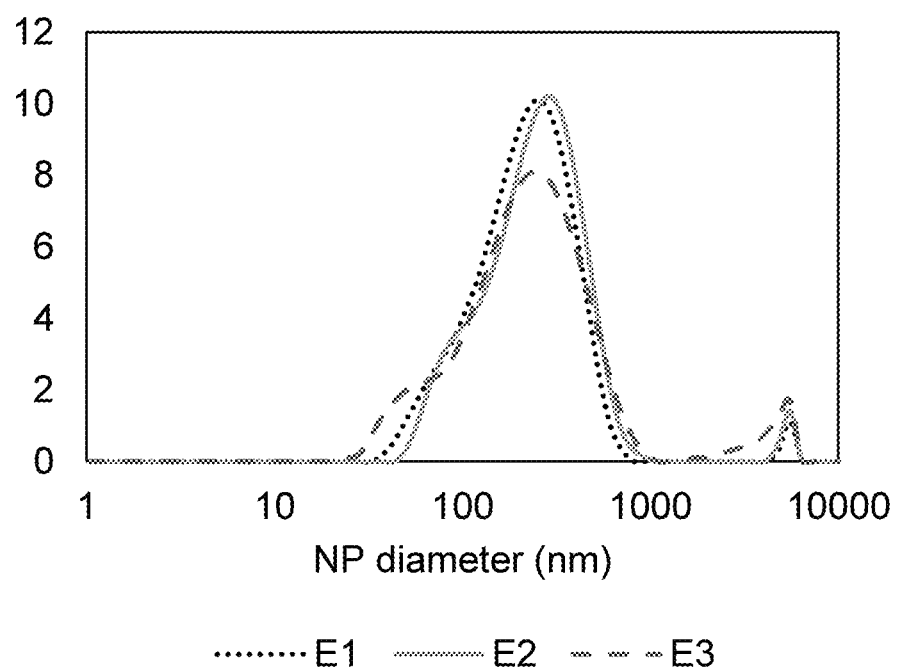
FIG. 15 gives DLS size distributions of OVA formulations showing a primary coated nanoparticle population at around 200 nm and a small lead shoulder population corresponding to empty nanoparticles. In E3, with the addition of vitamin E, the empty nanoparticle population becomes significantly more pronounced likely due to partitioning of the hydrophobic compound into these particles.

The unencapsulated OVA concentration was then determined by BCA assay correcting for adsorption losses. The EE values are listed in Table 3. The use of PBS as a coating antisolvent resulted in higher EE (83% vs 78%) as a result of reduced swelling from osmotic pressure. Addition of vitamin E had an only minor effect, increasing the EE from 78% to 79% and is likely due to partitioning of vitamin E into empty nanoparticles. See FIG. 15 for DLS size distributions that illustrate this increased small nanoparticle population. The broad nature of the distributions is a result of using a separate PLA-PEG coating polymer. A measurable fraction went to empty nanoparticles, or—in the case of vitamin E—to nanoparticles containing a portion of the vitamin E. The experimental techniques used are not able to distinguish the fraction of vitamin E localized in biologic-containing nanoparticles or not. Sample E4 illustrates that process solvent can modify encapsulation efficiency, where the use of THF led to 8 percentage points higher value than acetone. Without being bound by theory, the mechanism of this change may be due to preferential interactions of portions of the protein with one solvent compared to the other (leading to greater localization at the interface and ready solubilization in the coating step) or differences in hydrophobic shell structure and mobility leading to different hydrophobic shell barrier quality.

Example 20: Release Buffer and Specific Interactions of Lysozyme in Nanoparticles Specific interactions with the biologic and the polymer can influence EE and modify burst release propensity as illustrated by these examples involving lysozyme.

Lysozyme nanoparticles were prepared according to the method in Example 15. A polymer with a 40 kDa PLA block was used and TEPA crosslinking was carried out. An extraction with 150 mM NaCl in water was carried out and the coating polymer ratio was 0.5:1 with respect to the inverse nanoparticle mass. The solvent swap into acetone afforded a solution at 7.5 mg/ml. This was then rapidly mixed in a CIJ against water and diluted further to 10% acetone by volume.

Figure 16:
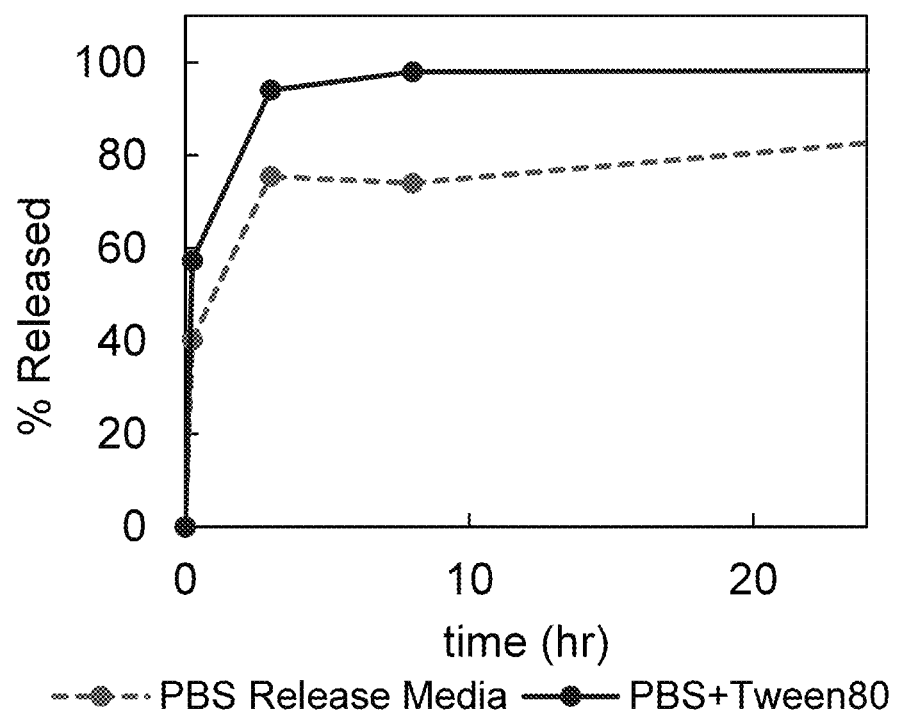
FIG. 16 shows the burst release of lysozyme in phosphate buffered saline (PBS) or PBS with 0.2 wt % Tween-20 release media. The presence of a surfactant speeds release by 25% and suggests that hydrophobic interactions partially mediate the release rate.

After two water rinses, the nanoparticle solution was split such that a release study was carried out in either PBS or PBS with 0.2 wt % Tween-20 added. The encapsulation efficiency was calculated by measuring the flow through from the nanoparticle solution and washes. The encapsulation efficiency was very high at 98% as seen in Table 3 for sample L1. This is a result of the specific ionic interactions that occur between the positively-charged lysozyme and the negative PAsp in the particle core. There is no release when the nanoparticles are incubated in water or in an isotonic sugar solution. However, release is observed when the release media contains salt ions. The burst release data are captured in FIG. 16. These data show that the release is mediated not only by ionic interactions but also by hydrophobic interactions since the burst is 25% greater in the presence of a non-ionic surfactant (polysorbate).

TABLE 3

Nanoparticle Formulation Summary

| Name | Example | Biologic | PLA MW | PLA-PEG ratio | EE |
|---|---|---|---|---|---|
| V1 | 16-brine | Vanc | 10k | 0 | 4.7 |
| V2 | 16-brine | Vanc | 10k | 1 | 4.2 |
| V3 | 16-brine | Vanc | 10k | 1.5 | 5.5 |
| V4 | 16-PBS | Vanc | 10k | 1.5 | 29 |
| V5 | 17-TEPA | Vanc | 10k | 1.5 | 18 |
| H1 | 18 | HRP | 10k | 0.5 | 74 |
| E1 | 19 | OVA | 10k | 1 | 83 |
| E2 | 19 | OVA | 10k | 1 | 78 |
| E3 | 19 | OVA | 10k | 1 | 79 |
| E4 | 19 | OVA | 10k | 1 | 86 |
| L1 | 20 | LYS | 40k | 0.5 | 98 |

Aspects of the Invention

Aspect 1. A method of forming a polymer inverse nanoparticle that encapsulates a water soluble active to maximize or optimize encapsulation efficiency and/or to minimize and/or optimize burst fraction, comprising:

dissolving the water soluble active at a concentration and a block copolymer at a concentration in an amount of a process solvent to form a process solution; and continuously mixing the process solution with an amount of a nonprocess solvent at a process temperature to form a first nanoparticle solution comprising polymer inverse nanoparticles having a core and a shell and a first nanoparticle solvent;

wherein the block copolymer comprises a hydrophilic block and a hydrophobic block having a glass transition temperature (Tg), wherein the hydrophilic block is soluble in the process solvent and is insoluble in the nonprocess solvent, wherein the hydrophobic block is insoluble in the process solvent and is soluble in the nonprocess solvent, wherein the process solution is more polar than the nonprocess solvent, wherein the water soluble active and the hydrophilic block are in the core and the hydrophobic block is in the shell, and wherein the encapsulation efficiency is maximized or optimized by
  (a) selecting the process solvent, so that the hydrophilic block is close to a solubility limit in the process solution for the concentration of the block copolymer, and/or
  (b) crosslinking the hydrophilic block in the core, and/or
  (c) selecting the hydrophilic block to have bonding interactions with the water soluble active in the core, and/or
  (d) selecting the hydrophobic block to have a molecular weight of at least 10 kDa, 20 kDa, 30 kDa, 40 kDa, 50 kDa, 70 kDa, or 100 kDa, and/or
  (e) selecting the process temperature and/or the hydrophobic block, so that the process temperature is less than the hydrophobic block glass transition temperature (Tg), and/or
  (f) selecting the process solvent to have high osmolarity (e.g., by dissolving a salt in the process solvent), and/or
  (g) adding a supplemental hydrophobic compound to the process solvent and/or to the nonprocess solvent to increase the bulk of hydrophobic material in the shell, and/or wherein the burst fraction is minimized or optimized by
  (aa) crosslinking the hydrophilic block in the core, and/or
  (bb) increasing the hydrophobic block glass transition temperature (Tg), and/or
  (cc) adding a supplemental hydrophobic compound to the process solvent and/or to the nonprocess solvent to increase the bulk of hydrophobic material in the shell.

Aspect 2. The method of Aspect 1, wherein the encapsulation efficiency is optimized by crosslinking the hydrophilic block in the core.

Aspect 3. The method of any one of Aspects 1 and 2, wherein the burst fraction is minimized by crosslinking the hydrophilic block in the core.

Aspect 4. The method of any one of Aspects 1 through 3, wherein the crosslinking agent is selected from the group consisting of a metal and calcium.

Aspect 5. The method of any one of Aspects 1 through 3, wherein the crosslinking agent is selected from the group consisting of a chelating agent and tetraethylene pentamine (TEPA).

Aspect 6. The method of any one of Aspects 1 through 5, wherein the encapsulation efficiency is maximized by adding a supplemental hydrophobic compound to the nonprocess solvent to increase the bulk of hydrophobic material in the shell.

Aspect 7. The method of any one of Aspects 1 through 6, wherein the burst fraction is minimized by adding a supplemental hydrophobic compound to the nonprocess solvent to increase the bulk of hydrophobic material in the shell.

Aspect 8. The method of any one of Aspects 6 and 7, wherein the supplemental hydrophobic compound is selected from the group consisting of a hydrophobic polymer and polylactic acid Aspect 9. The method of any one of Aspects 6 and 7, wherein the supplemental hydrophobic compound is vitamin E.

Aspect 10. The method of any one of Aspects 1 through 9, wherein the burst fraction is minimized by selecting the process temperature and/or the hydrophobic block, so that the process temperature is less than the hydrophobic block glass transition temperature (Tg).

Aspect 11. The method of any one of Aspects 1 through 10, further comprising annealing the polymer inverse nanoparticle.

Aspect 12. The method of Aspect 11, wherein the annealing maximizes the encapsulation efficiency.

Aspect 13. The method of Aspect 11, wherein the annealing optimizes the encapsulation efficiency.

Aspect 14. The method of any one of Aspects 1 through 13, further comprising adding lecithin to the nonprocess solvent.

Aspect 15. The method of any one of Aspects 1 through 15, wherein the water soluble active is selected from the group consisting of ovalbumin, lysozyme, and PEP1.

Aspect 16. The method of any one of Aspects 1 through 14, wherein the water soluble active is vancomycin Aspect 17. The method of any one of Aspects 1 through 16, wherein the water soluble active is selected from the group consisting of a linear polypeptide and a cyclic polypeptide.

Aspect 18. The method of any one of Aspects 1 through 17,
  wherein the hydrophilic block is selected from the group consisting of poly(aspartic acid) and poly(glutamic acid) and
  wherein the hydrophobic block is selected from the group consisting of poly(lactic acid), poly(lactic-co-glycolic acid), and poly(caprolactone).

Aspect 19. The method of any one of Aspects 1 through 17,
  wherein the hydrophilic block is of a molecular weight in the range of from 0.2 kDa to 100 kDa, from 0.5 kDa to 50 kDa, from 1 kDa to 20 kDa, from 2 kDa to 10 kDa, or of about 5 kDa, and
  wherein the hydrophobic block is of a molecular weight in the range of from 0.5 kDa to 400 kDa, 1 kDa to 200 kDa, from 2 kDa to 100 kDa, from 5 kDa to 100 kDa, from 10 kDa to 40 kDa, of about 10 kDa, of about 20 kDa, or of about 40 kDa.

Aspect 20. The method of any one of Aspects 1 through 19, wherein the supplemental hydrophobic compound is selected from the group consisting of poly(lactic acid), poly(lactic-co-glycolic acid), and poly(caprolactone).

Aspect 21. The method of any one of Aspects 1 through 20, wherein the process solvent is miscible with the nonprocess solvent.

Aspect 22. The method of any one of Aspects 1 through 21, further comprising
  adding a second block copolymer to the first nanoparticle solution to form a second stage process solution; and
  continuously mixing the second stage process solution with a finishing solvent to form a second nanoparticle solution comprising the polymer inverse nanoparticles coated with the second block copolymer,
  wherein the second block copolymer comprises a second hydrophilic block and a second hydrophobic block.

Aspect 23. The method of Aspect 22,
  wherein the second hydrophilic block is selected from the group consisting of poly(ethylene glycol) and poly(propylene oxide) and wherein the second hydrophobic block is selected from the group consisting of poly(lactic acid), poly(lactic-co-glycolic acid), and poly(caprolactone).

Aspect 24. The method of any one of Aspects 22 and 23,
wherein the second hydrophilic block is of a molecular weight in the range of from 0.2 kDa to 100 kDa, from 0.5 kDa to 50 kDa, from 1 kDa to 20 kDa, from 2 kDa to 10 kDa, or of about 5 kDa and
wherein the second hydrophobic block is of a molecular weight in the range of from 0.2 kDa to 100 kDa, from 0.5 kDa to 50 kDa, from 1 kDa to 20 kDa, from 2 kDa to 10 kDa, or of about 5 kDa.

Aspect 25. The method of any one of Aspects 22 through 24, wherein the second stage process solution is miscible with the finishing solvent.

Aspect 26. The method of any one of Aspects 1 through 25, further comprising
concentrating the polymer inverse nanoparticles to form microparticles,
wherein each microparticle comprises a plurality of nanoparticles.

Aspect 27. The method of any one of Aspects 1 through 26,
wherein the water soluble active is anionic and the hydrophilic block is selected to be cationic, so that water soluble active and the hydrophilic block ionically bond or
wherein the water soluble active is cationic and the hydrophilic block is selected to be anionic, so that water soluble active and the hydrophilic block ionically bond.

Aspect 28. The method of any one of Aspects 1 through 27, further comprising adding a tackifier to the process solvent and/or to the nonprocess solvent to increase the hydrophobic block glass transition temperature (Tg).

Aspect 29. The method of any one of Aspects 1 through 28,
wherein the process solvent and the finishing solvent are each independently selected from the group consisting of dimethylsulfoxide (DMSO), propanol, ethanol, methanol, water, and combinations and
wherein the nonprocess solvent is selected from the group consisting of dichloromethane, chloroform, acetone, tetrahydrofuran (THF), methanol, and combinations.

Aspect 30. The method of any one of Aspects 1 through 29, wherein the continuous mixing is through a flash nanoprecipitation process.

Aspect 31. A polymer inverse nanoparticle that encapsulates a water soluble active, comprising
a triblock copolymer comprising two hydrophilic end blocks and a hydrophobic center block;
a core; and
a shell,
wherein the hydrophobic center block is between each of the two hydrophilic end blocks,
wherein the water soluble active and the hydrophilic end blocks are within the core,
wherein the hydrophobic center block is within the shell, and
wherein the hydrophilic end blocks are crosslinked within the core with a crosslinking agent.

Aspect 32. The polymer inverse nanoparticle of Aspect 31, wherein the hydrophobic end blocks are formed from the same monomer.

Aspect 33. The polymer inverse nanoparticle of any one of Aspects 31 and 32, wherein the water soluble active is a cyclic polypeptide.

Aspect 34. The polymer inverse nanoparticle of any one of Aspects 31 and 32, wherein the water soluble active is selected from the group consisting of ovalbumin, lysozyme, and PEP1.

Aspect 35. The polymer inverse nanoparticle of any one of Aspects 31 and 32, wherein the water soluble active is vancomycin.

Aspect 36. The polymer inverse nanoparticle of any one of Aspects 31 through 35,
wherein each hydrophilic end block is independently selected from the group consisting of poly(aspartic acid) and poly(glutamic acid) and
wherein the hydrophobic center block is selected from the group consisting of poly(lactic acid), poly(lactic-co-glycolic acid), and poly(caprolactone).

Aspect 37. The polymer inverse nanoparticle of any one of Aspects 31 through 35, wherein the triblock copolymer is poly(aspartic acid)-b-poly(lactic acid)-b-poly(aspartic acid).

Aspect 38. The polymer inverse nanoparticle of any one of Aspects 31 through 35, wherein the triblock copolymer is poly(glutamic acid)-b-poly(lactic acid)-b-poly(glutamic acid).

Aspect 39. The polymer inverse nanoparticle of any one of Aspects 31 through 35, wherein the triblock copolymer is poly(aspartic acid)-b-poly(lactic-co-glycolic acid)-b-poly(aspartic acid).

Aspect 40. The polymer inverse nanoparticle of any one of Aspects 31 through 35, wherein the triblock copolymer is poly(glutamic acid)-b-poly(lactic-co-glycolic acid)-b-poly(glutamic acid).

Aspect 41. The polymer inverse nanoparticle of any one of Aspects 31 through 40, further comprising
a diblock copolymer comprising a hydrophilic block and a hydrophobic block;
a coating comprising an interior layer and an exterior layer, wherein the hydrophobic block is within the interior layer,
wherein the hydrophilic block is within the exterior layer, and
wherein the interior layer is adjacent to the shell.

Aspect 42. The polymer inverse nanoparticle of Aspect 41, wherein the hydrophilic block is polyethylene glycol (PEG).

Aspect 43. The polymer inverse nanoparticle of any one of Aspects 41 and 42, wherein the hydrophobic block is polylactic acid (PLA).

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:
1. A method of forming a polymer inverse nanoparticle that encapsulates a water soluble active to maximize or optimize encapsulation efficiency and/or to mimimize or optimize burst fraction, comprising:
dissolving the water soluble active at a concentration and a block copolymer at a concentration in an amount of a process solvent to form a process solution; and
continuously mixing the process solution with an amount of a nonprocess solvent at a process temperature to form a first nanoparticle solution comprising polymer inverse nanoparticles having a core and a shell and a first nanoparticle solvent;

adding a second block copolymer to the first nanoparticle solution to form a second stage process solution; and continuously mixing the second stage process solution with a finishing solvent to form a second nanoparticle solution comprising the polymer inverse nanoparticles coated with the second block copolymer, wherein the block copolymer comprises a hydrophilic block and a hydrophobic block having a glass transition temperature (Tg), wherein the hydrophilic block is soluble in the process solvent and is insoluble in the nonprocess solvent, wherein the hydrophobic block is insoluble in the process solvent and is soluble in the nonprocess solvent, wherein the process solution is more polar than the nonprocess solvent, wherein the water soluble active and the hydrophilic block are in the core and the hydrophobic block is in the shell, and wherein the encapsulation efficiency is maximized or optimized by
- (a) selecting the process solvent, so that the hydrophilic block is close to a solubility limit in the process solution for the concentration of the block copolymer, and/or
- (b) crosslinking the hydrophilic block in the core, and/or
- (c) selecting the hydrophilic block to have bonding interactions with the water soluble active in the core, and/or
- (d) selecting the hydrophobic block to have a molecular weight of at least 10 kDa, 20 kDa, 30 kDa, 40 kDa, 50 kDa, 70 kDa, or 100 kDa, and/or
- (e) selecting the process temperature and/or the hydrophobic block, so that the process temperature is less than the hydrophobic block glass transition temperature (Tg), and/or
- (f) selecting the process solvent to have high osmolarity, and/or
- (g) adding a supplemental hydrophobic compound to the process solvent and/or to the nonprocess solvent to increase the bulk of hydrophobic material in the shell, and/or wherein the burst fraction is minimized or optimized by
- (aa) crosslinking the hydrophilic block in the core, and/or
- (bb) increasing the hydrophobic block glass transition temperature (Tg), and/or
- (cc) adding the supplemental hydrophobic compound to the process solvent and/or to the nonprocess solvent to increase the bulk of hydrophobic material in the shell, and wherein the second block copolymer comprises a second hydrophilic block and a second hydrophobic block.

2. The method of claim 1, wherein the second hydrophilic block is selected from the group consisting of poly(ethylene glycol) and poly(propylene oxide) and wherein the second hydrophobic block is selected from the group consisting of poly(lactic acid), poly(lactic-co-glycolic acid), and poly(caprolactone).

3. The method of claim 2, wherein the encapsulation efficiency is maximized by adding the supplemental hydrophobic compound to the nonprocess solvent to increase the bulk of hydrophobic material in the shell, wherein the burst fraction is minimized by adding the supplemental hydrophobic compound to the nonprocess solvent to increase the bulk of hydrophobic material in the shell, and wherein the supplemental hydrophobic compound is selected from the group consisting of a hydrophobic polymer, polylactic acid, vitamin E, and combinations.

4. The method of claim 2, wherein the burst fraction is minimized by selecting the process temperature and/or the hydrophobic block, so that the process temperature is less than the hydrophobic block glass transition temperature (Tg).

5. The method of claim 2, further comprising annealing the polymer inverse nanoparticle, wherein the annealing maximizes the encapsulation efficiency and wherein the annealing optimizes the encapsulation efficiency.

6. The method of claim 2, wherein the water soluble active is selected from the group consisting of a linear polypeptide, a cyclic polypeptide, ovalbumin, lysozyme, PEP1, and vancomycin.

7. The method of claim 2, wherein the hydrophilic block is selected from the group consisting of poly(aspartic acid) and poly(glutamic acid) and wherein the hydrophobic block is selected from the group consisting of poly(lactic acid), poly(lactic-co-glycolic acid), and poly(caprolactone).

8. The method of claim 2, wherein the hydrophilic block is of a molecular weight in the range of from 0.2 kDa to 100 kDa, from 0.5 kDa to 50 kDa, from 1 kDa to 20 kDa, from 2 kDa to 10 kDa, or of about 5 kDa, and wherein the hydrophobic block is of a molecular weight in the range of from 0.5 kDa to 400 kDa, 1 kDa to 200 kDa, from 2 kDa to 100 kDa, from 5 kDa to 100 kDa, from 10 kDa to 40 kDa, of about 10 kDa, of about 20 kDa, or of about 40 kDa.

9. The method of claim 2, wherein the supplemental hydrophobic compound is selected from the group consisting of poly(lactic acid), poly(lactic-co-glycolic acid), and poly(caprolactone).

10. The method of claim 2, wherein the process solvent is miscible with the nonprocess solvent.

11. The method of claim 2, wherein the encapsulation efficiency is optimized by crosslinking the hydrophilic block in the core, wherein the burst fraction is minimized by crosslinking the hydrophilic block in the core, and wherein the crosslinking agent is selected from the group consisting of a metal, calcium, a chelating agent, tetraethylene pentamine (TEPA), and combinations.

12. The method of claim 2, wherein the second hydrophilic block is of a molecular weight in the range of from 0.2 kDa to 100 kDa, from 0.5 kDa to 50 kDa, from 1 kDa to 20 kDa, from 2 kDa to 10 kDa, or of about 5 kDa and wherein the second hydrophobic block is of a molecular weight in the range of from 0.2 kDa to 100 kDa, from 0.5 kDa to 50 kDa, from 1 kDa to 20 kDa, from 2 kDa to 10 kDa, or of about 5 kDa.

13. The method of claim 2, wherein the second stage process solution is miscible with the finishing solvent.

14. The method of claim 2,
- wherein the water soluble active is anionic and the hydrophilic block is selected to be cationic, so that the water soluble active and the hydrophilic block ionically bond or
- wherein the water soluble active is cationic and the hydrophilic block is selected to be anionic, so that the water soluble active and the hydrophilic block ionically bond.

15. The method of claim 2, further comprising adding a tackifier to the process solvent and/or to the nonprocess solvent to increase the hydrophobic block glass transition temperature (Tg).

16. The method of claim 2,
- wherein the process solvent and the finishing solvent are each independently selected from the group consisting of dimethylsulfoxide (DMSO), propanol, ethanol, methanol, water, and combinations and
- wherein the nonprocess solvent is selected from the group consisting of dichloromethane, chloroform, acetone, tetrahydrofuran (THF), methanol, and combinations.

17. The method of claim 2, wherein the continuous mixing is through a flash nanoprecipitation process.

18. The method of claim 1, wherein the process solvent is selected to have high osmolarity by dissolving a salt in the process solvent.

19. The method of claim 1, further comprising adding lecithin to the nonprocess solvent.

* * * * *